(12) United States Patent
Doutriaux et al.

(10) Patent No.: US 6,734,019 B1
(45) Date of Patent: May 11, 2004

(54) **ISOLATED DNA THAT ENCODES AN *ARABIDOPSIS THALIANA* MSH3 PROTEIN INVOLVED IN DNA MISMATCH REPAIR AND A METHOD OF MODIFYING THE MISMATCH REPAIR SYSTEM IN A PLANT TRANSFORMED WITH THE ISOLATED DNA**

(75) Inventors: Marie-Pascale Doutriaux, Saulx les Chartreux (FR); Andreas Stefan Betzner, Page (AU); Georges Freyssinet, Saint Cyr au Mont d'Or (FR); Pascal Perez, Varennes (FR)

(73) Assignee: Aventis Cropscience S.A, Lyon Cedex (FR)

( * ) Notice: Subject to any disclaimer, the term of this patent is extended or adjusted under 35 U.S.C. 154(b) by 0 days.

(21) Appl. No.: 09/529,239

(22) PCT Filed: Oct. 9, 1998

(86) PCT No.: PCT/EP98/06977

§ 371 (c)(1),
(2), (4) Date: Oct. 27, 2000

(87) PCT Pub. No.: WO99/19492

PCT Pub. Date: Apr. 22, 1999

(30) Foreign Application Priority Data

Oct. 10, 1997 (AU) .............................................. P09745

(51) Int. Cl.[7] ........................ C12N 15/29; C12N 15/82; A01H 5/00

(52) U.S. Cl. ..................... 435/419; 435/468; 536/23.6; 800/278; 800/298

(58) Field of Search ............................... 536/23.6, 23.1; 435/320.1, 468, 419; 800/278, 298, 286, 306, 317, 320, 307, 322

(56) References Cited

FOREIGN PATENT DOCUMENTS

| | | |
|---|---|---|
| WO | 9007576 | 7/1990 |
| WO | 9515381 | 6/1995 |
| WO | 9626283 | 8/1996 |
| WO | 96/26283 A1 * | 8/1996 |
| WO | 9701634 | 1/1997 |
| WO | 9737011 | 10/1997 |

OTHER PUBLICATIONS

Eric Alani, The *Saccharomyces cerevisiae* Msh2 and Msh6 Proteins Form a Complex That Specifically Binds to Duplex Oligonucleotides Containing Mismatched DNA Base Pairs, Oct. 1996, Molecular and Cellular Biology, pp. 5604–5615.*

Rice et. al., Genetic Repair of Mutations in Plants Cell–Free Extracts Directed by Specific Chimeric Oligonucleotides, Jun. 200, Plant Physiology, vol. 123, pp. 427–437.*

Colliver et al., Differential modification of flavonoid and isoflavonoid biosynthesis with an antisense chalcone synthase contruct in transgenic *Lotus corniculatus*, 1997, Plant Molecular Biology, vol. 35, pp. 509–522.*

Culligan et al., DNA Mismatch Repair in Plants1, 1997, Plant Physiol, vol. 115, pp. 833–836.*

Letter to the Editor, "Homology" in Protein and Nucleic Acids: A Terminology Muddle and a way out of it, 1987, Cell, vol. 50, p. 667.*

Reeck et al 1987, "Homology" in proteins and nucleic acids: A terminology muddle and a way out of it, Cell 50:667.*

Rice et al 2000, Genetic repari of mutations in plant cell–free extracts directed by specific chimeric oligonucleotides. Plant Physiology 123:427–437.*

Colliver et al 1997, Differential modification of flavonoid and isoflavonoid biosynthesis with an antisense chalcone synthase construct in transgenic *Lotus corniculatus*. Plant Molecular Biology 35:509–522.*

Culligan et al 1997, DNA mismatch repair in plants, An *Arabidopsis thaliana* gene that predicts a protein belonging to the MSH2 subfamily of eukaryotic MutS homologs. Plant Physiology 115(2):833–839.*

Liu et al., "Characterization of the mouse Rep–3 gene: sequence similarities to bacterial and yeast mismatch–repair proteins", *Gene*, vol. 147, 1994, pp. 169–177.

Prolla et al., "MLH1, PMS1, and MSH2 Interactions During the Initiation of DNA Mismatch Repair in Yeast", *Science*, vol. 265, Aug. 19, 1994, pp. 1091–1093.

Acharya et al., "hMSH2 forms specific mispari–binding complexes with hMSH3 and hMSH6", *Proc. Natl. Acad. Sci. USA*, vol. 93, Nov. 1996, pp. 13629–13634.

Iaccarino et al., "MSH6, a *Saccharomyces cerevisiae* protein that binds to mismatches as a heterodimer with MSH2", *Current Biology*, vol. 6, No. 4, 1996, pp. 484–486.

Corradi et al., "cDNA Sequence, Map, and Expression of the Murine Homolog of GTBP, a DNA Mismatch Repair Gene", *Genomics*, vol. 36, 1996, pp. 288–295.

Balestrazzi et al., "Cloning of a cDNA encoding DNA topoisomerase I in *Daucus carota* and expression analysis in relation to cell proliferation", *Gene*, vol. 183, 1996, pp. 183–190.

Culligan et al., "DNA Mismatch Repair in Plants", *Plant Physiol.*, vol. 115, 1997, pp. 833–839.

Watanabe et al., "Genomic Organization and Expression of the Human MSH3 Gene", *Genomics*, vol. 31, 1996, pp. 311–318.

(List continued on next page.)

*Primary Examiner*—David T. Fox
*Assistant Examiner*—David H Kruse
(74) *Attorney, Agent, or Firm*—Baker Botts LLP

(57) ABSTRACT

The present invention relates to an isolated and purified DNA comprising a nucleotide sequence that encodes a polypeptide functionally involved in the DNA mismatch repair system of a plant.

7 Claims, 34 Drawing Sheets

OTHER PUBLICATIONS

Database EMBL Nucleotide and Protein Sequences, Oct. 16, 1997, AC=AF009657.

Database EMBL Nucleotide and Protein Sequences, Mar. 18, 1998, AC=065607.

Database EMBL Nucleotide and Protein Sequences, Jul. 13, 1998, AC=AJ007791.

Database EMBL Nucleotide and Protein Sequences, Oct. 12, 1998, AC=AJ007792.

Database EMBL Nucleotide and Protein Sequences, Dec. 17, 1998, AC=AJ131669.

Asano T et al., 2002, "Rice SPK, a calmodulin–like domain protein kinase, is required for storage product accumulation during seed development: phosphorylation of sucrose synthase is a possible factor" *Plant Cell.* 14(3):619–628.

Jobling SA et al., 2002, "Production of a freeze–thaw–stable potato starch by antisense inhibition of three starch synthase genes" *Nat Biotechnol.* 20(3):295–299.

Scheidig A et al., 2002, "Downregulation of a chloroplast–targeted beta–amylase leads to a starch–excess phenotype in leaves" *Plant J.* 30(5):581–591.

Verpoorte R et al., 2002, "Engineering secondary metabolite production in plants" *Curr Opin Biotechnol.* 13(2):181–187.

Forkmann G et al., 2001, "Metabolic engineering and applications of flavonoids" *Curr Opin Biotechnol.* 12(2):155–160.

Tuteja N et al., 2001, "Molecular mechanisms of DNA damage and repair: progress in plants" *Crit. Rev. Biochem Mol. Biol.* 36(4):337–397.

Zhang Y et al., 2001, "Expression of antisense SnRK1 protein kinase sequence causes abnormal pollen development and male sterility in transgenic barley" *Plant J.* 28(4):431–41.

Cao X et al., 2000, "Conserved plant genes with similarity to mammalian de novo DNA methyltransferases" *Proc Natl Acad Sci USA* 97:4979–4984.

Culligan KM et al., 2000, "Arabidopsis MutS homologs–AtMSH2, AtMSH3, AtMSH6, and a novel AtMSH7–form three distinct protein heterodimers with different specificities for mismatched DNA" *Plant Cell* 12:991–1002.

O'hara P et al., 2000, "Modulation of fatty acid biosynthesis by antisense beta–keto reductase expression" *Biochem Soc Trans.* 28(6):613–615.

Stepanova AN et al., 2000, "Ethylene signaling: from mutants to molecules" *Curr Opin Plant Biol.* 3(5):353–360.

Yanagisawa S, 2000, "Dof1 and Dof2 transcription factors are associated with expression of multiple genes involved in carbon metabolism in maize" *Plant J.* 21(3):281–288.

Ade J et al., 1999, "Four mismatch repair paralogues coexist in *Arabidopsis thaliana*: AtMSH2, AtMSH3, AtMSH6–1 and AtMSH6–2" *Mol. Gen. Genet.* 262(2):239–249.

Martin M et al., 1999, "Antisense–mediated depletion of potato leaf omega3 fatty acid desaturase lowers linolenic acid content and reduces gene activation in response to wounding" *Eur J Biochem.* 262(2):283–290.

Royo J et al., 1999, "Antisense–mediated depletion of a potato lipoxygenase reduces wound induction of proteinase inhibitors and increases weight gain of insect pests" *Proc Natl Acad Sci USA* 96(3):1146–1151.

Schroda M et al., 1999, "A chloroplast–targeted heat shock protein 70 (HSP70) contributes to the photoprotection and repair of photosystem II during and after photoinhibition" *Plant Cell* 11(6):1165–78.

Amor Y et al., 1998, "The involvement of poly(ADP–ribose) polymerase in the oxidative stress response in plants" *FEBS Lett.* 440(1–2):1–7.

Kaldenhoff R et al., 1998, "Significance of plasmalemma aquaporins for water–transport in *Arabidopsis thaliana*" *Plant J.* 14(1):121–128.

Robbins MP et al., 1998, "Genetic manipulation of condensed tannins in higher plants. Ii. Analysis Of birdsfoot trefoil plants harboring antisense dihydroflavonol reductase constructs" *Plant Physiol.* 116(3):1133–1144.

Xu H et al., 1998, "Plant homologue of human excision repair gene ERCC1 points to conservation of DNA repair mechanisms" *Plant J.* 13(6):823–9.

Bavage AD et al., 1997, "Expression of an Antirrhinum dihydroflavonol reductase gene results in changes in condensed tannin structure and accumulation in root cultures of *Lotus corniculatus* (bird's foot trefoil)" *Plant Mol Biol.* 35(4):443–458.

Lee D et al., 1997, "Antisense suppression of 4–coumarate-:coenzyme A ligase activity in Arabidopsis leads to altered lignin subunit composition" *Plant Cell.* 9(11):1985–1998.

Mett VL et al., 1996, "A system for tissue–specific copper–controllable gene expression in transgenic plants: nodule–specific antisense of aspartate aminotransferase–P2" *Transgenic Res.* 5(2):105–113.

Masle J et al., 1993, "Effects of Ambient CO2 Concentration on Growth and Nitrogen Use in Tobacco (*Nicotiana tabacum*) Plants Transformed with an Antisense Gene to the Small Subunit of Ribulose–1,5–Bisphosphate Carboxylase/Oxygenase" *Plant Physiol.* 103(4):1075–1088.

Orozco–Cardenas M et al., 1993, "Expression of an antisense prosystemin gene in tomato plants reduces resistance toward *Manduca sexta* larvae" *Proc Natl Acad Sci USA* 90(17):8273–8276.

Bramley P et al., 1992, "Biochemical characterization of transgenic tomato plants in which carotenoid synthesis has been inhibited through the expression of antisense RNA to pTOM5" *Plant J.* 2(3):343–349.

McGurl B et al., 1992, "Structure, expression, and antisense inhibition of the systemin precursor gene" *Science* 255(5051):1570–1573.

* cited by examiner

COMMENTS/REFERENCES: 52=3' SIDE OF S5 (AtMSH3) 1244bp IN pUC18/Sma1

```
1    CCTAAGAAAGCGCGGCGAAAATTGGCAACCCAAGTTCGCCATAGCCAGACCACGACCTTCATTCTCTTAAACGGAGGA          80

81   GATTACGAATAAAGCAATT ATG GGC AAG CAA AAG CAG CAG ACG ATT TCT CGT TTC TTC GCT CCC         144
                          M   G   K   Q   K   Q   Q   T   I   S   R   F   F   A   P         15

145  AAA CCC AAA TCC CCG ACT CAC GAA CCG AAT CCG GTA GCC GAA TCA TCA ACA CCG CCA CCG         204
     K   P   K   S   P   T   H   E   P   N   P   V   A   E   S   S   T   P   P   P         35

205  AAG ATA TCC GCC ACT GTA TCC TTC TCT CCT AAG CGT AAG CTT CTC TCC GAC CAC CTC             264
     K   I   S   A   T   V   S   F   S   P   S   K   R   K   L   L   S   D   H   L         55

265  GCC GCC GCG TCA CCC AAA AAG CCT AAA CTT TCT CCT CAC ACT CAA AAC CCA GTA CCC GAT         324
     A   A   A   S   P   K   K   P   K   L   S   P   H   T   Q   N   P   V   P   D         75

325  CCC AAT TTA CAC CAA AGA TTT CTC CAG AGA TTT CTG GAA CCC TCG GAG GAA TAT GTT             384
     P   N   L   H   Q   R   F   L   Q   R   F   L   E   P   S   E   E   Y   V   V         95

385  CCC GAA ACG TCA TCA TCG AGG AAA TAC ACA CCA TTG GAA CAG CAA GTT GAG CTA AAG             444
     P   E   T   S   S   S   R   K   Y   T   P   L   E   Q   Q   V   E   L   K         115

445  AGC AAG TAC CCA GAT GTG GTT TTG ATG GTG GAA GTT GGT ATT TAC GCT CAT ATG GAT TTC GGA     504
     S   K   Y   P   D   V   V   L   M   V   E   V   G   I   Y   A   H   M   D   F   G     135

505  GAA GAC GCG GAG ATC GCA GCA CGC GTG TTG GGT ATT TAC GCT CAT ATG GAT CAC AAT TTC         564
     E   D   A   E   I   A   A   R   V   L   G   I   Y   A   H   M   D   H   N   F         155

565  ATG ACG GCG AGT GTG CCA ACA TTT CGA TTG AAT TTC CAT GTG AGA AGA CTG GTG AAT GCA         624
     M   T   A   S   V   P   T   F   R   L   N   F   H   V   R   R   L   V   N   A         175
```

FIG. 4A

| | | | | | | | | | | | | | | | | | | | | |
|---|---|---|---|---|---|---|---|---|---|---|---|---|---|---|---|---|---|---|---|---|
| 625 | GGA | TAC | AAG | ATT | GGT | GTA | GTG | AAG | CAG | ACT | GAA | ACT | GCA | GCC | ATT | AAG | TCC | CAT | GGT | GCA | 684 |
| 176 | G | Y | K | I | G | V | V | K | Q | T | E | T | A | A | I | K | S | H | G | A | 195 |
| 665 | AAC | CGG | ACC | GGC | CCT | TTT | TTC | CGG | GGA | CTG | TCG | GCG | TTG | TAT | ACC | AAA | GCC | ACG | CTT | GAA | 744 |
| 196 | N | R | T | G | P | F | F | R | G | L | S | A | L | Y | T | K | A | T | L | E | 215 |
| 745 | GCG | GCT | GAG | GAT | ATA | AGT | GGT | GGT | TGT | GGT | GAA | GAA | GGT | TTT | GGT | TCA | CAG | AGT | AAT | 804 |
| 216 | A | A | E | D | I | S | G | G | C | G | E | E | G | F | G | S | Q | S | N | 235 |
| 805 | TTC | TTG | GTT | TGT | GTT | GTG | GAT | GAG | AGA | GTT | AAG | TCG | GAG | ACA | TTA | GGC | TGT | GGT | ATT | GAA | 864 |
| 236 | F | L | V | C | V | V | D | E | R | V | K | S | E | T | L | G | C | G | I | E | 255 |
| 865 | ATG | AGT | TTT | GAT | GTT | AGA | GTC | GGT | GTT | GTT | GAA | ATT | TCG | ACA | GGT | GAA | GTT | GTT | 924 |
| 256 | M | S | F | D | V | R | V | G | V | V | E | I | S | T | G | E | V | V | 275 |
| 925 | TAT | GAA | GAG | TTC | AAT | GAT | AAT | TTC | ATG | AGA | AGT | GGA | TTA | GAG | GCT | GTG | ATT | TTG | AGC | TTG | 9884 |
| 276 | Y | E | E | F | N | D | N | F | M | R | S | G | L | E | A | V | I | L | S | L | 295 |
| 985 | TCA | CCA | GCT | GAG | CTG | TTG | CTT | GGC | CAG | CCT | CTT | TCA | CAA | CAA | ACT | GAG | AAG | TTT | TTG | GTG | 1044 |
| 296 | S | P | A | E | L | L | L | G | Q | P | L | S | Q | Q | T | E | K | F | L | V | 315 |
| 1045 | GCA | CAT | GCT | GGA | CCT | ACC | TCA | AAC | GTT | CGA | GTG | GAA | CGT | GCC | TCA | CTG | GAT | TGT | TTC | AGC | 1104 |
| 316 | A | H | A | G | P | T | S | N | V | R | V | E | R | A | S | L | D | C | F | S | 335 |
| 1105 | AAT | GGT | AAT | GCA | GTA | GAT | GAG | GTT | ATT | TCA | TTA | TGT | GAA | AAA | ATC | AGC | GCA | GGT | AAC | TTA | 1164 |
| 336 | N | G | N | A | V | D | E | V | I | S | L | C | E | K | I | S | A | G | N | L | 355 |
| 1165 | GAA | GAT | GAT | AAA | GAA | ATG | AAG | CTG | GAG | GCT | GCT | GAA | AAA | GGA | ATG | TCT | TGC | TTG | ACA | GTT | 1224 |
| 356 | E | D | D | K | E | M | K | L | E | A | A | E | K | G | M | S | C | L | T | V | 375 |

FIG.4B

| 1225 | CAT | ACA | ATT | ATG | AAC | ATG | CCA | CAT | CTG | ACT | GTT | CAA | GCC | CTC | GCC | CTA | ACG | TTT | TGC | CAT | 1284 |
| --- | --- | --- | --- | --- | --- | --- | --- | --- | --- | --- | --- | --- | --- | --- | --- | --- | --- | --- | --- | --- | --- |
| 376 | H | T | I | M | N | M | P | H | L | T | V | Q | A | L | A | L | T | F | C | H | 395 |
| 1285 | CTC | AAA | CAG | TTT | GGA | TTT | GAA | AGG | ATC | CTT | TAC | CAA | GGG | GCC | TCA | TTT | CGC | TCT | TTG | TCA | 1344 |
| 396 | L | K | Q | F | G | F | E | R | I | L | Y | Q | G | A | S | F | R | S | L | S | 415 |
| 1345 | AGT | AAC | ACA | GAG | ATG | ACT | CTC | TCA | GCC | AAT | ACT | CTG | CAA | CAG | TTG | GAG | GTT | GTG | AAA | AAT | 1404 |
| 416 | S | N | T | E | M | T | L | S | A | N | T | L | Q | Q | L | E | V | V | K | N | 435 |
| 1405 | AAT | TCA | GAT | GGA | TCG | GAA | TCT | CTC | TTC | CAT | CAT | AAT | ATG | AAT | CAC | ACA | CTT | ACA | GTA | 1464 |
| 436 | N | S | D | G | S | E | S | L | F | H | H | N | M | N | H | T | L | T | V | 455 |
| 1465 | TAT | GCT | TCC | AGG | CTT | CTT | AGA | CAC | TGG | GTG | ACT | CAT | CCT | CTA | TGC | GAT | AGA | AAT | TTG | ATA | 1524 |
| 456 | Y | A | S | R | L | L | R | H | W | V | T | H | P | L | C | D | R | N | L | I | 475 |
| 1525 | TCT | GCT | CGG | CTT | GAT | GCT | GTT | TCT | GAG | ATT | TCT | GCT | TGC | ATG | GGA | TCT | CAT | AGT | TCT | TCC | 1584 |
| 476 | S | A | R | L | D | A | V | S | E | I | S | A | C | M | G | S | H | S | S | S | 495 |
| 1585 | CAG | CTC | AGC | AGT | GAG | TTG | GTT | GAA | GAA | GGT | TCT | GAG | AGA | GCA | ATT | GTA | TCA | CCT | GAG | TTT | 1644 |
| 496 | Q | L | S | S | E | L | V | E | E | G | S | E | R | A | I | V | S | P | E | F | 515 |
| 1645 | TAT | CTC | GTG | CTC | TCC | TCA | GTC | TTG | ACA | GCT | ATG | TCT | AGA | TCA | TCT | GAT | ATT | CAA | CGT | GGA | 1704 |
| 516 | Y | L | V | L | S | S | V | L | T | A | M | S | R | S | S | D | I | Q | R | G | 535 |
| 1705 | ATA | ACA | AGA | ATC | TTT | CAT | CGG | ACT | GCT | AAA | GCC | ACA | GAG | TTC | ATT | GCA | GTT | ATG | GAA | GCT | 1764 |
| 536 | I | T | R | I | F | H | R | T | A | K | A | T | E | F | I | A | V | M | E | A | 555 |
| 1765 | ATT | TTA | CTT | GCG | GGG | AAG | CAA | ATT | CAG | CGG | CTT | GGC | ATA | AAG | CAA | GAC | TCT | GAA | ATG | AGG | 1824 |
| 556 | I | L | L | A | G | K | Q | I | Q | R | L | G | I | K | Q | D | S | E | M | R | 575 |

FIG.4C

| | | | | | | | | | | |
|---|---|---|---|---|---|---|---|---|---|---|
| 1825 576 | AGT S | ATG M | CAA Q | TCT S | GCA A | ACT T | GTG V | CGA R | TCT S | ACT T | CTT L | TTG L | AGA R | AAA K | TTG L | ATT I | TCT S | GTT V | ATT I | TCA S | 1884 595 |
| 1885 596 | TCC S | CCT P | GTT V | GTG V | GTT V | GAC D | AAT N | GCC A | GGA G | AAA K | CTT L | CTC L | TCT S | GCC A | CTA L | AAT N | AAG K | GAA E | GCG A | GCT A | 1944 615 |
| 1945 616 | GTT V | CGA R | GGT G | GAC D | TTG L | CTC L | GAC D | ATA I | CTA L | ATC I | ACT T | TCC S | AGC S | GAC D | CAA Q | TTT F | CCT P | GAG E | CTT L | GCT A | 2004 635 |
| 2005 636 | GAA E | GCT A | CGC R | CAA Q | GCA A | GTT V | TTA L | GTC V | ATC I | AGG R | GAA E | AAG K | CTG L | GAT D | TCC S | TCG S | ATA I | GCT A | TCA S | TTT F | 2064 655 |
| 2065 656 | CGC R | AAG K | AAG K | CTC L | GCT A | ATT I | CGA R | AAT N | TTG L | GAA E | TTT F | CTT L | CAA Q | GTG V | TCG S | GGG G | ATC I | ACA T | CAT H | TTG L | 2124 675 |
| 2125 676 | ATA I | GAG E | CTG L | CCC P | GTT V | GAT D | TCC S | AAG K | GTC V | CCT P | ATG M | AAT N | TGG W | GTG V | AAA K | GTA V | AAT N | AGC S | ACC T | AAG K | 2184 695 |
| 2185 696 | AAG K | ACT T | ATT I | CGA R | TAT Y | CAT H | CCC P | CCA P | GAA E | ATA I | GTA V | GCT A | GGC G | TTG L | GAT D | GAG E | CTA L | GCT A | CTA L | GCA A | 2244 715 |
| 2245 716 | ACT T | GAA E | CAT H | CTT L | GCC A | ATT I | GTG V | AAC N | CGA R | GCT A | TCG S | TGG W | GAT D | AGT S | TTC F | CTC L | AAG K | AGT S | TTC F | AGT S | 2304 735 |
| 2305 736 | AGA R | TAC Y | TAC Y | ACA T | GAT D | TTT F | AAG K | GCT A | GCC A | GTT V | CAA Q | GCT A | CTT L | GCA A | CTG L | GAC D | TGT C | TTG L | CAC H | 2364 755 |
| 2365 756 | TCC S | CTT L | TCA S | ACT T | CTA L | TCT S | AGA R | AAC N | AAG K | AAC N | TAT Y | GTC V | CGT R | CCC P | GAG E | TTT F | GTG V | GAT D | GAC D | TGT C | 2424 775 |

FIG.4D

```
2425  GAA CCA GTT GAG ATA AAC ATA CAG TCT GGT CGT CAT CCT GTA CTG GAG ACT ATA TTA CAA  2484
776    E   P   V   E   I   N   I   Q   S   G   R   H   P   V   L   E   T   I   L   Q   795

2485  GAT AAC TTC GTC CCA AAT GAC ACA ATT TTG CAT GCA GAA GGG GAA TAT TGC CAA ATT ATC  2544
796    D   N   F   V   P   N   D   T   I   L   H   A   E   G   E   Y   C   Q   I   I   815

2545  ACC GGA CCT AAC ATG GGA GGA AAG AGC TGC TAT ATC CGT CAA GTT GCT TTA ATT TCC ATA  2604
816    T   G   P   N   M   G   G   K   S   C   Y   I   R   Q   V   A   L   I   S   I   835

2605  ATG GCT CAG GTT GGT TCC TTT GTA CCA GCG TCA TTC GCC AAG CTG CAC GTG CTT GAT GGT  2664
836    M   A   Q   V   G   S   F   V   P   A   S   F   A   K   L   H   V   L   D   G   855

2665  GTT TTC ACT CGG ATG GGT GCT TCA GAC AGT ATC CAG CAT GGC AGA AGT ACC TTT CTA GAA  2724
856    V   F   T   R   M   G   A   S   D   S   I   Q   H   G   R   S   T   F   L   E   875

2725  GAA TTA AGT GAA GCG TCA CAC ATA ATC AGA ACC TGT TCT TCT CGT CTT GTT CTT ATA TTA  2784
876    E   L   S   E   A   S   H   I   I   R   T   C   S   S   R   L   V   L   I   L   985

2785  GAT GAG CTT GGA AGA GGC ACT AGC ACA CAC GAC GGT GTA GCC ATT GCC TAT GCA ACA TTA  2844
896    D   E   L   G   R   G   T   S   T   H   D   G   V   A   I   A   Y   A   T   L   915

2845  CAG CAT CTC CTA GCA GAA AAG AGA TGT TTG GTT CTT TTT GTC ACG CAT TAC CCT GAA ATA  2904
916    Q   H   L   L   A   E   K   R   C   L   V   L   F   V   T   H   Y   P   E   I   935

2905  GCT GAG ATC AGT AAC GGA TTC CCA GGT TCT GTT GGG ACA TAC GTC TCG TAT CTG ACA  2964
936    A   E   I   S   N   G   F   P   G   S   V   G   T   Y   H   V   S   Y   L   T   955

2965  TTG CAG AAG GAT AAA GGC AGT TAT GAT CAT GAT GAT GTG ACC TAC CTA TAT AAG CTT GTG  3024
956    L   Q   K   D   K   G   S   Y   D   H   D   D   V   T   Y   L   Y   K   L   V   975
```

FIG.4E

| | | |
|---|---|---|
| 3025<br>976 | CGT GGT CTT TGC AGC AGG AGC TTT GGT TTT AAG GTT GCT CAG CTT GCC CAG ATA CCT CCA<br>R  G  L  C  S  R  S  F  G  F  K  V  A  Q  L  A  Q  I  P  P | 3084<br>995 |
| 3085<br>996 | TCA TGT ATA CGT CGA GCC ATT TCA ATG GCT GCA AAA TTG GAA GCT GAG GTA CGT GCA AGA<br>S  C  I  R  R  A  I  S  M  A  A  K  L  E  A  E  V  R  A  R | 3144<br>1015 |
| 3145<br>1016 | GAG AGA AAT ACA CGC ATG GGA GAA CCA GAA GGA CAT GAA GAA CCG AGA GGC GCA GAA GAA<br>E  R  N  T  R  M  G  E  P  E  G  H  E  E  P  R  G  A  E  E | 3204<br>1035 |
| 3205<br>1036 | TCT ATT TCG GCT CTA GGT GAC TTG TTT GCA GAC CTG AAA TTT GCT CTC TCT GAA GAG GAC<br>S  I  S  A  L  G  D  L  F  A  D  L  K  F  A  L  S  E  E  D | 3264<br>1055 |
| 3265<br>1056 | CCT TGG AAA GCA TTC GAG TTT TTA AAG CAT GCT TGG AAG ATT GCT GGC AAA ATC AGA CTA<br>P  W  K  A  F  E  F  L  K  H  A  W  K  I  A  G  K  I  R  L | 3324<br>1075 |
| 3325<br>1076 | AAA CCA ACT TGT TCA TTT TGA TTTAATCTTAACATTATAGCAACTGCAAGGTCTTGATCATCTGTTAGTTGCG<br>K  P  T  C  S  F  * | 3397<br>1082 |
| 3398<br>1 | TACTAACTT ATG TGT ATT AGT ATA ACA AGA AAA GAG AAT TAG AGAG ATG GAT TCT AAT CCG<br>           M  C  I  S  I  T  R  K  E  N  *     M  D  S  N  P | 3458<br>5 |
| 3459<br>6 | GTG TTG CAG TAC ATC TTT TCT CCA CCC GCA TAA AAAAAAAAAAAAAAAAAAAAAAAAAAAAAAAAAAAA<br>V  L  Q  Y  I  F  S  P  P  A  * | 3522<br>16 |

```
MSH3-At   VDSKVPHNMVKVNSTKKTIRYHPPEIVAGLDELALATEHLAIVNRASWDSFLKSFSRYYTDFKAAVQALAALDCLHSLSTLSRNKNYVRPEFVDD
MSH3-Sc   QIKDLPDDMIKVNNIKMVSRFTTIPRTQKLTQKLEYYKDLIRESELQYKEFLNKITAEYTELRKITLNLAQYDCILSLAATSCNVNYVRPTFVNG

MSH3-At   CEPVEINIQSGRHPVLETILQDNFVPNDTILHAEGEYCQIITGPNMGGKSCYIRQVALISIMAQVGSFVPASFAKLHVLDGVFTRMGASDSIQHG
MSH3-Sc   QQ--AIIAKNARNPIIES-LDVHYVPNDIMMSPENGKINIITGPNMGGKSSYIRQVALLTIMAQIGSFVPAEEIRLSIFENVLIRIGAHDDIING

MSH3-At   RSTFEELSEASHIIRTCSSRSLVILDELGRGTSTHDGVAIAYATLQHLLAEKRC-IVLFVTHYPEIAEISNGFPGSVGTYHVSYLTLQKDKGSY
MSH3-Sc   DSTFKVEMLDILHILKNCNKRSILLLDEVGRGTGTHDGIAISVALIKYFSELSDCPLILFTLHFPMLGEIKS---PLIRNYHMDYVEEQK--TGE

MSH3-At   DHDDVTYLYKLVRGLCSRSFGFKVAQLAQIPPSCIRRAISMAAKLEAEVRARERNTRMGEPEGHEEPRGAEESISALGDLFADLKFALSEEDPWK
MSH3-Sc   DWMSVIFLYKLKKGLTYNSYGMNVAKLARLDKDIINRAFSISEELRKESIN------EDALKI---FSSLKRILKSDN---

MSH3-At   AFEFLKHAWKIAGKIRLKPTCSF----
MSH3-Sc   ----------ITATDKLAKLLSLDIH
```

FIG. 5B

COMMENTS/REFERENCES: 62=3' SIDE OF S8 (AtMSH6) 1379bp IN pUC18/Sma1

```
1    AAAAGTTGAGCCCTGAGGAGTATCGTTTCCGGCCATTTCTACGAGGCAAGGCGAAAATTTTGGGCCAATCTTTCCCCC                                    80

81   TTTCGAATTCTCTCAGCTCAAAACATCGTTTCTCTCTCACTCTCTCACAATTCCAAAAA ATG CAG CGC CAG     153
1                                                                 M   Q   R   Q      4

154  AGA TCG ATT TTG TCT TTC TTC CAA AAA CCC ACC GCG GCG ACT ACG AAG GGT TTG GTT TCC  213
5    R   S   I   L   S   F   F   Q   K   P   T   A   A   T   T   K   G   L   V   S   24

214  GGC GAT GCT GCT AGC GGG GGC GGC AGC GGA GGA CCA CGA TTT AAT GTG AAG GAA GGG     273
25   G   D   A   A   S   G   G   G   S   G   G   P   R   F   N   V   K   E   G       44

274  GAT GCT AAA GGC GAC GCT TCT GTA CGT TTT GCT GTT TCG AAA TCT GTC GAT GAG GTT AGA 333
45   D   A   K   G   D   A   S   V   R   F   A   V   S   K   S   V   D   E   V   R   64

334  GGA ACG GAT ACT CCA CCG GAG AAG GTT CCG CGT CGT GTC CTG CCG TCT GGA TTT AAG CCG 393
65   G   T   D   T   P   P   E   K   V   P   R   R   V   L   P   S   G   F   K   P   84

394  GCT GAA TCC GCC GST GAT GCT TCG TCC CTG TTC TCC AAT ATT ATG CAT AAG TTT GTA AAA 453
85   A   E   S   A   G   D   A   S   S   L   F   S   N   I   M   H   K   F   V   K   104

454  GTC GAT GAT CGA GAT TGT TCT GGA GAG AGC CGA GAA GAT GTT GTT CCG CTG AAT GAT     513
105  V   D   D   R   D   C   S   G   E   S   R   E   D   V   V   P   L   N   D       124

514  TCA TCT CTA TGT ATG AAG GCT AAT GAT GTT ATT CCT CAA TTT CGT TCC AAT AAT GGT AAA 573
125  S   S   L   C   M   K   A   N   D   V   I   P   Q   F   R   S   N   N   G   K   144

574  ACT CAA GAA AGA AAC CAT GCT TTT AGT TTC AGT GGG AGA GCT GAA CTT AGA TCA GTA GAA 633
145  T   Q   E   R   N   H   A   F   S   F   S   G   R   A   E   L   R   S   V   E   164

634  GAT ATA GGA GTA GAT GGC GAT GTT CCT GGT CCA GAA ACA CCA GGG ATG CGT CCA CGT GCT 693
165  D   I   G   V   D   G   D   V   P   G   P   E   T   P   P   G   M   R   P   R   A  184
```

FIG. 9A

| | | | | | | | | | | | |
|---|---|---|---|---|---|---|---|---|---|---|---|
| 694 | TCT | CGC | TTG | AAG | CGA | GTT | CTG | GAG | GAT | GAA | ATG | ACT | TTT | AAG | GAG | GAT | AAG | GTT | CCT | GTA | 753 |
| 185 | S | R | L | K | R | V | L | E | D | E | M | T | F | K | E | D | K | V | P | V | 204 |
| 754 | TTG | GAC | TCT | AAC | AAA | AGG | CTG | AAA | ATG | CTC | CAG | GAT | CCG | GTT | TGT | GGA | GAG | AAA | GAA | 813 |
| 205 | L | D | S | N | K | R | L | K | M | L | Q | D | P | V | C | G | E | K | E | 224 |
| 814 | GTA | AAC | GAA | GGA | ACC | AAA | TTT | GAA | TGG | CTT | GAG | TCT | TCT | CGA | ATC | AGG | GAT | GCC | AAT | AGA | 873 |
| 225 | V | N | E | G | T | K | F | E | W | L | E | S | S | R | I | R | D | A | N | R | 224 |
| 874 | AGA | CGT | CCT | GAT | GAT | CCC | CTT | TAC | GAT | AGA | AAG | ACC | TTA | CAC | ATA | CCA | CCT | GAT | GTT | TTC | 933 |
| 245 | R | R | P | D | D | P | L | Y | D | R | K | T | L | H | I | P | P | D | V | F | 264 |
| 934 | AAG | AAA | ATG | TCT | GCA | TCA | CAA | AAG | CAA | TAT | TGG | AGT | GTT | AAG | AGT | GAA | TAT | ATG | GAC | ATT | 993 |
| 265 | K | K | M | S | A | S | Q | K | Q | Y | W | S | V | K | S | E | Y | M | D | I | 284 |
| 996 | GTG | CTT | TTC | TTT | AAA | GTG | GGG | AAA | TTT | TAT | GAG | CTG | TAT | GAG | CTA | GAT | GCG | GAA | TTA | GGT | 1053 |
| 285 | V | L | F | F | K | V | G | K | F | Y | E | L | Y | E | L | D | A | E | L | G | 304 |
| 1054 | CAC | AAG | GAG | CTT | GAC | TGG | AAG | ATG | ACC | ATG | AGT | GGT | GTG | GGA | AAA | TGC | AGA | CAG | GTT | GGT | 1113 |
| 305 | H | K | E | L | D | W | K | M | T | M | S | G | V | G | K | C | R | Q | V | G | 324 |
| 1114 | ATC | TCT | GAA | AGT | GGG | ATA | GAT | GAG | GCA | GTG | CAA | AAG | CTA | TTA | GCT | CGT | GGA | TAT | AAA | GTT | 1173 |
| 325 | I | S | E | S | G | I | D | E | A | V | Q | K | L | L | A | R | G | Y | K | V | 344 |
| 1174 | GGA | CGA | ATC | GAG | CAG | CTA | GAA | ACA | TCT | GAC | CAA | GCA | AAA | GCC | AGA | GGT | GCT | AAT | ACT | ATA | 1233 |
| 345 | G | R | I | E | Q | L | E | T | S | D | Q | A | K | A | R | G | A | N | T | I | 364 |
| 1234 | ATT | CCA | AGG | AAG | CTA | GTT | CAG | GTA | TTA | ACT | CCA | TCA | ACA | GCA | AGC | GAG | GGA | AAC | ATC | GGG | 1293 |
| 365 | I | P | R | K | L | V | Q | V | L | T | P | S | T | A | S | E | G | N | I | G | 384 |
| 1294 | CCT | GAT | GCC | GTC | CAT | CTT | CTT | GCT | ATA | AAA | GAG | ATC | AAA | ATG | GAG | CTA | CAA | AAG | TGT | TCA | 1353 |
| 385 | P | D | A | V | H | L | L | A | I | K | E | I | K | M | E | L | Q | K | C | S | 404 |

```
1354  ACT GTG TAT GGA TTT GCT TTT GTT GAC TGT GCT GCC TTG AGG TTT TGG GTT GGG TCC ATC  1413
 405   T   V   Y   G   F   A   F   V   D   C   A   A   L   R   F   W   V   G   S   I   424

1414  AGC GAT GAT GCA TCA TGT GCT CTT GGA GCG TTA ATG CAG GTT TCT CCA AAG GAA          1473
 425   S   D   D   A   S   C   A   L   G   A   L   M   Q   V   S   P   K   E           444

1474  GTG TTA TAT GAC AGT AAA GGG GCT CTA TCA AGA GCA GAA AAG GCT CTA AGG AAA TAT ACG  1533
 445   V   L   Y   D   S   K   G   A   L   S   R   A   E   K   A   L   R   K   Y   T   464

1534  TTG ACA GGG TCT ACG GCG GTA CAG CAG TTG GCT CCA GTA CCA CAA AAG CAA GTA ATG GGG  1593
 465   L   T   G   S   T   A   V   Q   Q   L   A   P   V   P   Q   K   Q   V   M   G   484

1594  GCT GCT GGA GTT AGA AAT ATA GAA TCT AAC GGA TAC TTT AAA GGT TCT TCT GAA TCA       1653
 485   A   A   G   V   R   N   I   E   S   N   G   Y   F   K   G   S   S   E   S        504

1654  TGG AAC TGT GCT GTT GAT GGT CTA AAT GAA TGT GAT GTT GCC CTT AGT GCT CTT GGA GAG  1713
 505   W   N   C   A   V   D   G   L   N   E   C   D   V   A   L   S   A   L   G   E   524

1714  CTA ATT AAT CAT CTG TCT AGG CTA AAG CTA GAA GAT GTA CTT AAG CAT GGG GAT ATT TTT  1773
 525   L   I   N   H   L   S   R   L   K   L   E   D   V   L   K   H   G   D   I   F   544

1774  CCA TAC CAA GTT TAC AGG GGT TGT CTC AGA ATT GAT GGC CAG ACG TTG TAC AAA CTT GAG  1833
 545   P   Y   Q   V   Y   R   G   C   L   R   I   D   G   Q   T   L   Y   K   L   E   564

1834  ATA TTT AAC AGC TGT CCA GAT GGT CCT TCA GGG ACC TTG TAC AAA TAT CTT GAT AAC       1893
 565   I   F   N   S   C   P   D   G   P   S   G   T   L   Y   K   Y   L   D   N        584

1894  TGT GTT AGT CCA ACT GGT AAG CGA CTC TTA AGG AAT TGG ATC TGC CAT CCA CTC AAA GAT  1953
 585   C   V   S   P   T   G   K   R   L   L   R   N   W   I   C   H   P   L   K   D   604

1954  GTA GAA AGC ATC AAT AAA CGG CTT GAT GTA GTT GAA GAA TTC ACG GCA AAC TCA GAA AGT  2013
 605   V   E   S   I   N   K   R   L   D   V   V   E   E   F   T   A   N   S   E   S   624
```

```
2014  ATG CAA ATC ACT GGC CAG TAT CTC CAC AAA CTT CCA GAC TTA GAA AGA CTG CTC GGA CGC  2073
 625   M   Q   I   T   G   Q   Y   L   H   K   L   P   D   L   E   R   L   L   G   R    644

2074  ATC AAG TCT AGC GTT CGA TCA GCC TCT GTG TTG CCT GCT CTT CTG GGG AAA AAA GTG       2133
 645   I   K   S   S   V   R   S   A   S   V   L   P   A   L   L   G   K   K   V        664

2134  CTG AAA CAA CGA GTT AAA GCA GTT AAA CAG AAG GAA TCA AAT ATG ATG AGT TTG CTT TAT   2193
 665   L   K   Q   R   V   K   A   V   K   Q   K   E   S   N   M   M   S   L   L   Y    684

2194  CTG TTG GCT CTA CAG AAA AGC GGG AAA AGC GGG CTA GAG TTA TTT CTT TCT CAA TTC AAA   2253
 685   L   L   A   L   Q   K   S   G   K   S   G   L   E   L   F   L   S   Q   F   K    704

2254  CTT CCT ATA TTA GTA GGA AAA AAT TAT CAG AAC CAA GAT GTG ACA GAT GAA AAC GCT GAA   2313
 705   L   P   I   L   V   G   K   N   Y   Q   N   Q   D   V   T   D   E   N   A   E    724

2314  ATA GAT AGC GAC TTT CCA AAT TAT CAG AAC CAA GAT GTG ACA GAT GAA AAC GCT GAA ACT   2373
 725   I   D   S   D   F   P   N   Y   Q   N   Q   D   V   T   D   E   N   A   E   T    744

2374  CTC ACA ATA ATT CTT GAA ATC TTT TTT GCA ATC GAA ACT CAA TGG TCT GAG GTC ATT CAC   2433
 745   L   T   I   I   L   E   I   F   F   A   I   E   T   Q   W   S   E   V   I   H    764

2434  ACC ATA AGC TGC CTA GAT GTC CTG AGA TCT TTT GCA ATC GCA GCA AGT GCA GCT CTC TCT   2493
 765   T   I   S   C   L   D   V   L   R   S   F   A   I   A   A   S   A   A   L   S    784

2494  AGC ATG GCC AGG CCT GTT ATT AAA ATC CAA GAA TCA GAA GCT ACA GAT CAG AAT CAG GCA   2553
 785   S   M   A   R   P   V   I   K   I   Q   E   S   E   A   T   D   Q   N   Q   A    804

2554  AAA GGG CCA ATA CTT AAA CTT CAA GGA CTA TGG CAT CCA TTT GCA GTT GCA GCC GAT GGT   2613
 805   K   G   P   I   L   K   L   Q   G   L   W   H   P   F   A   V   A   A   D   G    824

2614  CAA TTG CCT GTT CCG AAT GAT ATA CTC CTT GGC GAG GCT AGA AGA AGC AGT GGC AGT ATT   2673
 825   Q   L   P   V   P   N   D   I   L   L   G   E   A   R   R   S   S   G   S   I    844
```

FIG. 9D

```
2674  CAT CCT CGG TCA TTG TTA CTG ACG GGA CCA AAC ATG GGC GGA AAA TCA ACT CTT CGT  2733
 845   H   P   R   S   L   L   L   T   G   P   N   M   G   G   K   S   T   L   R    864

2734  GCA ACA TGT CTG GCC GTT ATC TTT GCC CAA CTT GGC TAC GTG CCG TGT TCT TGC       2793
 865   A   T   C   L   A   V   I   F   A   Q   L   G   Y   V   P   C   S   C        884

2794  GAA ATC TCC CTC GTG GAT ACT ATC TTC ACA AGG CTT GGC GCA TCT GAT AGA ATG ACA  2853
 885   E   I   S   L   V   D   T   I   F   T   R   L   G   A   S   D   R   M   T    904

2854  GGA GAG AGT ACC TTT TTG GTA GAA TGC ACT GAG ACA GCG TCA GTT CTT CAG AAT GCA ACT  2913
 905   G   E   S   T   F   L   V   E   C   T   E   T   A   S   V   L   Q   N   A   T    924

2914  CAG GAT TCA CTA GTA ATC CTT GAC GAA CTG GGC AGA GGA ACT AGT ACT TTC GAT GGA TAC  2973
 925   Q   D   S   L   V   I   L   D   E   L   G   R   G   T   S   T   F   D   G   Y    944

2974  GCC ATT GCA TAC TCG GTT TTT CGT CAC CCT CTG GTA GAG AAA GTT CAA TGT CGG ATG CTC TTT  3033
 945   A   I   A   Y   S   V   F   R   H   P   L   V   E   K   V   Q   C   R   M   L   F    964

3034  GCA ACA CAT TAC CAC CCT CTC ACC AAG GAA TTC GCG AGT CCA CGT GTC ACC TCG AAA  3093
 965   A   T   H   Y   H   P   L   T   K   E   F   A   S   H   P   R   V   T   K    984

3094  CAC ATG GCT TGC GCA TTC CGT AAA TCA AGA TCT GAT TAT CAA CCA GGT TGT GAT CAA GAC  3153
 985   H   M   A   C   A   F   R   K   S   R   S   D   Y   Q   P   G   C   D   Q   D    1004

3154  CTA GTG TTC TTG TAC CGT TTA ACC CAA GAG GCT TGT CCT GAA ACA GCA GGA CTT CAA GTG  3213
1005   L   V   F   L   Y   R   L   T   Q   E   A   C   P   E   T   A   S   G   L   Q   V   1024

3214  GCA CTC ATG GCT GGA ATA CCA AAC CAA GTG GTT GAA ACA GCA TCA GGT GCT CAA GCC  3273
1025   A   L   M   A   G   I   P   N   Q   V   V   E   T   A   S   G   A   Q   A    1044

3274  ATG AAG AGA TCA ATT GGG GGA AAC TTC AAG TCA AGT GAG CTA AGA TCT GAG TTC TCA AGT  3333
1045   M   K   R   S   I   G   G   N   F   K   S   S   E   L   R   S   E   F   S   S    1064
```

FIG. 9E

```
3334  CTG CAT GAA GAC TGG CTC AAG TCA TTG GTG GGT ATT TCT CGA GTC GCC CAC AAC AAT GCC  3393
1065   L   H   E   D   W   L   K   S   L   V   G   I   S   R   V   A   H   N   N   A  1084

3394  CCC ATT GGC GAA GAT GAC TAC GAC ACT TTG TTT TGC TTA TGG CAT GAG ATC AAA TCC TCT  3453
1085   P   I   G   E   D   D   Y   D   T   L   F   C   L   W   H   E   I   K   S   S  1104

3454  TAC TGT GTT CCC AAA TAA ATG GCT ATG ACA TAA CACTATCTGAAGCTCGTTAAGTCTTTGCCTCTCT   3521
1105   Y   C   V   P   K   *   M   A   M   T   *                                        5

3522  G ATG TTT ATT CCT CTT AAA AAA TGC TTA TAT ATC AAA AAA TTG TTT CCT CGA TTA AAA    3579
   1    M   F   I   P   L   K   K   C   L   Y   I   K   K   L   F   P   R   L   K      19

3580  AAA AAA AAA AAA AAA AAA AAA AAA AAA                                               3606
  20    K   K   K   K   K   K   K   K   K                                                28
```

```
AtMSH6-mi   QKTKGPILKIQGLWHPFA--VAADGQLPVPNDTLLGEARRSSGSIHPRSLLTGPNMGGKSTLLRATGLAVIFAQLGCYVPCESCEISLVDTIFTRLGASDRIMT
MSH6_yeast  QLNG--FLKFKSLRHPCFNLGATTAKDFIPNDIELGKEQ-------PRLGLLTGANAAGKSTILRMACIAVIMAQMGCYVPCESAVLTPIDRIMTRLGANDNIMQ AtMSH6-mi   GESTFLVECTETASVLQMATQDSLVILDELGRGTSTFDGYATAYSVFRHLVEKVQCRMLFATHYHPLTKEFASHPRVTSKHMACAFKSRSDYQPRGCDQDLVFLY
MSH6_yeast  GKSTIFFVELAEIKKILDMATNRSLLVVDELGRGGSSSDGFAIAESVLHHIVATHIQSLGFFATHYGTLASSFKHHPQVRPLKMSILVDEAT------RNVTFLY AtMSH6-mi   RLTEGACPESYGLQVALNAGIPNQVVETASGAAQ--------AMKRSIGENFKSSELRSEFSSHEDWLKSLVGISRVAHNNAPIGE----DDYDTLFCLWHEIK
MSH6_yeast  KMLEGSEGSFGMHVASMCGIISKEIIDNAQIAADNLEHTSRLVKERDLAANLNGEVVSVPGGLQSDFVRIAYGDG-LKNTKLGSGEGVLNYDWNIKRNVLKSLF AtMSH6-mi   SSYCVPK-
MSH6_yeast  SIDDLQS
```

FIG. 10B

| | |
|---|---|
| TTTTTTGGTTGCTAACAATAAAGGTATACGGTTTTATGTCATCAATATAA | 50 |
| CTATATATAAAAGAAATGAAAGATATATATTGTTTTTTCATTTATCAAAC | 100 |
| AAAACAACAAGACTTTTTTTTTACTTTTTACATTGGTCAACAAAATACAA | 150 |
| GATAAACGACATCGTTTAATCATTTCCCAATTTTACCCCTAAGTTTAACA | 200 |
| CCTAGAACCTTCTCCATCTTCGCAAGCACAGCCTGATTAGGAACAGCTTT | 250 |
| ACCATTCTCATATTCCTGAACTACCTGAGTCCTCTCATTGATCTGTTTCG | 300 |
| CCAAATCCGCTTGTGACATCTTCTTCTCCAATCTCGCTTTCTGTATCATC | 350 |
| AACCTCACCTCTGCTTTCACACGATCCATCGCCGCAGGCTCTGTTTCTTC | 400 |
| TTCCAGCTTCTTCGTGTTAATCACCGGAACCGCCGTAGATTTCCCCTTTT | 450 |
| TGTTCGAACCGGCATCGAATTTCTTAACCGTTTGAACCGCGACACCGTTT | 500 |
| CTCAGAGCTGCGTTAACCGCTTTCGGATCGCGTAGGTCTTGGCTCTTTTG | 550 |
| TTTTGATTTGTGGAGAACTACTGGTTCCCAGTCTTGTGTTACTGCTCCTG | 600 |
| GGTATCTGCTCGGCATCGTCGATGAATTGAGAGAAAGGAACAACGCGAAA | 650 |
| ATTTTATTAATCTGAGTTTTGAAATTGAGAAACGATGAAGATGAAGAATG | 700 |
| TTGTTGAGAGGATTGTGATATTTATATATACGAAGATTGGTTTCTGGAGA | 750 |
| ATTCGATCATCTTTTTCTCCATTTTCGTCTCTGGAACGTTCTTAGAGATG | 800 |
| ATTGACGACGTGTCATTATCTGATTTGCAGTTAACCAATGCTTTTTGGGT | 850 |
| TGGATTCGTGGTACACCATATTATCCGATTTGGCTCAATGGTTTTTATATA | 900 |
| AATTTGGTTTTCGGTTCGGTTATGAGTTATCATTAAAATTAAGCTAACCA | 950 |
| AAAATTTTCGTAAAATTTATTTCGGTTTCAATTCGGATCCCTTACTTCCA | 1000 |
| GAACCGAATTATTCGAAACCGGGGTTAGCCGAACCGAATACCAATGCCTG | 1050 |
| ATTGACTCGTTGGCTAGAAAGATCCAACGGTATACAATAATAGAACATAA | 1100 |
| ATCGGACGGTCATCAAAGCCTCAAAGAGTGAACAGTCAACAAAAAAAGTT | 1150 |
| GAGCCCTGAGGAGTATCGTTTCCGCCATTTCTACGACGCAAGGCGAAAAT | 1200 |
| TTTTGGCGCCAATCTTTCCCCCCTTTCGAATTCTCTCAGCTCAAAACATC | 1250 |
| GTTTCTCTCACTCTCTCTCACAATTCCAAAAAATGCAGCGCCAGAGAT | 1300 |
| CGATTTTGTCTTTCTTCCAAAAACCCACGGCGGCGACTACGAAGGGTTTG | 1350 |
| GTTTCCGGCGATGCTGCTAGCGGCGGGGGCGGCAGCGGAGACCACGATTT | 1400 |
| AATGTGAAGGAAGGGGATGCTAAAGGCGACGCTTCTGTACGTTTTGCTGT | 1450 |
| TTCGAAATCTGTCGATGAGGTTAGAGGAACGGATACTCCACCGGAGAAGG | 1500 |
| TTCCGCGTCGTGTCCTGCCGTCTGGATTTAAGCCGGCTGAATCCGCCGGT | 1550 |
| GATGCTTCGTCCCTGTTCTCCAATATTATGCATAAGTTTGTAAAAGTCGA | 1600 |
| TGATCGAGATTGTTCTGGAGAGAGGTACTAATCTTCGATTCTCTTAATTT | 1650 |
| TGTTATCTTTAGCTGGAAGAAGAAGATTCGTGTAATTTGTTGTATTCGTT | 1700 |
| GGAGAGATTCTGATTACTGCATTGGATCGTTGTTTACAAATTTTCAGGAG | 1750 |
| CCGAGAAGATGTTGTTCCGCTGAATGATTCATCTCTATGTATGAAGGCTA | 1800 |
| ATGATGTTATTCCTCAATTTCGTTCCAATAATGGTAAAACTCAAGAAAGA | 1850 |
| AACCATGCTTTTAGTTTCAGTGGGAGAGCTGAACTTAGATCAGTAGAAGA | 1900 |
| TATAGGAGTAGATGGCGATGTTCCTGGTCCAGAAACACCAGGGATGCGTC | 1950 |
| CACGTGCTTCTCGCTTGAAGCGAGTTCTGGAGGATGAAATGACTTTTAAG | 2000 |
| GAGGATAAGGTTCCTGTATTGGACTCTAACAAAAGGCTGAAAATGCTCCA | 2050 |

FIG. 11A

```
GGATCCGGTTTGTGGAGAGAAGAAAGAAGTAAACGAAGGAACCAAATTTG      2100
AATGGCTTGAGTCTTCTCGAATCAGGGATGCCAATAGAAGACGTCCTGAT      2150
GATCCCCTTTACGATAGAAAGACCTTACACATACCACCTGATGTTTTCAA      2200
GAAAATGTCTGCATCACAAAAGCAATATTGGAGTGTTAAGAGTGAATATA      2250
TGGACATTGTGCTTTTCTTTAAAGTGGTTAGTAACTATTAATCTAGTGTT      2300
CAATCCATTTCCTCAATGTGATTTGTTCACTTACATCTGTTTACGTTATG      2350
CTCTTCTCAGGGGAAATTTTATGAGCTGTATGAGCTAGATGCGGAATTAG      2400
GTCACAAGGAGCTTGACTGGAAGATGACCATGAGTGGTGTGGGAAAATGC      2450
AGACAGGTAAATTAGTTGAAACAACTGGCCTGCTTGAATTATTGTGTCTA      2500
TAAATTTTGACACCACCTTTTGTTTCAGGTTGGTATCTCTGAAAGTGGGA      2550
TAGATGAGGCAGTGCAAAAGCTATTAGCTCGTGGGTAAGGGAACCATCAT      2600
ACTTTATGGAATTCGTTTACTGCTACTTCGGCTAGGATTTAAGAAATGGA      2650
AATCACTTCAAGCATCATTAGTTAGGATCCTGAGAACTCAGGATGTTTTC      2700
TTATTCGTTATATAATAAGTCTTTTCATCAAGGAGTAACAAACAAAACTT      2750
GCACAATATTTGTGTGCTCACTGGCAAGGCATATATACCCAGCTAACCTT      2800
TGCTAGTTCACTGTAGTAACAGTTACGGATAATATATGTTTACTTGTATG      2850
TGGTACCCTCATTTTGTCTCTCATGGAGGCTTTCAAGCCTTGTGTTGAAA      2900
CTGGATAGTTACATATGCTTCCAACAGAAACTAGCATGCAGATTCATATG      2950
CTTTCCTATTCTACTAATTATGTATTGACACACTCGTTGTTTCTTTTGAA      3000
AGATATAAAGTTGGACGAATCGAGCAGCTAGAAACATCTGACCAAGCAAA      3050
AGCCAGAGGTGCTAATACTGTAAGTTTTCTTGGATAGGTCAAGGAGAGTG      3100
TTGCAGACTGTTTTTGATCATTTCTTTTTCTGTACATTACTTTCATGCTG      3150
TAATTAACTCAATGGCTATTCTGGTCTGATTATCAGATAATTCCAAGGAA      3200
GCTAGTTCAGGTATTAACTCCATCAACAGCAAGCGAGGGAAACATCGGGC      3250
CTGATGCCGTCCATCTTCTTGCTATAAAAGAGGTTTGTTATTTACTTATT      3300
TATCTTATCATGTTCAGTTCATCCAAGTCCTGAAAAATTACACTCTTCTT      3350
TACCAATCTTCCATCAAGCTGTGTAAAGGATTTGGAATTAGAAAATCATT      3400
ATTTGATGCTTTGTTTTATATGCAAGAGGTTCCCTTGAAAAGATCTGTTT      3450
AAGATTCTTTGCACTTGAAAAAATTCAATCTTTTTAAGTGAATCCCCTACT      3500
TTCTTACAATGATCATAGTCTGCAATTGCATGTCAAGTAATATCATTCCT      3550
TGTTACTGCATCCCCCTCTTTCTTAATGACCATTGTCTATGTTGTGTTTG      3600
TCTCGTGTGCTGGAGAAAATGATAGCTGATCCAAGCTGTACATTATCATG      3650
ATTAAGTAGCTGCTCAGGAATTGCCTTTGGTTACATTGCCTAATGGTTTG      3700
ATGTCAATTTTTCTTCTGAATCTTTATTTTAGATCAAAATGGAGCTACAA      3750
AAGTGTTCAACTGTGTATGGATTTGCTTTTGTTGACTGTGCTGCCTTGAG      3800
GTTTTGGGTTGGGTCCATCAGCGATGATGCATCATGTGCTGCTCTTGGAG      3850
CGTTATTGATGCAGGTAAGCAAGTGTATTCTGTATCTTATGTGTACCATG      3900
TGACTTCCTGTGCATATATTTGGGTTGCAGGAACTAATTCTGAATCACCA      3950
TTTGGTATGTTTTTTCCAGGTTTCTCCAAAGGAAGTGTTATATGACAGTA      4000
AAGGTAAACTGCTTGTATCGCCAGTTGTTTTGTTAAACAGAATTTAAGGT      4050
AAATGACACTGGTTAATTTAAAGTGCATACATGTTGAAATATTGCAGGGC      4100
```

FIG. 11B

| | |
|---|---|
| TATCAAGAGAAGCACAAAAGGCTCTAAGGAAATATACGTTGACAGGTACC | 4150 |
| ATTTCAGTAGGCAAGCTAACTGACAATTTAACCGCTCACCGAATGATAGG | 4200 |
| TCTCTTAAACATTGCTAATGTAGATGATGTTTATGTTTCAATCTAATAGG | 4250 |
| GTCTACGGCGGTACAGTTGGCTCCAGTACCACAAGTAATGGGGGATACAG | 4300 |
| ATGCTGCTGGAGTTAGAAATATAATAGAATCTAACGGATACTTTAAAGGT | 4350 |
| TCTTCTGAATCATGGAACTGTGCTGTTGATGGTCTAAATGAATGTGATGT | 4400 |
| TGCCCTTAGTGCTCTTGGAGAGCTAATTAATCATCTGTCTAGGCTAAAGG | 4450 |
| TGTGTTGGCTTGTTTAGTTTTTTGCTTTTCACAAATTAAGCAAAGGAACTT | 4500 |
| TTCATAACTTACAGTTTCTATCTACTTGCAGCTAGAAGATGTACTTAAGC | 4550 |
| ATGGGGATATTTTTCCATACCAAGTTTACAGGGGTTGTCTCAGAATTGAT | 4600 |
| GGCCAGACGATGGTAAATCTTGAGATATTTAACAATAGCTGTGATGGTGG | 4650 |
| TCCTTCAGGCAAGTGCATATTTCTTTTTTGATAACTTCAACTAGAGGGCA | 4700 |
| GACATAGAAGGAAAAATTCTAATACTTCGTACGGATCTCCAGTAAGTAAT | 4750 |
| AGCCGATTTTTGTTTACCTATGTAGGGACCTTGTACAAATATCTTGATAA | 4800 |
| CTGTGTTAGTCCAACTGGTAAGCGACTCTTAAGGAATTGGATCTGCCATC | 4850 |
| CACTCAAAGATGTAGAAAGCATCAATAAACGGCTTGATGTAGTTGAAGAA | 4900 |
| TTCACGGCAAACTCAGAAAGTATGCAAATCACTGGCCAGTATCTCCACAA | 4950 |
| ACTTCCAGACTTAGAAAGACTGCTCGGACGCATCAAGTCTAGCGTTCGAT | 5000 |
| CATCAGCCTCTGTGTTGCCTGCTCTTCTGGGGAAAAAAGTGCTGAAACAA | 5050 |
| CGAGTAAGTATCAATCACAAGTTTTCTGAGTAATGCCTTCCATGAGTAGT | 5100 |
| ATAGGACTAAAACATTACGGGTCTAGCTAAAGACTGTTCTCCTTCTTTTG | 5150 |
| CAATGTCTGGTTATTCATTACATTTCTCTTAACTTATTGCATTGCAGGTT | 5200 |
| AAAGCATTTGGGCAAATTGTGAAAGGGTTCAGAAGTGGAATTGATCTGTT | 5250 |
| GTTGGCTCTACAGAAGGAATCAAATATGATGAGTTTGCTTTATAAACTCT | 5300 |
| GTAAACTTCCTATATTAGTAGGAAAAAGCGGGCTAGAGTTATTTCTTTCT | 5350 |
| CAATTCGAAGCAGCCATAGATAGCGACTTTCCAAATTATCAGGTGCCCAT | 5400 |
| CTATCTTTCATACTTTACAACAAAATGTCTGTCACTACTCAAAGCAATGC | 5450 |
| ATATGGCTTAGATCTCAACTCACACCCCGAGGATCCTAAAGGGATTTGCT | 5500 |
| TTTTATTCCTAATGTTTTTGGATGGTTTGATTTATTTCTAACTTGAACTT | 5550 |
| ATTAATCTTGTACCAGAACCAAGATGTGACAGATGAAAACGCTGAAACTC | 5600 |
| TCACAATACTTATCGAACTTTTTATCGAAAGAGCAACTCAATGGTCTGAG | 5650 |
| GTCATTCACACCATAAGCTGCCTAGATGTCCTGAGATCTTTTGCAATCGC | 5700 |
| AGCAAGTCTCTCTGCTGGAAGCATGGCCAGGCCTGTTATTTTTCCCGAAT | 5750 |
| CAGAAGCTACAGATCAGAATCAGAAAACAAAAGGGCCAATACTTAAAATC | 5800 |
| CAAGGACTATGGCATCCATTTGCAGTTGCAGCCGATGGTCAATTGCCTGT | 5850 |
| TCCGAATGATATACTCCTTGGCGAGGCTAGAAGAAGCAGTGGCAGCATTC | 5900 |
| ATCCTCGGTCATTGTTACTGACGGGACCAAACATGGGCGGAAAATCAACT | 5950 |
| CTTCTTCGTGCAACATGTCTGGCCGTTATCTTTGCCCAAGTTTGTATACT | 6000 |
| CGTTAGATAATTACTCTATTCTTTGCAATCAGTTCTTCAACATGAATAAT | 6050 |
| AAATTCTGTTTTCTGTCTGCAGCTTGGCTGCTACGTGCCGTGTGAGTCTT | 6100 |
| GCGAAATCTCCCTCGTGGATACTATCTTCACAAGGCTTGGCGCATCTGAT | 6150 |

FIG.11C

```
AGAATCATGACAGGAGAGAGTAAGTTTTGTTCTCAAAATACCAATTCCTC    6200
GAACTATTTACTCAGATTTTGTCTGATTGGACAAGGTGGTTTTGCTTTTT    6250
TTTAGGTACCTTTTTGGTAGAATGCACTGAGACAGCGTCAGTTCTTCAGA    6300
ATGCAACTCAGGATTCACTAGTAATCCTTGACGAACTGGGCAGAGGAACT    6350
AGTACTTTCGATGGATACGCCATTGCATACTCGGTAACCTGCTCTTCTCC    6400
TTCAACTTATACTTGTTGATCAACAAAAACATGCAATTCATTTTGCTGAA    6450
ACTTATTGATTTATATCAGGTTTTTCGTCACCTGGTAGAGAAAGTTCAAT    6500
GTCGGATGCTCTTTGCAACACATTACCACCCTCTCACCAAGGAATTCGCG    6550
TCTCACCCACGTGTCACCTCGAAACACATGGCTTGCGCATTCAAATCAAG    6600
ATCTGATTATCAACCACGTGGTTGTGATCAAGACCTAGTGTTCTTGTACC    6650
GTTTAACCGAGGGAGCTTGTCCTGAGAGCTACGGACTTCAAGTGGCACTC    6700
ATGGCTGGAATACCAAACCAAGTGGTTGAAACAGCATCAGGTGCTGCTCA    6750
AGCCATGAAGAGATCAATTGGGGAAAACTTCAAGTCAAGTGAGCTAAGAT    6800
CTGAGTTCTCAAGTCTGCATGAAGACTGGCTCAAGTCATTGGTGGGTATT    6850
TCTCGAGTCGCCCACAACAATGCCCCCATTGGCGAAGATGACTACGACAC    6900
TTTGTTTTGCTTATGGCATGAGATCAAATCCTCTTACTGTGTTCCCAAAT    6950
AAATGGCTATGACATAACACTATCTGAAGCTCGTTAAGTCTTTTGCTTCT    7000
CTGATGTTTATTCCTCTTAAAAAATGCTTATATATCAAAAAATTGTTTCC    7050
TCGATTATAACAAGATTATATATGTATCTGTCGGTTTAGCTATGGTATAT    7100
AATATATGTATGTTCATGAGATTGGTCAAGAGAAATACTCACAAACAGTA    7150
TATTAAGAAGGAAATATGTTTATGCATTAATTTAAGTTTCAAGATAAACT    7200
GCAAATAACCTCGACTAAAGTTGCAAAGACCAAACACAAATTACAAAACT    7250
TATAAGACTTAAGTTCTGAATTCCCTAAAACCAAAAAAAAAAACAGAACA    7300
TATTTTGTTGCATCTACAAACAACACAAACCTACATAGTTTATAACTTAC    7350
TCATCACTGAGATTAACATCAGAATCATTCTCCATTTCTTCATCTTCACT    7400
CTCATCATCATCACCACCACCATGATGATTCTCCTCCTCTTCACGTAACC    7450
TAGCAATCTCACTCTGAGCTCTATCAACAATCTGCTTCTTCTGCAACTCC    7500
AAATCTCTCTGAAAATCAGCTCTCATCTTCTCCAACTCCTTCATTTGCTC    7550
TTTCTTACTCTTCTCCATCTTCTCATAAACCTTCCCAAACCTCTCAACAG    7600
AATCCGCCAACATCTTATACGAAGCAGCGTCATTAACCTTCTTCCTCTCG    7650
TACTCAACCTCATCATCCTCATCCTCCTCCTCTTCAGAATCACCAGGACT    7700
ATCCATCATCTCATCAAACCCATTAGACTTATCTAAATAAACCTTAGTGT    7750
TCATAAACACAAACTCACCTGAATCAACACCACAAGCTAAACCTAAATCC    7800
GACTTGGGCGAAACACAAAGCAACATATCCAACTTATTGAAAAACGACCA    7850
TTTACTTGAACCTAAACCTGATTTCTCAACCTTAATCTTCTCTTTTCTAT    7900
ACTTCCTCTTCAAGTCATCAATCATTCTCCTACATTGCGTCTCAGATTTC    7950
TCCATCCTTAGCTCCTCACTCACTTTCTCAGCTACTTCATTCCAATCCTC    8000
GTTCCTCAAACTCCTTCTACCCAATTGCAAAAACCTATCTCCCCAAACTT    8050
CAAGCAACACAA                                          8062
```

FIG. 11D

COMMENTS/REFERENCES: AtMSH3 3' SIDE ANTISENSE: AtMSH3 3' (13=2104bp) FROM pUC18/13 Sal1/Sst1/T4 INTO pCW164 BamH1/T4 IN AGROBACTERIUM LBA4404

COMMENTS/REFERENCES: AtMSH6 3'/AtMSH3 3' ANTISENSE: AtMSH6 (S8) 3' SIDE (62=1379bp)
Sal1/Sst1/T4 INTO pPF13 (pCW164 AtMSH3 (S5) 3' SIDE (13=2104) ANTISENS)/Sma1.
IN LB4404

COMMENTS/REFERENCES: AtMSH3 3'/AtMSH6 3' ANTISENS (D): AtMSH3 (S5) 3' SIDE (13=2104bp) Sal1/Sst1/T4 INTO pPF14 (AtMSH6 (S8) 3' SIDE (62=1379bp) ANTISENSE INTO pCW164)/Sma1. IN LBA4404

COMMENTS/REFERENCES: AtMSH3 (S8) COMPLETE, SENSE ORIENTATION: pPF26 (3342bp) Sma1 INTO pCW164 Sma1

COMMENTS/REFERENCES: pP2P111 WITH codA EcoR1 CASSETTE IN EcoR1 SITE AND Hind3 GUS CASSETTE IN Hind3 SITE KanR. ALL GENES UNDER PROMOTER/TERMINATOR 35S

ISOLATED DNA THAT ENCODES AN *ARABIDOPSIS THALIANA* MSH3 PROTEIN INVOLVED IN DNA MISMATCH REPAIR AND A METHOD OF MODIFYING THE MISMATCH REPAIR SYSTEM IN A PLANT TRANSFORMED WITH THE ISOLATED DNA

TECHNICAL FIELD

The present invention relates to nucleotide sequences which encode polypeptides involved in the DNA mismatch repair systems of plants, and to the polypeptides encoded by those nucleotide sequences. The invention also relates to nucleotide sequences and polypeptide sequences for use in altering the DNA mismatch repair system in plants. The invention also relates to a process for altering the DNA mismatch repair system of a plant cell, to a process for increasing genetic variations in plants and to processes for obtaining plants having a desired characteristic.

BACKGROUND OF THE INVENTION

Plant breeding essentially relies on and makes use of genetic variation which occurs naturally within and between members of a family, a genus, a species or a subspecies. Another source of genetic variation is the introduction of genes from other organisms which may or may not be related to the host plant.

Allelic loci or non-allelic genes which constitute or contribute to desired quantitative (e.g. growth performance, yield, etc.) or qualitative (e.g. deposition, content and composition of seed storage products; pathogen resistance genes; etc.) traits that are absent, incomplete or inefficient in a species or subspecies of interest are typically introduced by the plant breeder from other species or subspecies, or de novo. This introduction is often done by crossing, provided that the species to be crossed are sexually compatible. Other means of introducing genomes, individual chromosomes or genes into plant cells or plants are well known in the art. They include cell fusion, chemically aided transfection (Schocher et al., 1986. Biotechnology 4: 1093) and ballistic (McCabe et al., 1988, Biotechnology 6: 923), microinjection (Neuhaus et al., 1987, TAG 75: 30), electroporation of protoplasts (Chupeau et al., 1989, Biotechnology 7: 53) or microbial transformation methods such as Agrobacterium mediated transformation (Horsch et al., 1985, Science 227: 1229; Hiei et al., 1996, Biotechnology 14: 745).

However, when a foreign genome, chromosome or gene is introduced into a plant, it will often segregate in subsequent generations from the genome of the recipient plant or plant cell during mitotic and meiotic cell divisions and, in consequence, become lost from the host plant or plant cell into which it had been introduced. Occasionally, however, the introduced genome, chromosome or gene physically combines entirely or in part with the genome, chromosome or gene of the host plant or plant cell in a process which is called recombination.

Recombination involves the exchange of covalent linkages between DNA molecules in regions of identical or similar sequence. It is referred to here as homologous recombination if donor and recipient DNA are identical or nearly identical (at least 99% base sequence identity), and as homeologous recombination if donor and recipient DNA are not identical but are similar (less than 99% base sequence identity).

The ability of two genomes, chromosomes or genes to recombine is known to depend largely on the evolutionary relation between them and thus on the degree of sequence similarity between the two DNA molecules. Whereas homologous recombination is frequently observed during mitosis and meiosis, homeologous recombination is rarely or never seen.

From a breeder's perspective, the limits within which homologous recombination occurs, therefore, define a genetic barrier between species, varieties or lines, in contrast to homologous recombination which can break this barrier. Homeologous recombination is thus of great importance for plant breeding. Accordingly there is a need for a process for enhancing the frequency of homeologous recombination in plants. In particular, there is a need for a process of increasing homeologous recombination to significantly shorten the length of breeding programs by reducing the number of crosses required to obtain an otherwise rare recombination event.

At least in *Escherichia coli*, homologous and homeologous recombination are known to share a common pathway that requires among others the proteins RecA, RecB, RecC. RecD and makes use of the SOS induced RuvA and RuvB, respectively. It has been suggested that mating induced recombination follows the Double-Strand Break Repair model (Szostak et al., 1983, Cell 33, 25–35), which is widely used to describe genetic recombination in eukaryotes. Following the alignment of homologous or homeologous DNA double helices the RecA protein mediates an exchange of a single DNA strand from the donor helix to the aligned recipient DNA helix. The incoming strand screens the recipient helix for sequence complementary, seeking to form a heteroduplex by hydrogen bonding the complementary strand. The displaced homologous or homeologous strand of the recipient helix is guided into the donor helix where it base pairs with its counterpart strand to form a second heteroduplex. The resulting branch point then migrates along the aligned chromosomes thereby elongating and thus stabilising the initial heteroduplexes. Single stranded gaps (if present) are closed by DNA synthesis. The strand cross overs (Holliday junction) are eventually resolved enzymatically to yield the recombination products.

Although in wild type *E. coli* homologous and homeologous recombination are thus mechanistically similar if not identical, homologous recombination in conjugational crosses *E. coli×E. coli* occurs five orders of magnitude more frequently than homeologous recombination in conjugational crosses *E. coli×S. typhimurium* (Matic et al. 1995; Cell 80, 507–515). The imbalance in favour of homologous recombination was shown to be caused largely by the bacterial MisMatch Repair (MMR) system since its inactivation increased the frequency of homeologous recombination in *E. coli* up to 1000 fold (Rayssiguier et al. 1989, Nature 342. 396–401).

In *E. coli*, the MMR system (reviewed by Modrich 1991, Annual Rev Genetics 25, 229–253) is composed of only three proteins known as MutS, MutL and MutH. MutS recognizes and binds to base pair mismatches. MutL then forms a stable complex with mismatch bound MutS. This protein complex now activates the MutH intrinsic single stranded endonuclease which nicks the strand containing the misplaced base and thereby prepares the template for DNA repair enzymes.

During recombination. MMR components inhibit homeologous recombination. In vitro experiments demonstrated that MutS in complex with MutL binds to mismatches at the recombination branch point and physically blocks RecA mediated strand exchange and heteroduplex formation (Worth et al., 1994; PNAS 91, 3238–3241). Interestingly, the SOS dependent RuvAB mediated branch migration is insensitive to MutS/MutL, explaining the observed slight increase in SOS dependent homeologous recombination. Homeologous mating even induces the SOS response, thereby taking advantage of RuvAB induction (Matic et al. 1995, Cell 80, 507–515).

The MMR system thus appears to be a genetic guardian over genome stability in E. coli. In this role it essentially determines the extent to which genetic isolation, that is, speciation, occurs. The diminished sensitivity of the SOS system to MMR, however, allows (within limits) for rapid genomic changes at times of stress, providing the means for fast adaptation to altered environmental conditions and thus contributing to intraspecies genetic variation and species evolution.

The important role of MMR in preserving genomic integrity has been established also in certain eukaryotes. In its efficiency, the human MMR, for example, may even counteract potential gene therapy tools such as triple-helix forming oligonucleotides including RNA-DNA hybrid molecules (Havre et al., 1993, J. Virology 67: 7234–7331; Wang et al., 1995, Mol. Cell. Biol. 15: 1759–1768; Kotani et al., 1996, Mol. Gen. Genetics 250: 626–634; Cole-Strauss et al., 1996, Science 273: 1387–1389). Such oligonucleotides are designed to introduce single base changes into selected DNA target sequences in order to inactivate for example cancer genes or to restore their normal function. The resulting base mismatches however are recognised by the mismatch repair system which then directs removal of the mismatched base, thereby reducing the efficiency of oligonucleotide induced site-specific mutagenesis.

To date, two families of related genes, homologous to the bacterial MutS and MutL genes have been identified or isolated in yeast and mammals (recent reviews by Arnheim and Shibata, 1997, Curr. Opinion Genet. Dev. 7, 364–370; Modrich and Lahue, 1996, Annual Rev. Biochem. 65, 101–133: Umar and Kunkel, 1996, Eur. J. Biochem. 238, 297–307). Biochemical and genetic analysis indicated that eukaryotic MutS homologs (MSH) and MutL homologs (MLH, PMS), respectively, fulfill similar protein functions as their bacterial counterparts. Their relative abundance, however, could reflect different mismatch specificity and/or specialisation for different tissues or organelles or developmental processes such as mitotic versus meiotic recombination.

To date, six different genes homologous to MutS have been isolated in yeast (yMSM), and their homologs have been found in mouse (mMSH) and human (hMSH), respectively. Encoded proteins yMSH2, yMSH3 and yMSH6 appear to be the main MutS homologs involved in MMR during mitosis and meiosis in yeast, where the complementary proteins MSH3 and MSH6 alternatively associate with MSH2 to recognise different mismatch substrates (Masischky et al., 1996, Genes Dev. 10, 407–420). Similar protein interactions have been demonstrated for the human homologs hMSH2, hMSH3 and hMSH6 (Acharya et al., 1996, PNAS 93, 13629–13634).

MutL homologs (MLH and PMS), recently reviewed by Modrich and Lahue (1996, Annual Rev. Biochem. 65, 101–133) have so far been found in yeast (yMLH1 and yPhVS1), mouse (mPMS2) and human (hMLH1, hPMS1 and hpMS2). The hPMS2 is a member of a family of at least 7 genes (Horii et al., 1994, Biochem. Biophys. Res. Commun. 204, 1257–1264) and its gene product is most closely related to yPMS1. Prolla et al. (1994, Science 265, 1091–1093) presented evidence for yPMS1 and yMLH1 to physically associate with each other and, together, to interact with the MutS homolog yMSH2 to form a ternary complex involved in mismatch substrate binding.

However, while medical interest in mismatch repair has prompted extensive research on MMR in bacteria, yeast and mammals, MMR genes have not been isolated from higher plants prior to the present invention and no attempts to adjust the plant MMR to plant breeding needs have been reported.

SUMMARY OF THE INVENTION

According to a first embodiment of the invention, there is provided an isolated and purified DNA molecule comprising a polynucleotide sequence encoding a polypeptide functionally involved in the DNA mismatch repair system of a plant. In one form of this embodiment, the invention provides an isolated and purified DNA molecule comprising a polynucleotide sequence encoding a polypeptide which is homologous to a mismatch repair polypeptide of a yeast or of a human. More particularly, the invention provides polynucleotide sequences encoding polypeptides which are homologous to the mismatch repair polypeptides MSH3 and MSH6 of Saccharomyces cerevisiae. Still, more particularly, the invention provides the coding sequences of the genes AtMSH3 and ArMSH6 of Arabidopsis thaliana, as defined hereinbelow, and polynucleotide sequences encoding polypeptides which are homologous to polypeptides encoded by AtMSH3 and ArMSH6.

According to a second embodiment of the invention, there is provided an isolated and purified polypeptide functionally involved in the DNA mismatch repair system of a plant, for example a polypeptide which is homologous to a mismatch repair polypeptide of a yeast or of a human such as a polypeptide encoded by the genes ArMSH3 or ArMSH6 of Arabidopsis thaliana, as defined hereinbelow.

According to a third embodiment of the invention, there is provided an isolated and purified DNA molecule comprising a polynucleotide sequence selected from the group consisting of (i) a sequence encoding a polynucleotide which is capable of interfering with the expression of a plant polynucleotide sequence encoding a polypeptide which is homologous to a mismatch repair polypeptide of a yeast or of a human and thereby disabling said plant polynucleotide sequence; and (ii) a sequence encoding a polypeptide capable of disrupting the DNA mismatch repair system of a plant.

According to a fourth embodiment of the invention there is provided a chimeric gene comprising a DNA sequence selected from the group consisting of (i) a sequence encoding a polynucleotide which is capable of interfering with the expression of a plant polynucleotide sequence encoding a polypeptide which is homologous to a mismatch repair polypeptide of a yeast or of a human and thereby disabling said plant polynucleotide sequence, and (ii) a sequence encoding a polypeptide capable of disrupting the DNA mismatch repair system of a plant; together with at least one regulation element capable of functioning in a plant cell. Examples of such regulation elements include constitutive, inducible, tissue type specific and cell type specific promoters such as 35S, NOS, PR1a, AoPR1 and DMC1. Typically, a chimeric gene of the fourth embodiment will also include at least one terminator sequence, more typically exactly one terminator sequence.

In the third and fourth embodiments, said interference, by said polynucleotide sequence, with the expression of a plant polynucleotide sequence encoding a polypeptide which is homologous to a mismatch repair peptide of a yeast or a human typically occurs by hybridisation or by co-suppression.

According to a fifth embodiment of the invention there is provided a plasmid or vector comprising a chimeric gene of the fourth embodiment. A vector of the fifth embodiment may be, for example, a viral vector or a bacterial vector.

According to a sixth embodiment of the invention, there is provided a plant cell stably transformed, transfected or electroporated with a plasmid or vector of the fifth embodiment.

According to seventh embodiment of the invention, there is provided a plant comprising a cell of the sixth embodiment.

According to an eighth embodiment of the invention, there is provided a process for at least partially inactivating a DNA mismatch repair system of a plant cell, comprising transforming or transfecting said plant cell with a DNA sequence of the third embodiment or a chimeric gene of the fourth embodiment or a plasmid or vector of the fifth embodiment, and causing said DNA sequence to express said polynucleotide or said polypeptide.

According to a ninth embodiment of the invention, there is provided a process for increasing genetic variation in a plant comprising obtaining a hybrid plant from a first plant and a second plant, or cells thereof, said first and second plants being genetically different; altering the mismatch repair system in said hybrid plant; permitting said hybrid plant to self-fertilise and produce offspring plants; and screening said offspring plants for plants in which homeologous recombination has occurred. For example, homeologous recombination may be evidenced by new genetic linkage of a desired characteristic trait or of a gene which contributes to a desired characteristic trait.

According to a tenth embodiment of the invention there is provided a process for obtaining a plant having a desired characteristic, comprising altering the mismatch repair system in a plant, cell or plurality of cells of a plant which does not have said desired characteristic, permitting mutations to persist in said cells to produce mutated plant cells, deriving plants from said mutated plant cells, and screening said plants for a plant having said desired characteristic.

In a preferred form of the ninth and tenth embodiments of the invention, the step of altering the mismatch repair system comprises introducing into said hybrid plant, plant, cell or cells a chimeric gene of the fourth embodiment and permitting the chimeric gene to express a polynucleotide which is capable of interfering with the expression of a plant polynucleotide sequence in a mismatch repair gene of the hybrid plant, plant, cell or cells, or a polypeptide capable of disrupting the DNA mismatch repair system of the hybrid plant or cells.

In other embodiments, the invention provides (a) an oligonucleotide capable of hybridising at 45° C. under standard PCR conditions to a DNA molecule of the first embodiment; (b) an oligonucleotide capable of hybridising at 45° C. under standard PCR conditions to the DNA of SEQ ID NO: 18 and (c) an oligonucleotide capable of hybridising at 45° C. under standard PCR conditions to the DNA of SEQ ID NO:30; with the proviso that the oligonucleotide of (a), (b) and (c) is other than SEQ ID NO: 1 or SEQ ID NO:2.

BRIEF DESCRIPTION OF THE DRAWINGS

FIG. 4 is a sequence listing of the coding sequence of AtMSH3, together with a deduced sequence of the encoded polypeptide.

FIG. 5 is a protein alignment of yeast *Saccharomyces cerevisiae* and *Arabidopsis thaliana* MSH3 protein. Homologous amino acid residues are highlighted.

FIG. 9 is a sequence listing of the coding sequence of AtMSH6, together with a deduced sequence of the encoded polypeptide.

FIG. 10 is protein alignment of yeast *Saccharomyces cerevisiae* and *Arabidopsis thaliana* MSH6 protein. Homologous amino acid residues are highlighted.

FIG. 11 is a genomic sequence listing of AtMSH6.

DETAILED DESCRIPTION OF THE INVENTION

Figure 1:
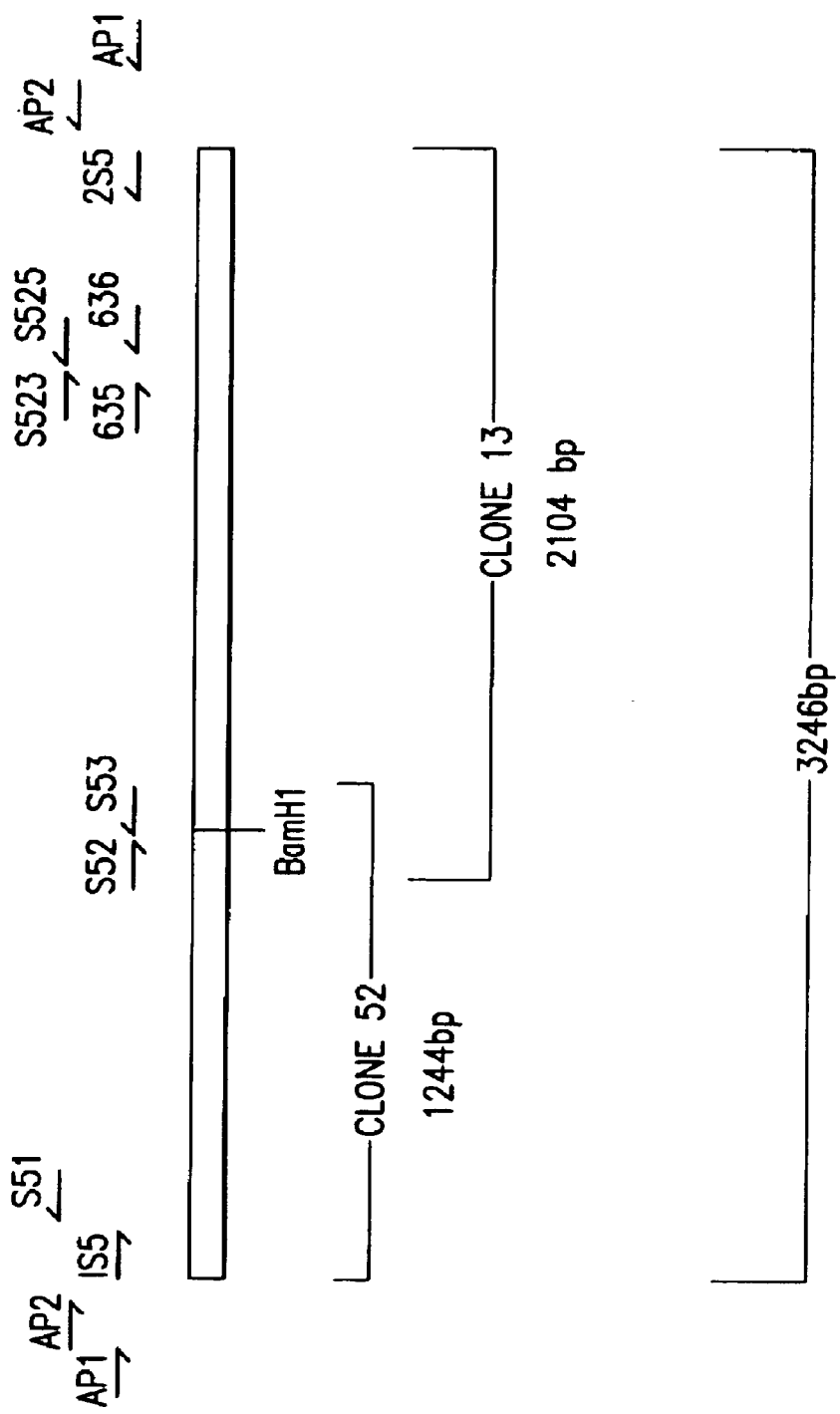
FIG. 1 provides a diagrammatic representation of the primer sequences used to isolate AtMSH3.

The present invention is based on the inventors' discovery that there exist in higher plants genes which are homologous to MMR genes in *E. coli*, and to MMR genes in yeasts and humans.

Thus, the inventors have identified genes, herein designated AtMSH3 and AtMSH6, of the plant *Arabidopsis thaliana* which encode the proteins AtMSH3 and AtMSH6. These plant proteins are homologous to yMSH3 and yMSH6, respectively. The present inventors have isolated cDNAs encoding the proteins AtMSH3 and AtMSH6 and have isolated the complete gene encoding AtMSH6. Given the teaching herein, other genes (for example AtMSH2, and genes of other plants) may be obtained which are involved in DNA mismatch repair in plants, including other genes which encode polypeptides homologous to MMR proteins of yeasts or humans, such as genes which encode polypeptides homologous to yeast MSH2, MLH1 or PMS2, or to human MLH1, PMS1 or PMS2. For example, given the teaching herein, genes of members of the Brassicaceae family or of other unrelated families, for example the Poaueae, the Solanaceae, the Asteraceae, the Malvaceae, the Fabaceae, the Linaceae, the Canabinaceae, the Dauaceae and the Cucurbitaceae family, and which encode polypeptides homologous to MMR proteins of yeasts or humans may be obtained.

Examples of plants whose genes encoding polypeptides homologous to MMR proteins of yeasts or humans may be obtained given the teaching herein include maize, wheat, oats, barley, rice, tomato, potato, tobacco, capsicum, sunflower, lettuce, artichoke, safflower, cotton, okra, beans of many kinds including soybean, peas, melon, squash, cucumber, oilseed rape, broccoli, cauliflower, cabbage, flax, hemp, hops and carrot.

Within the meaning of the present invention, a first polypeptide is defined as homologous to a second polypeptide if the amino acid sequence of the first polypeptide exhibits a similarity of at least 50% on the polypeptide level to the amino acid sequence of the second polypeptide.

A procedure which may be followed to obtain genes AtMSH3 and AtMSH6 is described in Example 1. Essentially the same technique may be applied to obtain other mismatch repair genes of Arabidopsis thaliana, and essentially the same technique as exemplified herein may be applied to cDNA obtained by reverse transcription of RNA from other plants. Alternatively, given the sequence information disclosed herein, other degenerate oligonucleotide primers, especially oligonucleotides of the invention which are capable of hybridising at 45° C. under standard PCR conditions (such as the conditions described in Example 1 using primers UPMU and DOMU) to AtMSH3 and/or ATMSH6 may be designed and obtained for use in isolating sequences of plant mismatch repair genes which are homologous to AtMSH3 or AtMSH6, from other plants. Similarly, oligonucleotides of the invention which are capable of hybridising at 45° C. under standard PCR conditions to plant mismatch repair genes of plants other than Arabidopsis thaliana also fall within the scope of the present invention and may be utilised to obtain mismatch repair genes of still other plants. Typically, such oligonucleotides are capable of hybridising at 45° C. under standard PCR conditions to a DNA molecule which encodes a polypeptide which is homologous to a mismatch repair polypeptide of a yeast or a human. The temperature at which oligonucleotides of the invention hybridise to AtMSH3 and/or AtMSH6, or to plant mismatch repair genes of plants other than Arabidopsis thaliana, or to DNA molecules which encode polypeptides which are homologous to a mismatch repair polypeptide of a yeast or a human may be higher than 45° C., for example at least 50° C., or at least 55° C., or at least 60° C. or as high as 65° C.

The successful gene isolation disclosed herein demonstrates for the first time the existence of MMR in higher plants and indicates the presence of other plant MMR genes. For example, genes encoding the plant homologs of MSH1, MSH2, MSH4, MSH5, PMS1, PMS2 and MLH1 may he identified given the teaching herein. Such genes, as well as those specifically described herein, separately or in combination, are useful in manipulating the plant MMR for plant breeding purposes. Thus, for example, the plant MMR may be altered by including in a plant cell a polynucleotide sequence as defined herein above with reference to the third embodiment of the invention, and causing the polynucleotide sequence to express either a polynucleotide which disables a plant MMR gene, or a polypeptide which disrupts the plant's MMR system.

The DNA molecule of the third embodiment of the invention includes a polynucleotide sequence (herein referred to as a MMR altering gene) which may for example encode sense, antisense or ribozyme molecules characterised by sufficient base sequence similarity or complementarity to the gene to be altered to permit the antisense or ribozyme molecule to hybridise with the plant MMR gene in vivo or to permit the sense molecule to participate in co-suppression. Alternatively, the MMR altering gene may encode a protein or proteins which interfere with the activity of a plant MMR protein and thus disrupt the plant's MMR system. For example, such encoded proteins may be antibodies or other proteins capable of interfering with MMR protein function, such as by complexing with a protein functionally involved in plant MMR thereby disrupting the MMR of the plant. An example of such a protein is the MSH3 protein of Arabidopsis thaliana described herein or a protein of another plant which is homologous to the MSH3 protein of A. thaliana. For instance, overexpression of MSH3 in a plant cell causes MSH2 present in the cell to be substantially completely complexed, disrupting the mismatch repair mechanism or mechanisms in the cell which are functionally dependent on the presence of a complex of MSH2 with MSH6. Similarly, mismatch repair mechanisms which depend on the presence of a complex of MSH2 and MSH3 may be disrupted by the overexpression of MSH6.

A chimeric gene of the fourth embodiment, incorporating a MMR altering gene. may be prepared by methods which are known in the art. Similarly, the MMR altering gene may be introduced into a plant cell, regenerating tissue or whole plant by techniques known in the art as being suitable for plant transformation, or by crossing. Known transformation techniques include Agrobacterium tumefaciens or A. rhizogenes mediated gene transfer, ballistic and chemical methods, and electroporation of protoplasts. The MMR altering gene or genes are typically expressed from suitable promoters. Suitable promoters may direct constitutive expression, such as the 35S or the NOS promoter. Usually, however, the promoter will direct either inducible or tissue specific (e.g. callus; embryonic tissue; etc.), cell type specific (e.g. protoplasts; meiocytes; etc.) or developmental (e.g. embryo) expression of the altering gene or genes, in order for the MMR system to function in tissue types or cell types, or at developmental stages of the plant, in which it is not desirable for the MMR system to be altered. Using such promoters, therefore, the activity of a MMR altering gene may be limited to a specific stage during, plant development or it may be altered by controlling conditions external to 5 the plant, and the deleterious effects of a permanently disabled or altered DNA mismatch repair system in a plant may be avoided. Examples of suitable promoters which are not constitutive are known in the art and include inducible promoters such as PRIa (reviewed by Gatz, 1997, Annual Rev. Plant Phys. Plant Mol. Biol. 48: 89), tissue specific promoters such as AoPR1 (Sabahattin et al., 1993, Biotechnology 11: 218), and cell-type specific promoters such as DMC1.

A chimeric gene in accordance with the invention may further be physically linked to one or more selection markers such as genes which confer phenotypic traits such as herbicide resistance, antibiotic resistance or disease resistance, or which confer some other recognisable trait such as male sterility, male fertility, grain size, colour, growth is rate, flowering time, ripening time, etc.

The process of the tenth embodiment of the invention provides, for example, a process for generating intraspecies genetic variation by altering the mismatch repair system in a plant cell, in regenerating plant tissue or in a whole plant. The plant cell, regenerating tissue or whole plant includes and expresses one or more MMR altering genes which are capable of altering mismatch repair in the plant cell, regenerating tissue or whole plant. Alteration of MMR may be achieved, for example, by inactivating the genes encoding plant MSH3 and/or plant MSH6. It is preferred to inactivate the plant MSH3 and MSH6 encoding genes at the same time and in the same plant cell, regenerating tissue or whole plant. Typically in this preferred form of the invention inactivation of either plant MSH3 or MSH6 alone is insufficient to substantially alter the plant's mismatch repair system and only when both MSH3 and MSH6 are inactivated simultaneously is the plant's mismatch repair system sufficiently altered to prevent the MMR system from recognising base pair mismatches, base insertions or deletions as a result of DNA replication errors, DNA damage, or oligonucleotide induced site-specific mutagenesis. However, in some applications of the invention, inactivation of only one gene may also be used to cause genomic instability or increase the efficiency of site-specific mutagenesis.

If desired, the MMR altering gene or genes may later be rendered non-functional or ineffective, or may be removed from the genome of the plant cell, regenerating tissue or whole plant in order to restore mismatch repair in the plant cell, regenerating tissue or whole plant. The MMR altering gene or genes may be inactivated by means of known gene inactivation tools, such as ribozymes, or may be removed from the genome using gene elimination systems known in the art, such as CRE/LOX. It is preferred to render two genes, whose gene products combine to incapacitate MMR, ineffective by separating the altering genes through segregation. Therefore, in a preferred embodiment of the invention a first plant cell or plant is generated in which only plant MSH3 is incapacitated, and a second plant cell or plant is generated in which only plant MSH6 is incapacitated. The combination of both genomes, for example by crossing, then produces significant MMR deficiency in those cells or plants which have inherited both altering genes. If the altering genes are expressed from unlinked loci, gene segregation restores MMR activity in the progeny of the cells or plants.

In a process of the ninth embodiment of this invention, homeologous recombination is enhanced between different genomes, chromosomes or genes in plant cells or plants by altering MMR in said plant cells or plants. Such genomes, chromosomes or genes are characterised in that they originate from different plant families, genera, species, subspecies, plant varieties or lines. Hybrid plant cells or hybrid plants may be produced by crossing, by cell fusion or by other techniques known in the art. These plant cells or plants are further characterised by expressing one or more genes that are capable of altering mismatch repair in the plant cell or plants.

In the process of the ninth embodiment, the homeologous recombination is typically for the purpose of introducing a desired characteristic in the hybrid plant. In this typical application of the process of the ninth embodiment, and in the process of the tenth embodiment the desired characteristic may be any characteristic which is of value to the plant breeder. Examples of such characteristics are well known in the art and include altered composition or quality of leaf or seed derived storage products (e.g. oil, starch, protein), altered composition or quality of cell walls (e.g. decrease in lignin content), altered growth rate, prolonged flowering, increased plant yield or grain yield, altered plant morphology, resistance to pathogens, tolerance to or improved performance under environmental stresses of various kinds, etc.

In a preferred form of the tenth embodiment, an MMR altering gene is co-introduced along with the homeologous genome, chromosome or gene of another plant cell or plant into an MMR proficient plant cell or MMR proficient plant to produce a hybrid plant cell or hybrid plant in which homeologous recombination can occur. Suitably, the MMR proficient plant cell or MMR proficient plant may also include an MMR altering gene. For example a gene capable of inactivating plant MSH3 may be co-introduced along with the homeologous genome, chromosome or gene of another plant cell or plant into an MMR proficient plant cell or MMR proficient plant in which MSH6 is inactivated. A resultant hybrid plant in which homeologous recombination occurs will include both the MSH3 and MSH6 altering genes and its MMR system will therefore be inactivated.

In this form of the invention, if hybrid plants are to be produced by crossing, the MMR altering gene preferably originates from the male parent, thus ensuring that the MMR altering gene is always introduced and is not present in the recipient cell. That is, the MMR of the recipient cell, prior to introduction of the MMR altering gene, is typically proficient. Alternatively, if an MMR altering gene is present in a recipient cell it may be ineffective or inefficient on its own, or it may be linked to an inducible or tissue specific or cell type specific promoter which only renders the MMR altering gene active under limited conditions.

Thus, in a preferred form of the process of the ninth embodiment, the MMR system of the hybrid plant is initially unaltered. In this form of the process, the step of altering the mismatch repair system may comprise introducing into the hybrid plant, or cells thereof, a MMR altering gene, such as by *Agrobacterium tumefaciens* or *A. rhizogenes* mediated gene transfer, ballistic and chemical methods, and electroporation of protoplasts.

The MMR altering gene or genes are typically expressed from suitable promoters, as described above. Preferably, the promoter is transcriptionally active in mitotically and meiotically active tissue and/or cells to ensure MMR alteration after chromosome pairing at mitosis and meiosis, respectively. The preferred timing for MMR alteration is at meiosis, because recombinant genomes, chromosomes or genes are directly transmitted to the progeny. A suitable meiocyte specific promoter is for example the DMC1 promoter from *Arabidopsis thaliana* ssp. Ler. (Klimyuk and Jones, 1997, Plant J. 11, 1–14). However, mitotic homologous recombination is also a desirable outcome as somatic recombination events can be transmitted to offspring due to the totipotency of plant cells and the lack of predetermined germ cells in plants.

If desired, the MMR altering gene or genes may later be rendered non-functional or ineffective, or may be removed from the hybrid plant or hybrid plant cells, in order to restore mismatch repair in the hybrid plant or hybrid plant cells. The MMR altering gene or genes may be inactivated by means of known gene inactivation tools as described herein above.

EXAMPLES

Example 1

Cloning of the AtMSH3 and AtMSH6 Coding Sequences Isolation of Partial A MSH3 and AtA4SH6 Consensus Sequences Degenerate oligonucleotides UPMU (SEQ ID NO: 1) and DOMU (SEQ ID NO:2)

UPMU CTOGATCCACIGGICCIAA(CIT)ATG

DOMU CTGGATCC(AIG)TA(A/G)TGIGTI(A/G)C(A/G)AA were used to isolate ATMSH3 and AtMSH6 sequences by PCR amplification.

Primers UPMU and DOMU correspond to conserve amino acid sequences of the proteins MutS (*E. coli* and *S. typhimurium*, HexA *S. pneumoniae*, Rep1 (mouse) and Duc1 (human). The concerved regions to which they are targeted are TGPNM (SEQ. ID. NO: 99) for UPMU and FATHY (SEQ ID NO:100) or FVTHY (SEQ. ID. NO. 101) for DOMU. These primers have been used to isolate MSH2 and MSH1 from yeast (Reenan and Kolodner, Genetics 132:963–973 (1992)) and MSH2 from Xenopus and mouse (Varlet et al., Nucleic acids Res. 22:5723–5728 (1994)).

Primers UPMU and DOMU correspond to conserve amino acid sequences of the proteins MutS (*E. coli* and *S. typhimurium*, HexA *S. pneumoniae*, Rep1 (mouse) and Duc1 (human). The concerved regions to which they are targeted are TGPNM (SEQ. ID. NO: 99) for UPMU and FATHY (SEQ ID NO:100) or FVTHY (SEQ. ID. NO. 101) for DOMU. These primers have been used to isolate MSH2 and MSH1 from yeast (Reenan and Kolodner, Genetics 132:963–973 (1992)) and MSH2 from Xenopus and mouse (Varlet et al., Nucleic acids Res. 22:5723–5728 (1994)).

Template single strand cDNA was produced by reverse transcription of 2 μg total RNA from a cell suspension culture of *Arabidopsis thaliana* ecotype Columbia (Axelos et al. 1989, Mol. Gen. Genetics 219: 106–112). The PCR reaction was performed under the following conditions in a final volume of 100 μl: 0.2mM dNTP, 1 μM each primer, IXPCR buffer, 1u Taq DNA polymerase (Appligene) in the presence of template cDNA. PCR parameters were 5 minutes at 94° C., followed by 30 cycles of 40 seconds at 95° C., 90 seconds at 45° C., 1 minute at 72° C. The amplification products were cloned into pGEM-T vector (Promega) and sequenced. Two different clones were isolated, S5 (350 bp) was homologous to MSH3, Sg (327 bp) was homologous to MSH6. Complete cDNA sequences were then isolated according to the Marathon cDNA amplification kit procedure (Clontech). In summary, this procedure involves producing double stranded cDNA by reverse transcription of 2 μg polyA+RNA from the cell suspension culture of Arabidopsis. Adaptors are ligated on each side of the cDNA. The ligated cDNA is used as a template for 5' and 3' RACE PCR reactions in the presence of primers that are specific for the adaptor on one side (AP1 and AP2), and specific for the targeted gene on the other side. A 5' and a fragment that overlap are thus produced for each gene. The complete gene coding sequence can be reconstituted taking advantage of a unique restriction site, if available, in the overlapping region. Specific details of this procedure as it was used to isolate AtMSH3 and AtMSH6 coding regions, are as follows.

Isolation of AtMSH3 Complete Coding Sequence

From the sequence of clone S5, primer 636 (SEQ ID NO:3) was designed:

636 TGCTAGTGCCTCTTGCAAGCTCAT.

Primer AP1 (SEQ ID NO:4) is complementary to a portion of an adaptor sequence which had been ligated to the 5' and 3' ends of Arabidopsis cDNA:

AP1 CCATCCTAATACGACTCACTATAGGGC.

PCR performed on the ligated cDNA with primers 636 and AP1 for the 5' RACE PCR was followed by a second round of amplification with the nested primers AP2 (SEQ ID NO:5) and S525 (SEQ ID NO:6)

AP2 ACTCACTATAGGGCTCGAGCGGC

S525 AGGTTCTGATTATGTGTGACGCTTACTTA (the latter was also designed to correspond to a part of the sequence of clone S5) and produced a 2720 bp DNA fragment. FIG. 1 provides a diagrammatic representation of the primer sequences used to isolate AtMSH3. Another primer (S51, SEQ ID NO:7)

S51 GGATCGGGTACTGGGTTTTGAGTGTGAGG
was designed closer to the 5 border and permitted the determination of 99 bp upstream to the ATG initiation codon. For the 3' RACE PCR, a first PCR reaction was performed with primers AP1 and 635 (SEQ ID NO:8).

635 GCACGTCTTGATGGTGTTTTCAC
followed by a second round of amplification, using the nested primers AP2 and S523 (SEQ ID NO:9)

S523 TCAGACAGTATCCAGCATGGCAGAAGTA
which produced a DNA fragment of 890 bp. Both DNA fragments were subcloned into pGEM-T and sequenced. Since PCR amplification using the Expand Long Template PCR System (Boehringer-Mannheim) produced errors in the sequence, new oligonucleotides were designed to isolate those sequences again by PCR, but with the high fidelity DNA polymerase Pfu. PCR with primers 1S5 (SEQ ID NO: 10) and S53 (SEQ ID NO:11)

1S5 ATCCCGGGATGGGCAAGCAkAAGCAGCA-GACGA

S53 GACAAAGAGCGAAATGAGGCCCCTTGG
amplified the 1244 bp fragment clone 52 (SEQ ID NO: 12, cloned into pUC18/SmaI). PCR with primers S52 (SEQ ID NO: 3) and 2S5 (SEQ ID NO: 14)

2S5 ATCCCGGGTCAAAATGAACAAGTTG-GTTTTAGTC

S52 GCCACATCTGACTGTTCAAGCCCTCGC
amplified the 2104 bp clone 13 (SEQ ID NO:15, cloned into pUC18/SmaI). The complete coding sequence of the AtMSH3 gene was reconstructed in pUC18 by ligating the 5' half AtMSH3 (clone 52) to the 3' half of AtMSH3 (clone 13) after digesting with BamHI which has a unique cleavage site in the overlapping region of both clones. This manipulation yielded plasmid pPF26. The SinaI fragment from pPF26 contains the complete AtMSH3 coding sequence. The remaining primers referred to in FIG. 1 are as follows:

S51 GGATCGGGTACTGGGTTTTGAGTGTGAGG (SEQ ID NO:16)

S525 AGGTTCTGATTATGTGTGACGCTTACTTA (SEQ ID NO: 17)

Figure 2:
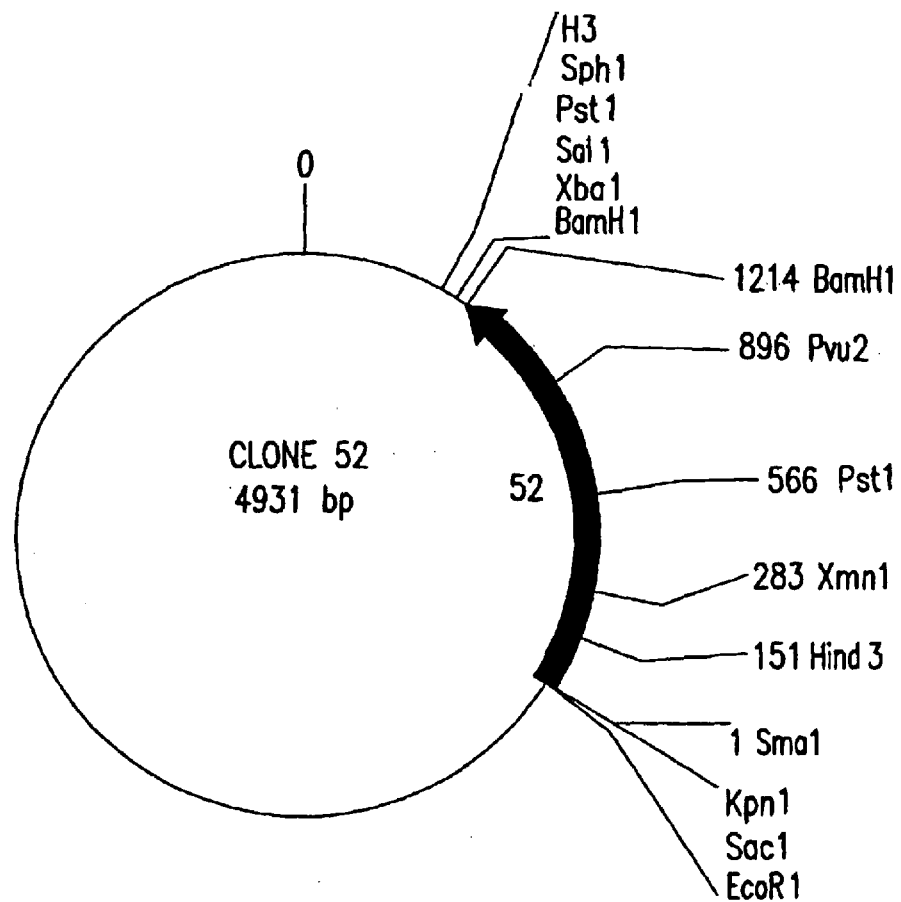
FIG. 2 is a plasmid map of clone 52, showing restriction enzyme cleavage sites in the 5' half of the full-length cDNA for AtMSH3.
Figure 3:
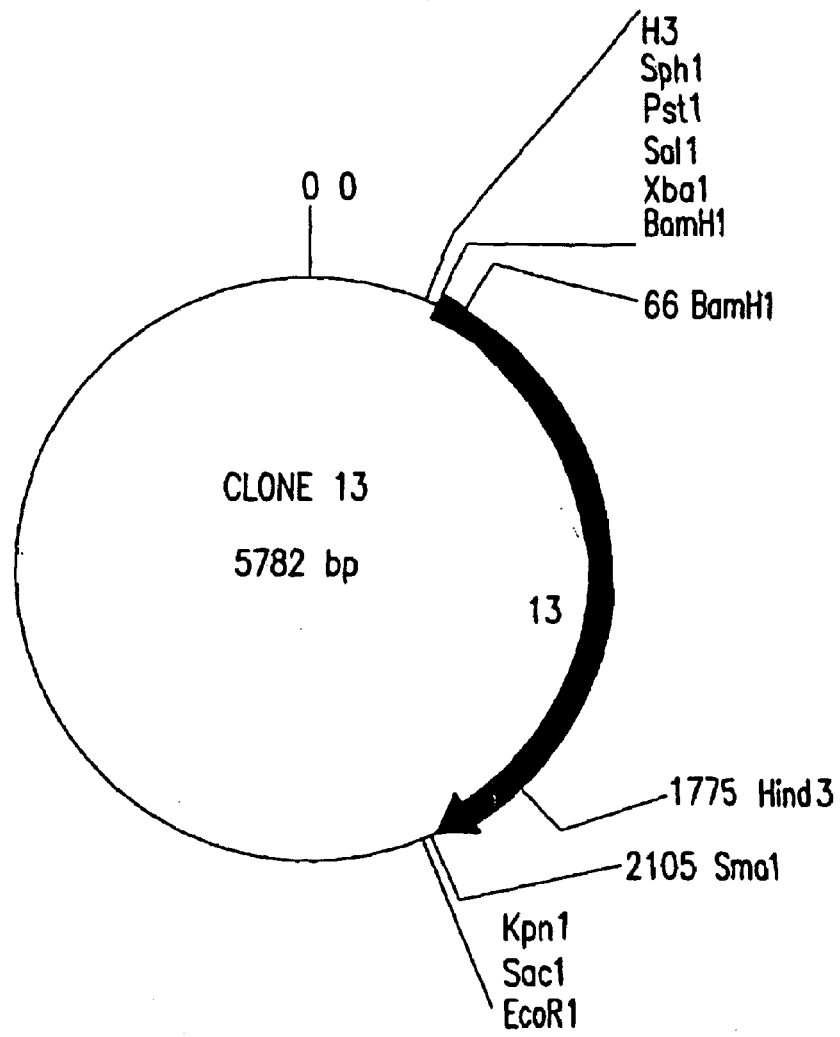
FIG. 3 is a plasmid map of clone 13, showing restriction enzyme cleavage sites in the 3' half of the full-length cDNA for AtMSH3.
Figure 5A:
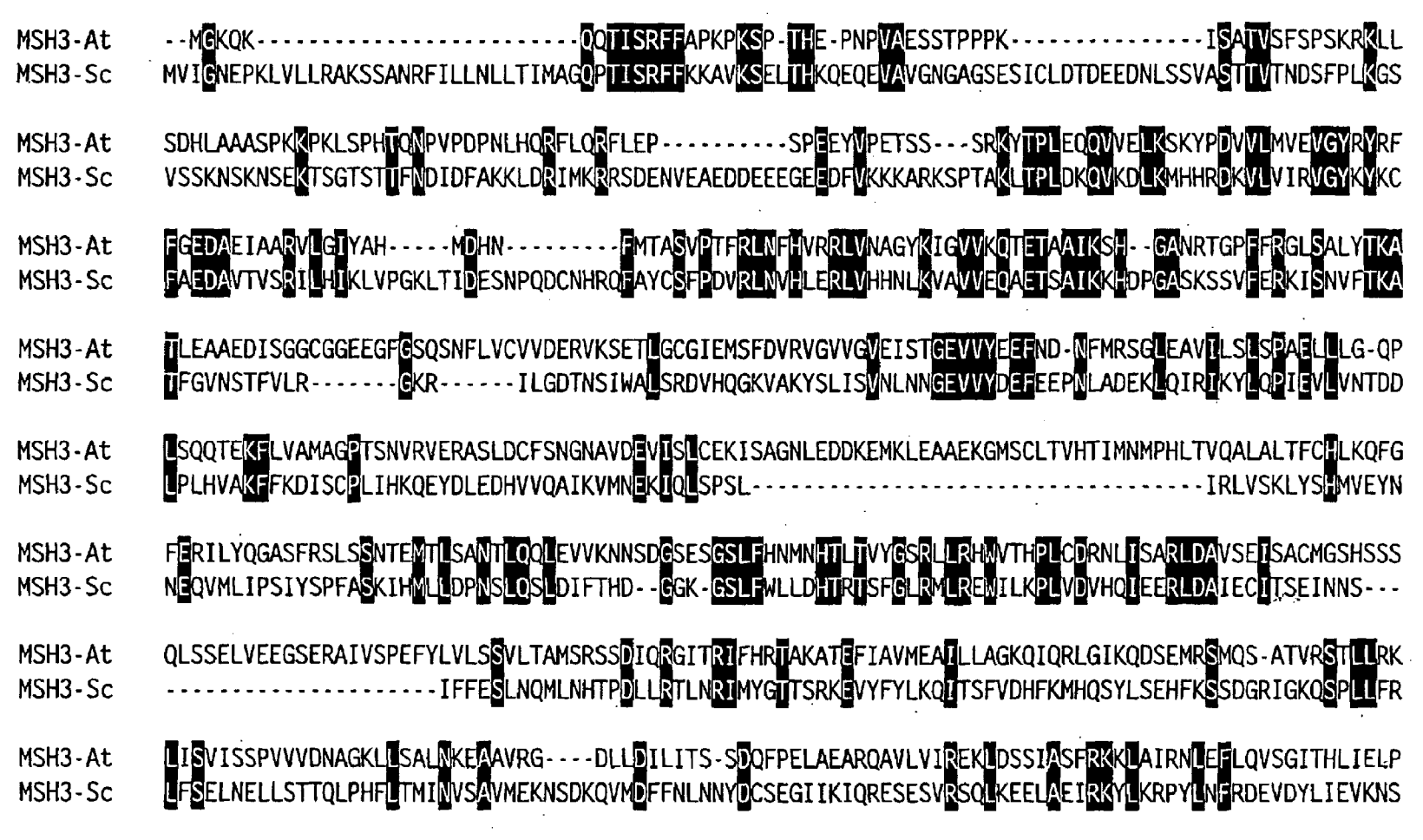

FIGS. 2 and 3 provide plasmid maps of clones 52 and 13 respectively, showing restriction enzyme cleavage sites. The complete AtMSH3 coding sequence (SEQ ID NO: 18) 30 is 3246 bp long and is shown in FIG. 4 together with the deduced sequence (SEQ ID NO: 19) of the encoded polypeptide. AtMSH3 is clearly homologous to the yeast and mouse MSH3 genes. A sequence alignment of polypeptides encoded by AtMSH3 and that encoded by *Saccharomyces cerevisiae* MSH3 is set out in FIG. 5.

Isolation of the AtMSH6 Complete Coding Sequence and Genomic Sequences

Figure 6:
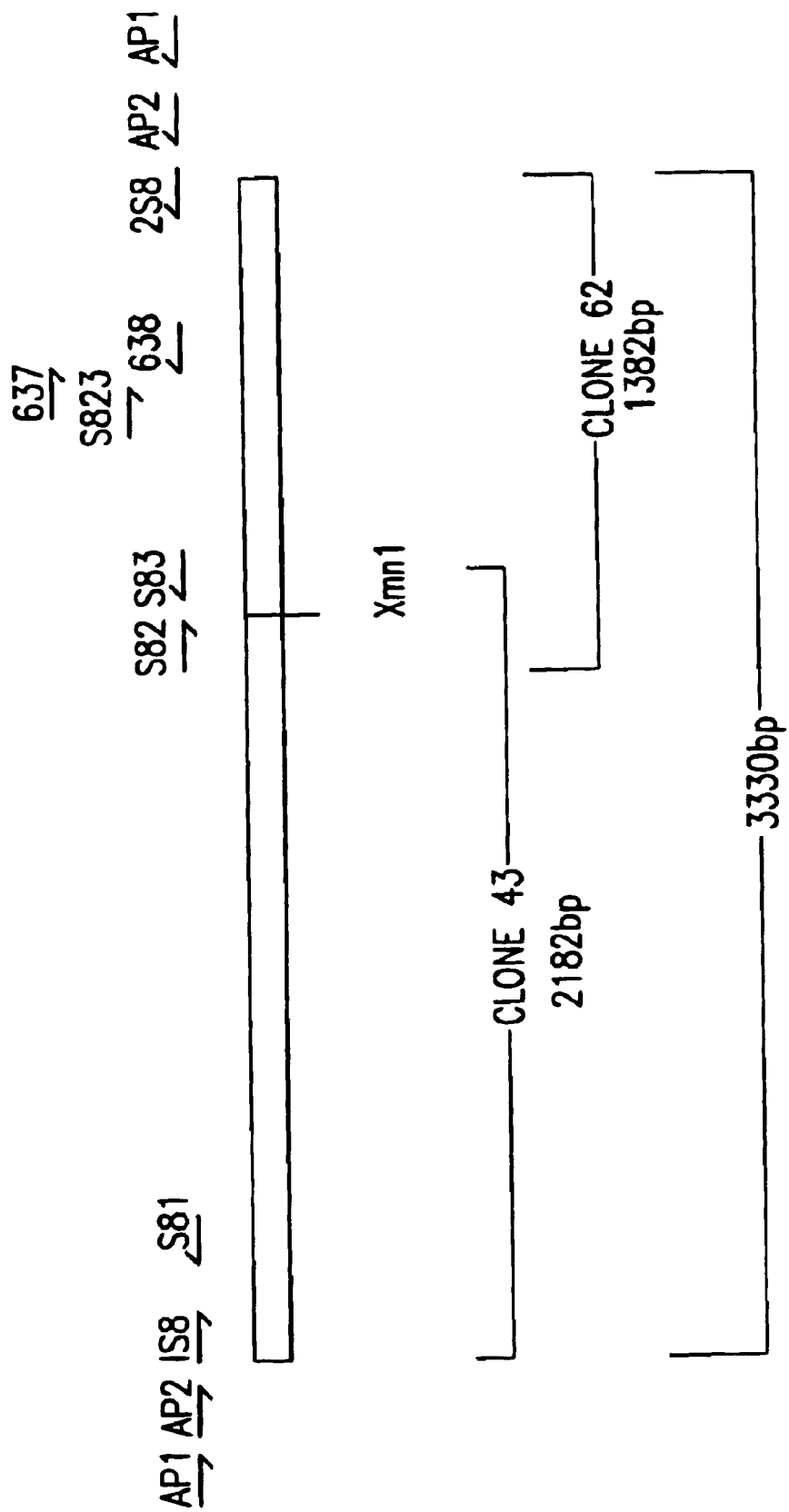
FIG. 6 provides a diagrammatic representation of the primer sequences used to isolate AtMSH6.

The same procedure allowed isolation of the AtMSH6 cDNA. FIG. 6 provides a diagrammatic representation of the primer sequences used to isolate AtMSH6. For the 5' RACE PCR, primers 638 (SEQ ID NO:20) and AP1 (SEQ ID NO:4)

638 TCTCTACCAGGTGACGAAAAACCG
allowed the amplification of a 2889 DNA fragment. Primer S81 (SEQ ID NO:21)

S81CGTCGCCTTTAGCATCCCCTTCC17CAC
helped define the 142 bp upstream to the ATG initiation codon. On the 3' side. RACE PCR was initially performed with primers S823 (SEQ ID NO:22) and AP1 (SEQ ID NO:4).

S823 GCTTGGCGCATCTAATAGAATCATGACAGG
and then with the nested primers 637 (SEQ ID NO:23) and AP2 (SEQ ID NO:5).

637 GACAGCGTCAGTTCTTCAGAATGC
to produce a 774 bp DNA fragment. As for AtMSH3, those fragments were cloned and sequenced. Re-isolation of the DNA sequence using the high fidelity Pfu polymerase and newly designed primers 1S8 (SEQ ID NO:24) and S83 (SEQ ID NO:25) (for the 5' side) led to a 2182 bp DNA fragment identified as clone 43 (SEQ ID NO:26, cloned in pUC18/SmaI), and a 1379 bp clone identified as clone 62 (SEQ ID NO:27, also cloned in pUC18/SmaI).

1S8 ATCCCGGGATGCAGCGCCAGAGATC-GATTTTGT

2S8 ATCCCGGGTTATTTGGGAACACAGTAA-GAGGATT (SEQ ID NO:28)

S82 GCGTTCGATCATCAGCCTCTGTGT7GC (SEQ ID NO:29)

S83 CGCTATCTAFGGCTGCTTCGAATTGAG

Figure 7:
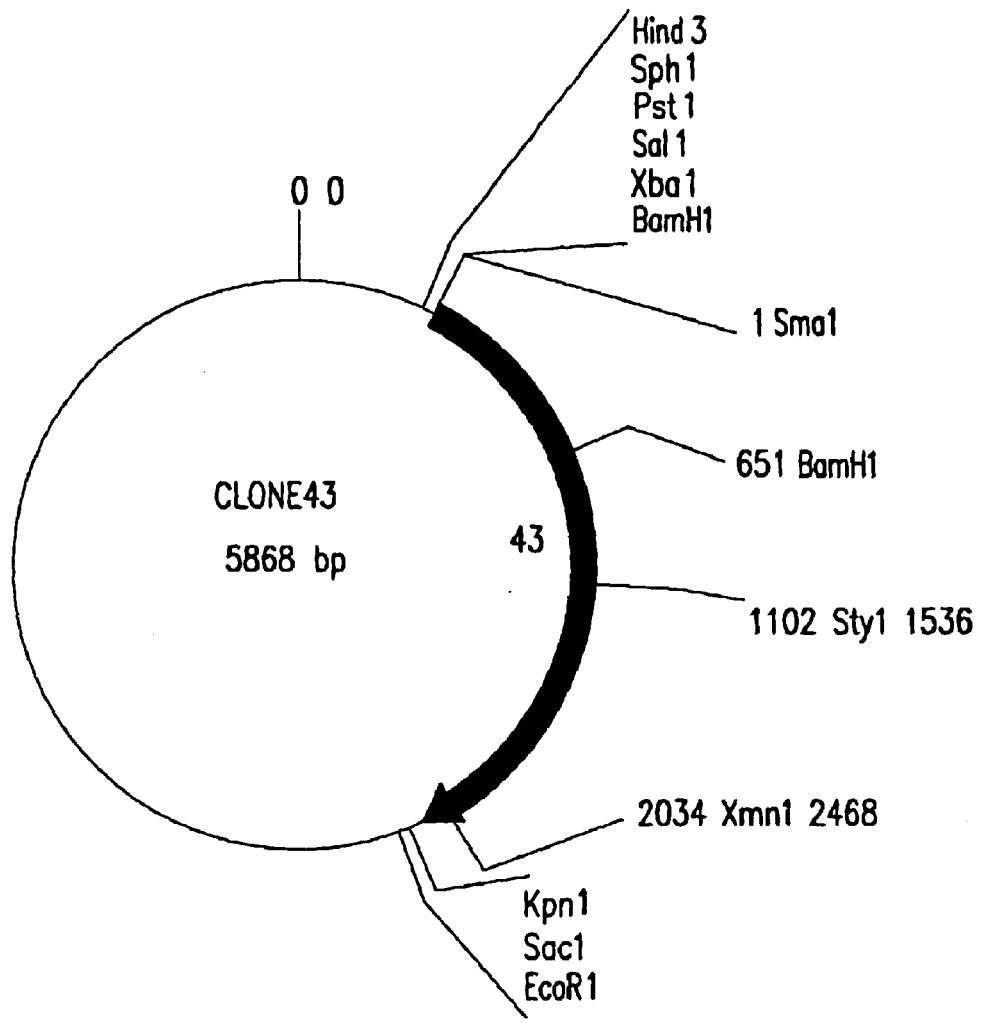
FIG. 7 is a plasmid, map of clone 43, showing restriction enzyme cleavage sites in the 5' half of the full-length cDNA for AtMSH6.
Figure 8:
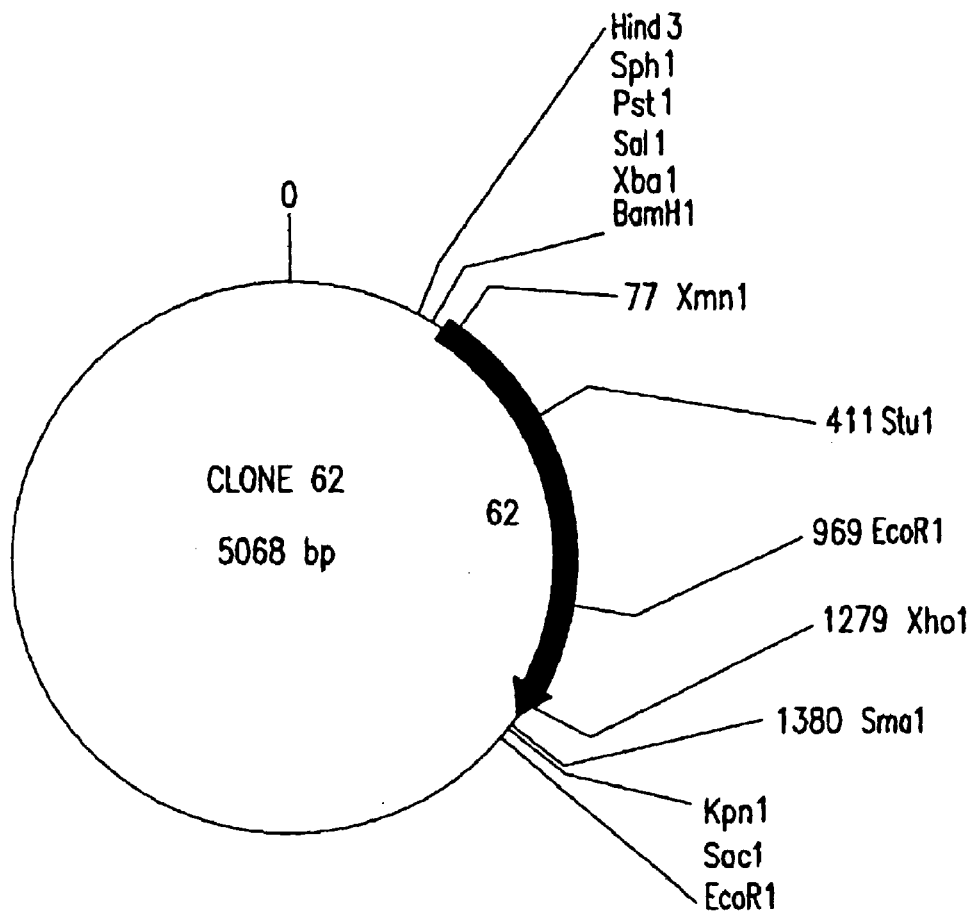
FIG. 8 is a plasmid map of clone 62, showing restriction enzyme cleavage sites in the 3' half of the full-length cDNA for AtMSH6.
Figure 10A:
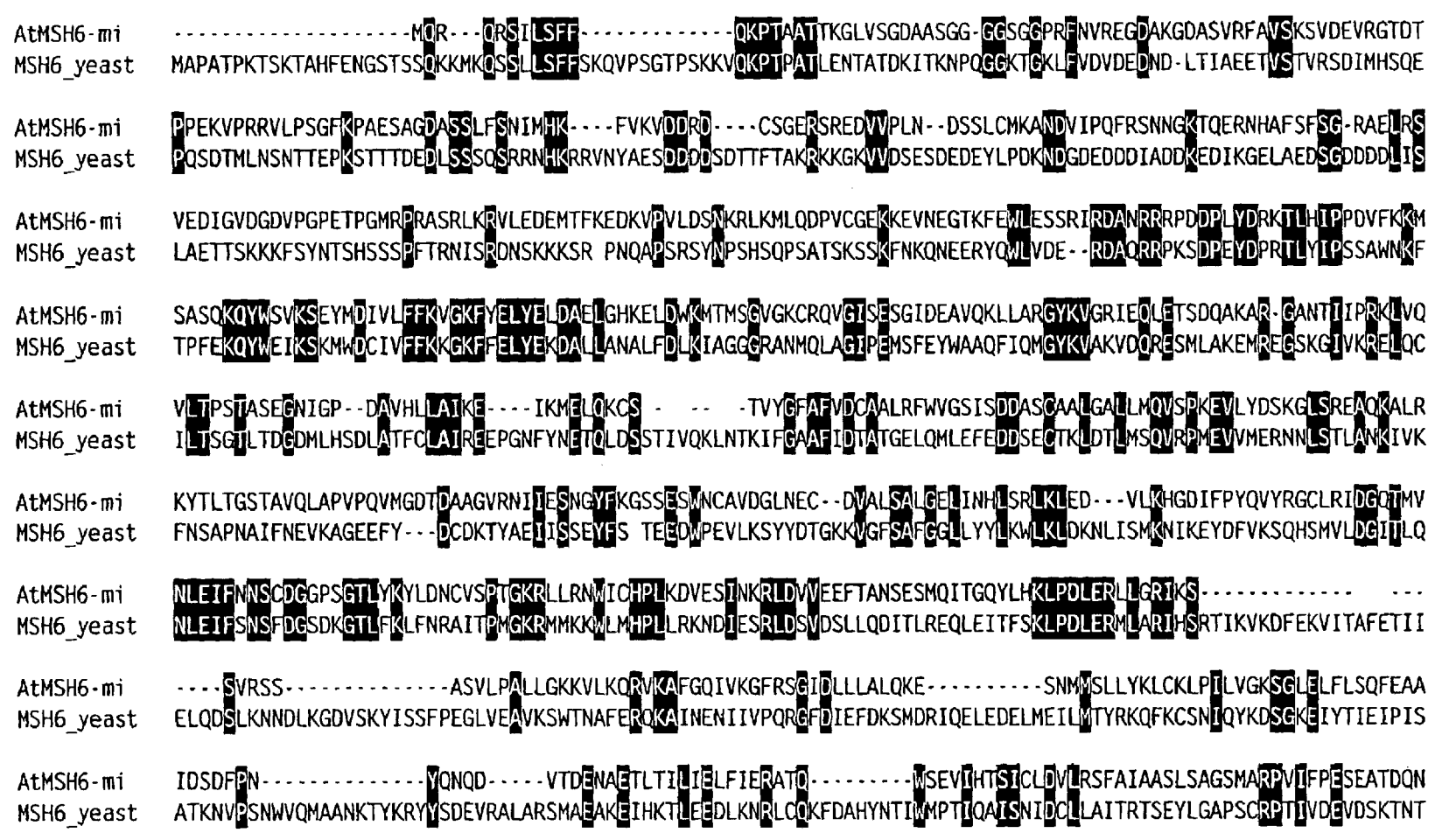
Figure 12:
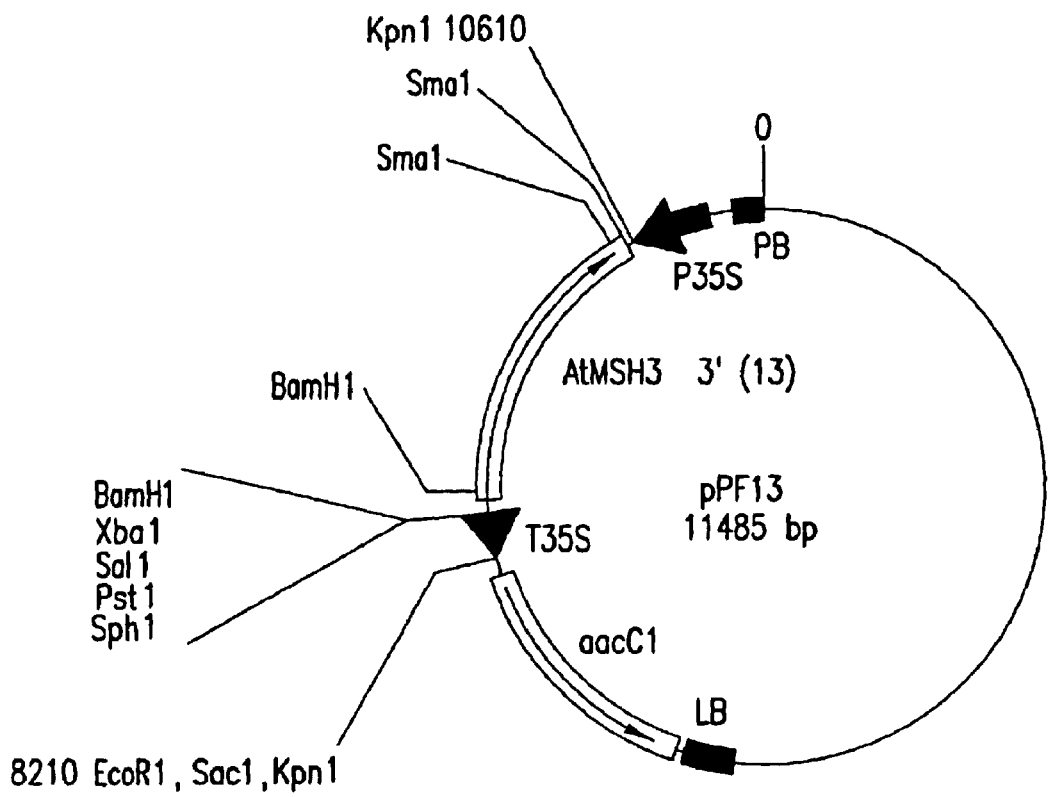
FIG. 12 is a plasmid map of plasmid pPF13.
Figure 13:
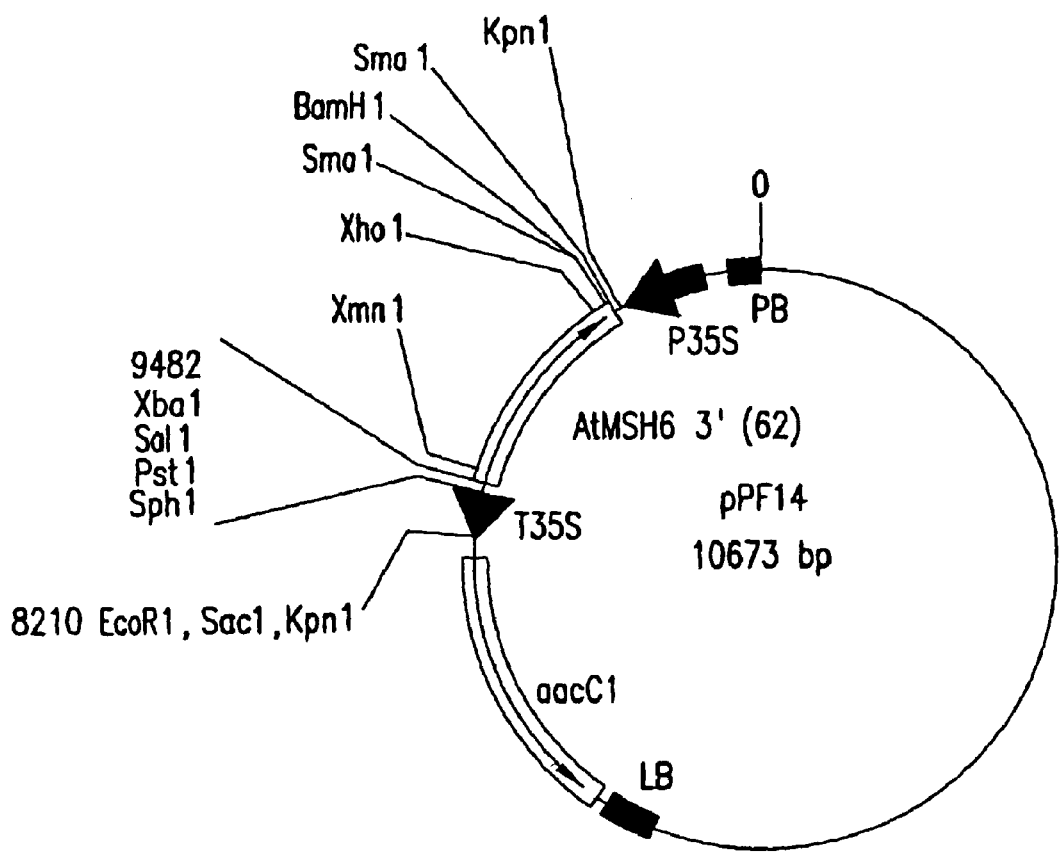
FIG. 13 is a plasmid map of plasmid pPF14.
Figure 14:
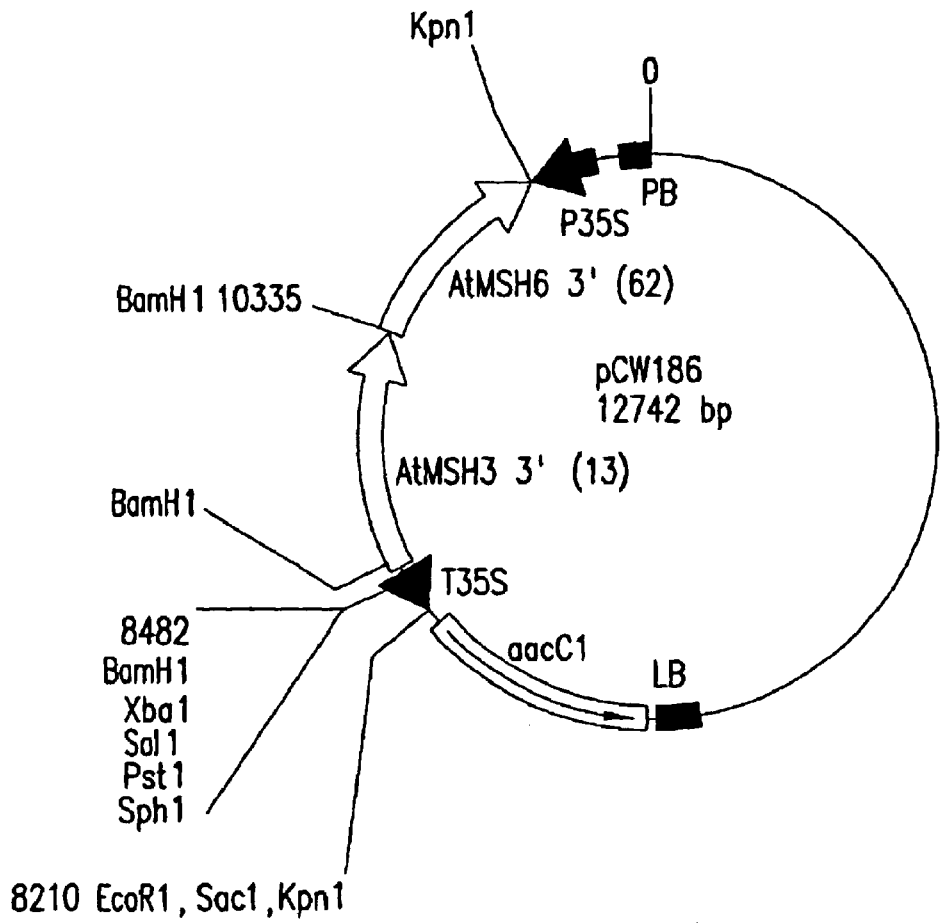
FIG. 14 is a plasmid map of plasmid pCW186.
Figure 15:
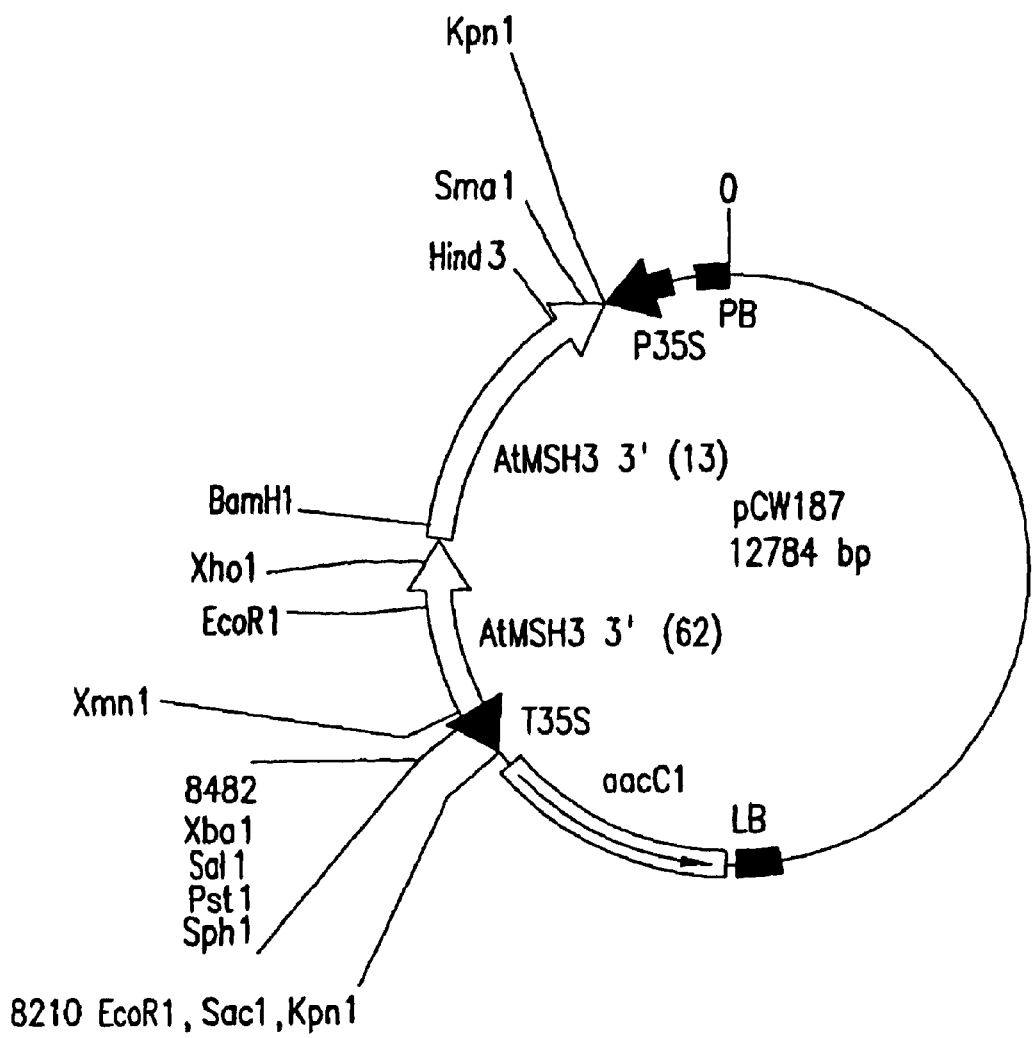
FIG. 15 is a plasmid map of plasmid pCW187.
Figure 16:
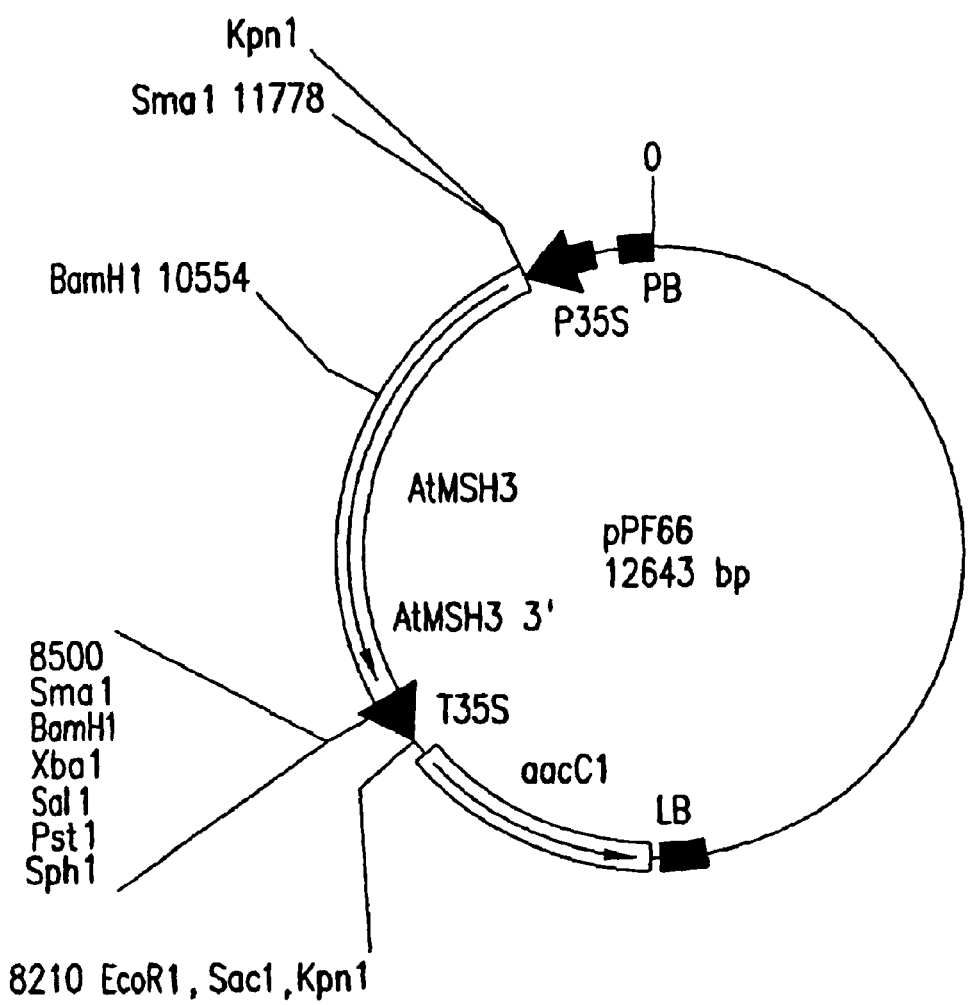
FIG. 16 is a plasmid map of plasmid pPF66.

FIGS. 7 and 8 provide plasmid maps of clones 43 and 62 respectively, showing restriction enzyme cleavage sites. Clones 43 and 62 were digested by the Xmn1 restriction enzyme for which a unique site is present in their overlapping region and then ligated. The complete AtMSH6 coding sequence (SEQ ID NO:30) is 3330 bp long and is shown in FIG. 9 together with the deduced sequence (SEQ ID NO:31) of the encoded polypeptide. AtMSH6 is clearly homologous to the yeast and mouse MSH6genes. A sequence alignment of polypeptides encoded by AtMSH6 and that encoded by *Saccharomyces cerevisiae* MSH6 is set out in FIG. 10.

An AtMSH6 genomic sequence was also isolated from a genomic DNA library constituted after partial Sau3A1 digestion of DNA from the Arabidopsis cell suspension. 8062 bp were sequenced that covered the AtMSH6 gene and show colinearity with the cDNA. 16 introns are found scattered along the gene. The complete genomic sequence (SEQ ID NO:98) is shown in FIG. 11.

EXAMPLE 2

A Measure of Somatic Variation in MMR Deficient Plants Constructs

Constructs with antisense AtMSH3 or antisense AtMSH6 or both AtMSH3/AtMSH6 under the control of a single 35S promoter have been inserted into the binary vector pPZP121 (Hajdukiewicz et al., Plant Mol. Biol. 23. 793–799) between the right and left borders of the T-DNA. The pPZP121 plasmid confers chloramphenicol resistance to *Escherichia coli* or *Agrobacterium tumefaciens* bacteria. The aacC1 gene is carried by the T-DNA and allows selection of transformed plant cells on gentamycin (Hajdukiewicz et al., Plant Mol. Biol. 25, 989–994). For the purpose of expressing antisense constructs, a 35S promoter/terminator cassette with a polylinker was introduced into pPZP121. The 3' ends of the considered genes have been chosen since this region seems more efficient for antisense inhibition. For AtMSH3 this corresponds to clone 13 (2104 bp), for AtMSH6 this corresponds to clone 62 (1379 bp). Clone 13 comprises 2104 bp of the 3' region that were cut off the pUC18 vector by SalI/SstI restriction, blunted with T4 DNA polymerase and ligated into the T4 DNA polymerase blunted BamHI site of pPZP121/35S, creating clone pPF13. The same procedure was followed for the 3' region of AtMSH6 clone 62 (1379 bp) thus creating plasmid pPF14. For the double constructs, the 3' region (from clone 62) of AtMSH6 was introduced ahead of the AtMSM3 region into pPF13 creating pCW186 and to reciprocally, the 3' region of AtMSH3 (from clone 13) was introduced ahead of AtMSH6 into pPF14, creating pCW187.

These constructs were introduced into the Arabidopsis cells (as described below) of wildtype Columbia and of the Columbia tester line.

An alternative strategy to antisense inhibition of AtMSH6 comes from experiments of Marra et al. (1998. Proc. Natl. Acad. Sci USA 95. 8568–8573) who show that overexpression of functional MSH3 results in depiction of MSH6 protein in human cells. This depletion may generate a mismatch repair mutant phenotype.

For the purpose of overexpressing functional AtMSH3 protein in plant cells, the complete MSH3 coding region was excised from pPF26 (example 1) by digestion with SmaI, and was inserted into the SmaI site of pCW164. The resulting construct was named pPF66. It contains a complete AtMSH3 gene under the control of the 35S promoter inside the left (LB) and right (RB) border of the T-DNA. This T-DNA also contains the hpt2 gene for gentamycin selection. Plasmid pPF66 was introduced into Arabidopsis cells as described below. One cell clone was selected which clearly overexpressed the AtMSH3 gene as shown by Northern analysis. FIGS. 12–16 provide plasmid maps of plasmids pPF13, pPF14, pCW186, pCW187 and pPF66, respectively.

Construction of Tester Construct

For the purpose of Forward Mutagenesis Assays, a tester construct was built containing the coding regions for nptII, codA, uidA. All three genes are driven by the 35S promoter and are terminated by the 35S terminator. This construct was obtained by introducing an EcoRI fragment encoding the codA cassette (2.5 kb) and a HindIII fragment encoding the uidA (GUS) cassette (2.4 kb) into the pPZP111 vector (Hajdukiewicz et al.,1994, Plant Mol Biol 23: 793–799) which already contained the nptII expression cassette. This new plasmid was named pPF57. NptII is used to select for transformed plant cells. GUS is used to analyse the degree of gene silencing in the construct (i.e. to identify cell lines in which the transgenes are expressed), and codA is used as a marker for forward mutagenesis (described below).

Figure 17:
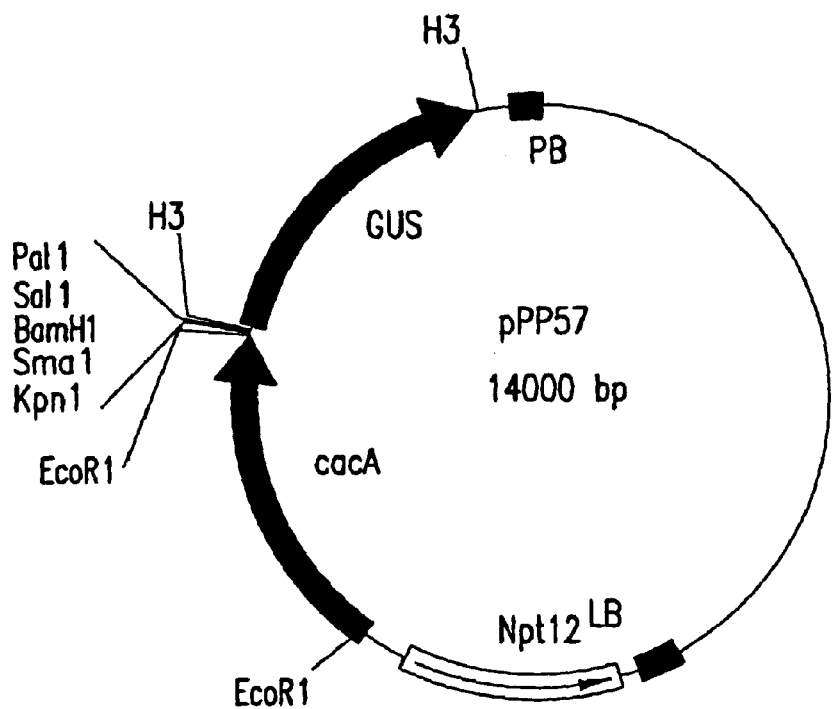
FIG. 17 is a plasmid map of plasmid pPF57.

The plasmid map of pPF57 is provided in FIG. 17.

Plant Cell Transformation

The constructs are introduced into Agrobacterium by electroporation. Plant cells are then transformed by co-cultivation. A suspension culture of *Arabidopsis thaliana* cells that has been established be Axelos et al. (1992, Plant Physiol. Biochem. 30, 1–6) may be used. One day old freshly subcultured cells are diluted five times into AT medium (Gamborg B5 medium. 30 g/l sucrose, 200 µg/l NAA). 10 µl of saturated Agrobacterium containing the transforming T-DNA constructs are added to 10 ml diluted cells in a 100 ml erlenmeyer. The co-cultivation is agitated slowly (80 rpm) for 2 days. The cells are then washed 3 times into AT medium and finally resuspended in the same initial volume (10 ml). The culture is agitated for 3 days to allow expression before plating on selection plates (AT/BactoAgar 8g/l+gentamycin 50 µg/ml). Transformed individual calli are isolated 3 weeks later.

Tester Strain

The tester construct on plasmid pPF57 was introduced into Arabidopsis cells of wildtype Columbia using the transformation protocol described above. Among 10 candidate transformants, one cell clone was shown (by Southern analysis) to have a unique T-DNA insertion. All three genes were shown to be functional in this cell line as indicated by resistance to kanamycin, blue staining in the presence of X-Glu (GUS), and sensitivity to 5-fluoro-cytosine (codA).

MMR altering genes (described above) were then introduced individually into the tester line and transformed cells are used for analysis of both Microsatellite Instability and Forward Mutagenesis.

Microsatellite Analysis

Microsatellites have been described in Arabidopsis (Bell and Ecker. 1994, Genomics 19. 137–144). The present Example is based on a study of instability of microsatellites that are polymorphic amongst different ecotypes. DNA is extracted from the transformed calli. Specific primers have been defined that are used to amplify the microsatellite sequence. One of the two primers is previously $p^{32}$ labelled by T4 kinase. In case of a polymorphic variation, new PCR products appear that do not follow the expected pattern of migration on a polyacrylamide gel. This is a commonly observed feature for MMR deficient cells in yeast or mammalian cells.

In particular, the present Example describes a study on microsatellites ca72 ($CA_{18}$), nga172 ($GA_{29}$), and ATHGENEA($A_{39}$), chosen because they belong to the types predominantly affected in human mismatch repair deficient tumors. The size of these microsatellites is not conserved from one Arabidopsis ecotype to the other.

Arabidopsis cells which are transformed with an MMR altering gene (above) and control cells not expressing the MMR altering gene are allowed to form calli. DNA is rapidly extracted from the calli and is analysed for microsatellite instability as described in detail by Bell and Ecker 1994. Genomics 19, 137–144. In summary, the relevant microsatellite is amplified by PCR using P32 labelled primers. The PCR products are separated on a DNA sequencing gel for size determination. Size differences between microsatellites from transformed and control cells not expressing the MMR altering gene in question indicate microsatellite instability as a result of MMR alteration.

The sequences of primers used for PCR amplification of microsatellites ca72 and nga172 are included in Table 1. PCR amplification of microsatellite ATHGENEA made use of a forward primer containing the sequence ACCATGCATAGCTTAAACTTCTTG (SEQ ID NO:32) and of a reverse primer containing the sequence

ACATAACCACAAATAGGGGTGC (SEQ ID NO:33).

The amplification for microsatellite ca72 revealed in Columbia control cells (with respect to the MMR altering gene) a 248 bp long PCR fragment instead of the published length of 124 bp. DNA sequencing verified this fragment as a $CA_{18}$ microsatellite.

Forward Mutagenesis Assay

Tester cells transformed with antisense AtMSH3 or antisense AtMSH6 or both AtMSH3/AtMSH6 are analysed for the stability of the codA gene. The functional codA gene confers to sensitivity to 5-fluoro-cytosine (5FC), whereas a gene inactivating mutation in codA will confer resistance to 5FC. The frequency of resistant cells is therefore a good indicator of somatic variation as a direct result of MMR alteration. Variants resistant to 5FC are first analysed for GUS activity. If GUS is inactive, 5FC resistance is assumed to be due to gene silencing (all three genes are under The 35S promoter). If GUS is active. 5FC resistance is assumed to be due to forward mutations that have inactivated codA. PCR is then performed on the putative codA mutant genes which is then sequenced to confirm the presence of forward mutations in codA.

Besides codA, other marker genes may also be used for the Forward Mutagenesis Assay such as the ALS gene (conferring sensitivity to valine or to sulfonylurea; Hervieu and f Vaucheret, 1996, Mol. Gen. Genet. 251 220–224: Mazur et al. 1987, Plant Physiol. 85 1110–1117).

EXAMPLE 3

Homeologous Meiotic Recombination in *Arabidopsis thaliana*

A. Construction of a Meiocyte Specific Gene Expression Cassette Comprising the DMC1 Promoter and the NOS Terminator (i) The DMC1 promoter may be used as published by Klimyuk and Jones, 1997, Plant J. 11.1–14). To obtain a more convenient alternative for gene cloning, a 3.3 Kb long subfragment of the DMC1 promoter was obtained by PCR from genomic DNA of *Arabidopsis thaliana* (ssp. Landsberg erects "Ler").

The PCR was done in three rounds:

Round One: A 3.7 Kb long product was obtained using the forward primer DMCIN-A comprising the sequence GAAGCGATATTGTTCGTG (SEQ ID NO:34) and the reverse primer DMCIN-B comprising the sequence

AGATTGCGAGAACATTCC (SEQ ID NO:35).

The weak amplification product was then used as template for round two and three.

Round Two: A 3.1 Kb long product comprising the promoter and the 5' untranslated leader was obtained using forward primer DMCIN-1, which contained the sequence acgcgtcgacTCAGCTATGAGATTACTCGTG (SEQ ID NO:36) and introduced a SalI cloning site at the 5' end of the promoter fragment, and reverse primer DMCIN-2 which contained the sequence gctctagaTTTCTCGCTCTAAGACTCTCT (SEQ ID NO:37) and introduced a XbaI site at the 3' end of the PCR fragment.

Round Three: A 0.2 Kb long product comprising the first exon/intron of the DMC1 promoter was obtained using forward primer DMCIN-3, which contained the sequence gctctagaGCTTCTCTTAAGTAAGTGATTGAT (SEQ ID NO:38) and introduced a XbaI site at the 5' end of the PCR fragment, and reverse primer DMCIN4, containing the sequence tccccggggctcgagagatctccategTTTCTT CAGCTC-TATGAATCC (SEQ ID NO:39) and introduced at the 3' end of the PCR product restriction sites for NcoI, BgIII, XhoI and SmaI.

The products obtained in round Two and Three were digested with XbaI and subsequently ligated to reconstitute a 3.3 Kb lone DMC1 promoter from which the first two in-frame ATG start codons were replaced with a unique restriction site for XbaI. This promoter can be cloned between the restriction sites for SalI and SmaI of p3264, which contains the SacI-EcoRI NOS terminator in pBIN19, to yield the entire expression cassette in pBIN19. This cassette contains the following cloning sites: NcoI, BgIII XhoI. SmaI and (already present on p3264) KpnI and SacI.

(ii) Another strategy yielded the following convenient DMC1 promoter. A 1.8 kb DNA fragment comprising the 3' terminal pan of the meiocyte specific DMC1 promoter was isolated by PCR from purified genomic DNA of *Arabidopsis thaliana* (ssp. Landsberg erecta "Ler"). The forward PCR primer (DMC1a) contained the sequence acgcgtcgacGAATTCGCAAGTGGGG (SEQ ID NO:40)

and introduced a SalI cloning site at the 5' end of the promoter fragment. The reverse PCR primer (DMC1b) contained the sequence tccatggagatctcccgggtacCGATTTGCTTCGAGGG (SEQ ID NO:41)

introducing a polylinker region at the 3' end of the promoter fragment. The PCR reaction was carried out with VENT DNA Polymerase (NEB) over 25 cycles using the following cycling protocol: 1 minute at 94° C., 1 minute at 54° C., 2 minutes at 72° C.

The PCR reaction yielded a blunt ended DNA fragment which was digested with restriction enzyme SalI and was cloned into the cleavage sites of restriction enzymes SalI and SmaI in plasmid p2030, a pUC118 derivative containing the SacI-EcoRI NOS terminator fragment of pBIN121. The cloning yielded plasmid p2031, containing the DMC1 promoter-polylinker-NOS terminator expression cassette depicted in FIG. 18.

Figure 18:
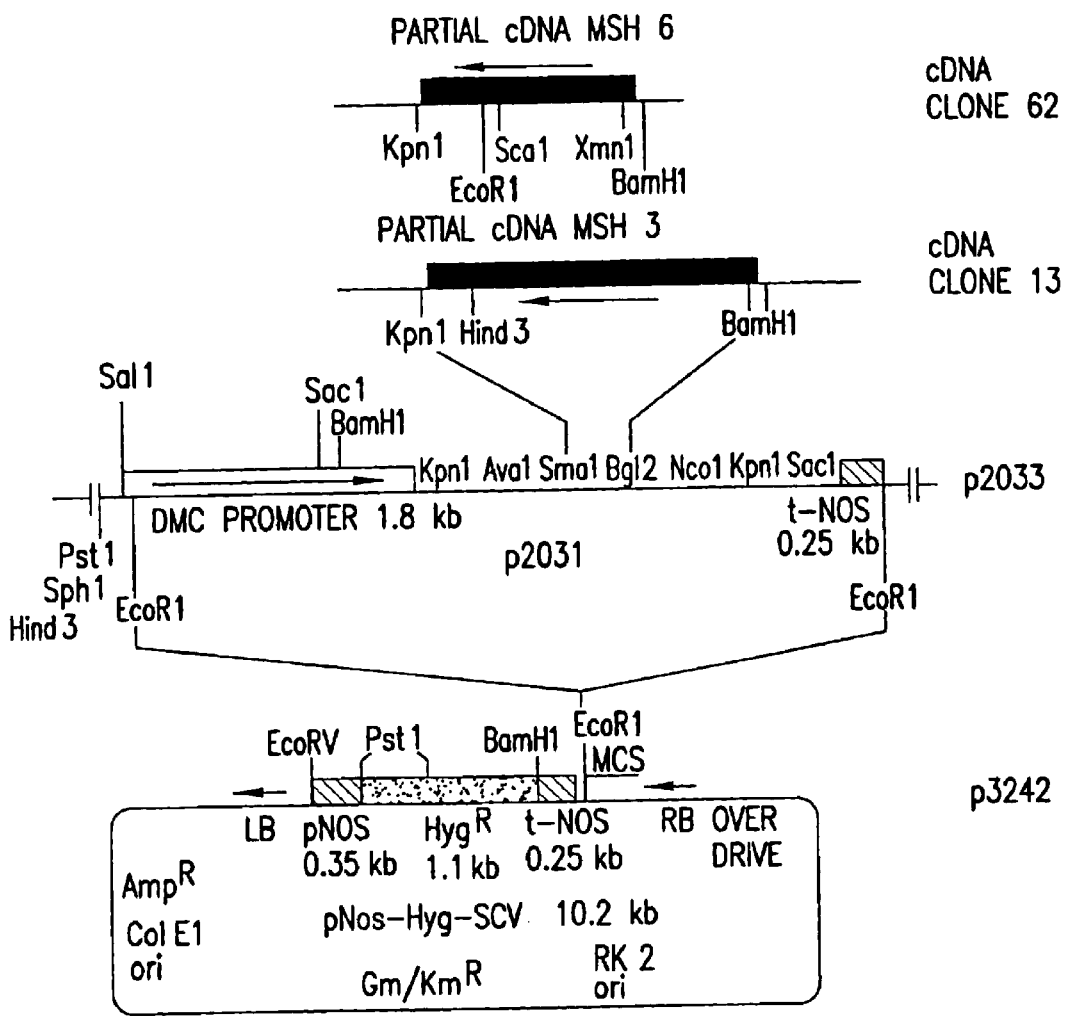
FIG. 18 is a diagrammatic representation of an antisense gene construction for use in homeologous meiotic recombination.

B. Construction of an MSH3 Antisense Gene Under the Control of the DMC1 Promoter A 2.1 kb DNA fragment encoding the carboxyterminal part of AtMSH3 was removed from the polylinker of clone 13 described in Example 1 after (i) digestion with KpnI, (ii) blunting of the DNA ends generated by KpnI and (iii) digestion with BamHI. The isolated fragment was then cloned in antisense orientation downstream of the DMC1 promoter in plasmid p2031, which had, been digested with restriction enzymes SmaI and Bg/II. This cloning yielded plasmid p2033 (FIG. 18).

After digestion of p2033 with EcoRI , a 4.1 kb DNA fragment was recovered comprising the DMC1 promoter, the partial MSH3 cDNA in antisense orientation with respect to the promoter and the NOS terminator. This fragment was cloned into the EcoRI restriction site of plant transformation vector pNOS-Hyg-SCV to yield plasmid p3242 (FIG. 18).

Figure 19:
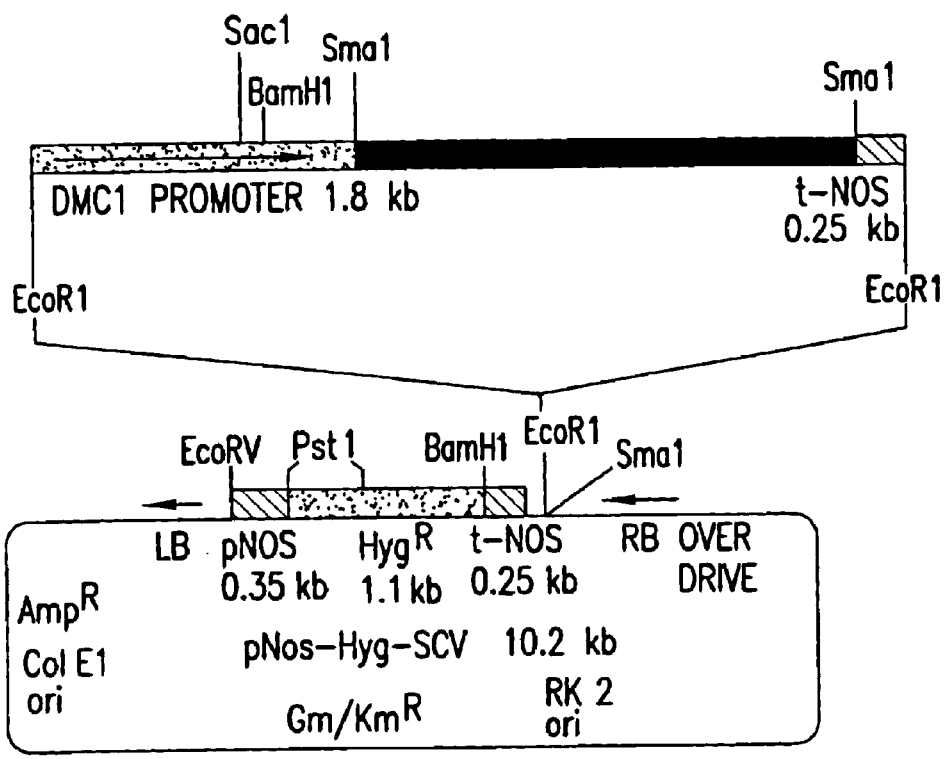
FIG. 19 is a plasmid map of plasmid p3243.

C. Construction of a Combined MSH61MSH3 Antisense Gene Under the Control of a Single DMC1 Promoter A 3.1 kb fragment, encoding in antisense orientation the partial AtMSH6 and AtMSH3 sequences and the 35S terminator, was isolated from pCW186 by digestion with KpnI. The fragment was treated with Klenow enzyme to blunt both ends. It was then cloned into the SmaI site of plasmid p3243 (a pNOS-Hyg-SCV derivative, illustrated in FIG. 19), which had been opened to delete the region between the SmaI sites. Clones containing the fragment in the antisense orientation with respect to the DMC1 promoter (described in A(ii) above) were identified by diagnostic digestion with BamHI. The selected construct was named p3261.

Another practical way of cloning the double antisense gene is as follows. A 1 kb DNA fragment encoding the carboxyterminal part of AtMSH6 is isolated from clone 62 described in Example 1 after digestion of clone 62 plasmid DNA with BamHI, which cleaves in the 5' polylinker region flanking the partial cDNA, and with EcoRI, which cleaves within the cDNA. The isolated fragment is treated with Klenow enzyme to blunt both its ends and is cloned into the recipient plasmid p2033 or p3242. For the purpose of cloning, the recipient plasmid may be cleaved with either AvaI or NcoI and can be blunted with Klenow enzyme to produce blunt acceptor ends for fragment cloning. This cloning yields, two opposite orientations of cloned fragment DNA with respect to the DMC1 promoter. These can be identified by diagnostic digestion with restriction enzymes ScaI or XmnI in conjunction with SacI. The selected construct contains the DMC1 promoter, the combined partial cDNAs for AtMSH3 and AtMSH6 (both cloned in antisense orientation with respect to the DMC1 promoter) and the NOS terminator. If the recipient plasmid is p2033, the combined antisense gene under control the single DMC1 promoter is recovered from the vector after EcoRI digestion and is cloned into the EcoRI restriction site of pNOS-Hyg-SCV.

D. Construction of a full-length MSH3 Sense Gene Under Control of the DMC1 Promoter for Overexpression of Functional MSH3 Protein Overexpression of MSH3 protein was shown in human cells (Marra et al., 1998, Proc. Natl. Acad. Sci. USA 95, 8568–8573) to complex all available MSH2 protein. This leaves MSH6 protein without its partner, leading to the degradation of MSH6 protein and eventually to a mismatch repair phenotype.

This phenomenon is exploited to increase homeologous meiotic recombination in Arabidopsis as an alternative to antisense inhibition of AtMSH6. For this purpose the full-length cDNA encoding AtMSM3 is isolated from plasmid pPF66 by digestion with SmaI and is cloned into the SmaI site of the DMC1 expression cassettes described in A(i).

E. Selection of Recombination Markers on Homeologous Chromosomes of ArabidoDsis thaliana Subspecies Landshere Erecta (Lerl. Columbia (Col) and C24, Respectively E(i). Visual Recombination Markers in Arabidopsis th. subspecies C24:

Agrobacterium mediated transformation with a T-DNA containing a 35S-GUS gene, inactivated by insertion of a 35S-Ac transposable element (Finnegan et al., 1993, Plant Mol. Biol. 22, 625–633), had yielded a C24 line in which the T-DNA construct was integrated into chromosome 2. Genetic and molecular analysis of this line shows that the Ac transposon had excised from its T-DNA locus thereby restoring GUS activity, but had re-inserted into the chromosome at a distance of 16.4 cM, where it stayed fixed (due to disablement of Ac) within the chlorina gene. Insertional inactivation of the chlorina gene caused a bleached phenotype in those plants that were homozygous for this mutation. Because of the two linked phenotypic markers, chlorina3A:Ac and GUS, this C24 line was used in crosses to wildtype Ler for analysis of meiotic homeologous recombination on chromosome 2 in conjunction with molecular recombination markers.

E(ii). Visual Recombination Markers in Arabidosis th. Ler

The Ler line NW1 (obtained from NASC, Nottingham, UK) contains one recessive visual marker per chromosome, i.e. an-1 on Chr.1, py-1 on Chr.2, gl1-1 on Chr.3, cer2-1 on Chr.4, and ms1-1 on Chr.5. This line is used in crosses to wildtype C24 which expresses an MMR altering gene for analysis of meiotic homeologous recombination on chromosomes 1–5 in conjunction with molecular recombination markers listed in Table 1.

Other Ler lines from NASC have several visual markers in close proximity to each other on the same chromosome. When these lines are used for hybrid production, analysis of homeologous meiotic recombination may make use entirely of visual recombination markers. Particularly suitable for crossing to C24 wildtype that is expressing a MMR altering gene are the following Ler lines:

NW22: relative markers are dis1—(4 cM)—ga4—(11 cM)—th*1* on chromosome 1.

NW10: relevant markers are rz-201—(5 cM)—cer3 on chromosome 5.

NW134, relevant markers are ttg—(4 cM)—ga3 on chromosome 5.

NW24(abi3-1) and NW64 (gl1-1). When present in the same plant on chromosome 3, abi3-1 and gl1-1 are 13 cM apart. Since this marker combination is not available from NASC, we have combined these markers by crossing, line NW24 to line NW64. The F1 offspring were allowed to self-fertilise and to produce F2 seeds. F2 Plants which carry both markers as homozygous traits on the same chromosome can be identified firstly, by germinating F2 seeds on germination medium containing selective concentrations of abscisic acid, and subsequently, by identifying among the abscisic acid resistant plants those individuals which show the glabra phenotype.

E(iii) Molecular Recombination Markers in Col. Ler and C24

The genome of Arabidopsis thaliana is interspersed with unique base sequences arranged as simple tandem repeats.

Allelic repeats can vary in length between different Arabidopsis subspecies and when amplified by PCR yield diagnostic DNA products of different length named Simple Sequence Length Polymorphisms (SSLPs). Many SSLPs have been genetically mapped and have been assigned to unique chromosome locations on the recombinant inbred map (Bell and Ecker. 1994, Genomics 19, 137–144; Lister and Deans lines, Weeds World 4i, May 1997).

In Table 1 are listed 28 mapped and established SSLPs between Ler and Col. A number of PCR primer pairs are described herein (SEQ ID NO:42 to SEQ ID NO:97) which also yielded SSLPs between C24 and Ler (19 SSLPs) or between C24 and Col (25 SSLPs), respectively. Polymorphic SSLPs can be used as molecular markers in the analysis of homeologous recombination between genomes from these subspecies.

The PCR reactions (25 μL) were carried out over 35 cycles (15 seconds at 94°C., 30 seconds at 55° C. and 30 seconds at 72°C.), with 0.25 U Taq DNA polymerase and 0.6 μg genomic DNA in reaction buffer containing 2 mM $MgCl_2$. PCR products were separated by agarose gel electrophoresis (4% ultra high resolution agarose) and visualised by ethidiumbromide staining. The results from the PCR experiments are summarised in Table 1, which also shows the sequence of PCR primers, primer annealing temperature (Tm). PCR product length and chromosome location of SSLP (with respect to the RI map of May 1997, Weeds World 4i).

F. Production of Hybrid Plants

C24 plants heterozygous for chlorina3A:Ac/GUS are crossed as male to emasculated wildtype Ler to produce Ler/C24(chlorina3A, GUS) hybrid seeds.

Due to the heterozygosity of the C24 parent, only 50% of hybrid plants have inherited the chlorina3A:Ac/GUS locus. The remaining 50% of hybrid plants are wildtype with respect to chlorina3A:Ac/GUS. Since the mutant locus is linked to a kanamycin resistance gene (contained on the same T-DNA as GUS) mutant plants can be pre-selected by germinating hybrid seeds on germination medium containing 50 mg/L kanamycin.

Ler plants homozygous for the five chromosome markers are male sterile (ms1-1) and are crossed without emasculation to wildtype C24 to produce Ler(an-1, py-1, gl1-1) cer2-1, ms1-1)/C24 hybrid seeds.

Other Ler plants, which are male fertile, are crossed after emasculation of the female parent to produce Ler/C24 hybrid seeds.

G. Introduction of MSH3 and MSH6/3 Antisense Genes Into Arabidonsis and Analysis of Meiotic Homeologous Recombination (i) Transformation of hybrid plants and analysis of homeologous meiotic recombination The plant transformation vectors comprising the antisense genes described in (B) and (C) above are introduced into *Agrobacterium tumefaciens* strain AGL (Lazo et al., 1991, Bio/Technology 9, 963–967) by electroporation. Recombinant Agrobacterium clones are selected on LB medium containing 50 mg/L rifampicin and 100 mg/L carbenicillin. Selected clones are used to infect roots of Arabidopsis hybrid plants (described in (F) above) using the root transformation protocol of Valyekens et al. (1988, PNAS 85. 5536–5540) except that shoot and root inducing media contain hygromycin (10 mg/L) instead of kanamycin.

Plants regenerated from roots of hybrid plants are genetic clones of root donating plants and therefore are again genetic hybrids of two Arabidopsis subspecies described in (F). However, in contrast to the root donating plants, the regenerated hybrid plants also contain the introduced transgene and the co-introduced hygromycin resistance gene with the latter allowing these plants to grow on hygromycin containing culture medium.

Hygromycin resistant plants are then allowed to enter the reproductive phase and to produce gametes by meiotic divisions of microspore and megaspore mothercells. At meiosis, the DMC1 promoter is activated and can direct the expression of antisense genes described in (B) and (C) above, leading to decreased MSH6 and/or MSH3 gene expression. This in turn depletes the gamete mothercells of MSH6 and/or MSH3 protein, thus causing alteration of MMR during meiotic divisions and increasing the recombination frequency between homeologous chromosomes.

Transgenic plants are then allowed to self-fertilise and to produce seeds. These seeds (F2 seeds with respect to hybrid production), and the plants derived therefrom, carry the homeologous recombination events which can be identified by using the visual and molecular recombination markers described in (E) above.

In case of homeologous recombination between chromosomes of Ler and C24(chlorina3A:Ac. GUS), the analysis concentrates on chromosome 2 by selecting plants showing the visual phenotypic marker chlorina. This marker thus serves as a reference point as it indicates that respective chromosomes 2 originate from C24. Other markers, such as GUS or molecular markers, on chromosome 2 may then be used to identify chromosomal regions which are derived from the Ler chromosome as a result of homeologous recombination. F2 plants of control transformants not expressing the antisense gene(s) can be analysed in parallel and the results can be used for comparison to homeologous recombination results obtained in antisense plants.

(ii) Transformation of C24 wildtype, hybrid plant production and analysis of homeologous meiotic recombination Introduction of MMR altering genes into wildtype C24 is done using the root transformation protocol as described in G(i) for transformation of hybrid plants. Transformed plants are selected by resistance to either 10 mg/L hygromycin (in case of transformation with T-DNA's derived from pNOS-Hyg-SCV) or to 50 mg/L kanamycin (in case of transformation with T-DNA's derived from pBIN19).

Transgenic plants are then allowed to self-fertilise and to produce seeds (T1 seeds). Segregation of the antibiotic resistance gene in the T1 population then indicates the number of transgene loci. Lines with a single transgene locus (indicated by a 3:1 ratio of resistant:sensitive plants) are selected and are bred to homozygosity. This is done by collecting selfed seeds (T2) from T1 plants and subsequent testing of at least four independent T2 seed populations for segregation of the antibiotic resistance gene. T2 populations which do not segregate the antibiotic resistance gene are assumed to be homozygous for both the resistance gene and the linked MMR altering gene.

C24 plants homozygous for the MMR altering gene are then crossed to Ler lines homozygous for recessive visual markers (see E(ii)) to produce C24/Ler hybrid plants as described in (F). These F1 hybrids are then allowed to enter the reproductive phase and to produce gametes by meiotic division of microspore and megaspore mothercells. At meiosis, the DMC 1 promoter is activated and can direct the expression of antisense or sense genes described in (B), (C) and (D) above, leading to decreased MSH6 and/or MSH3 gene expression. This in turn depletes the gamete mothercells of MSH6 and/or MSH3 protein, thus causing alteration of MMR during meiotic divisions and increasing the recombination frequency between the homeologous chromosomes of C24 and Ler. Recombination events are then scored in the F2 generation.

For recombination analysis, the hybrid plants are allowed to self-fertilise and to produce F2 seeds. F2 plants are then preselected for a first visual marker. Since this marker is recessive, its visual presence indicates homozygosity for Ler DNA at the relevant locus. Those F2 plants which show this first visual marker are then analysed for the presence or absence of a second visual marker which in the Ler parent is closely linked to the first marker. Absence of the second visual marker indicates recombination between the relevant C24 and Ler chromosomes between the first and second marker. The frequency of recombination in transgenic hybrids is compared to the recombination frequency in control hybrids not expressing the MMR altering gene.

Examples of recombination analysis are the following. The Ler line NW22(dis1, ga4, th1) is used for crosses to transformedC24.

F2 plants are preselected first for thiamine requirement (th1) and then are further analysed for re-appearance of wildtype height (loss of ga4) and/or re-appearance of normal trichomes (loss of dis1) as a result of recombination.

The Ler line NW10(tz-201, cer3) is used for crosses to transformedC24.

F2 plants are then preselected first for thiazole requirement (tz) and then are further analysed for re-appearance of normal, i.e. non-shiny stems (loss of cer3) as a result of recombination.

The Ler line NW134 (ttg, ga3) is used for crosses to transformedC24. F2 plants are first preselected for dwarfish appearance (ga3) and are then analysed for re-appearance of trichomes (loss of ttg) as a result of recombination.

Ler plants homozygous for abi3-1 and gl1-1 are used for crosses to transformedC24F2 plants are first preselected for their ability to germinate in the presence of abscisic acid and are then analysed for re-appearance of trichomes on the leaves (loss of gl1-1) as a result of recombination.

In the case of homeologous recombination between transformedC24 and the Ler line NW1 (an-1, py-1, gl1-1, cer2-1, ms1-1), recombination analysis is similar the one described above, except that the second marker is not a visual marker but has to be a molecular marker. This is because the Ler parent carries only one visual marker per chromosome.

TABLE 1

SSLP Markers in *Arabidopsis thaliana* Subspecies

| Chromosome | RI Map Position | PCR Primer Pair | Primer Sequence | Tm [° C.] | length/COL | length/LER | length/C24 |
|---|---|---|---|---|---|---|---|
| I | 2.3 | ATEAT1 F | GCCACTGCGTGAATGATATG | 57.8 | 172 | 162 | 162 |
|  |  | ATEAT1 R | CGAACAGCCAACATTAATTCC | 58.2 |  |  |  |
| I | 9.3 | NGA63 F | AACCAAGGCACAGAAGCG | 57.3 | 111 | 89 | 120 |
|  |  | NGA63 R | ACCCAAGTGATCGCCACC | 59.6 |  |  |  |
| I | 40.1 | NGA248 F | TACCGAACCAAAACACAAAGG | 56.1 | 143 | 129 | no amplific. |
|  |  | NGA248 R | TCTGTATCTCGGTGAATTCTCC | 58.2 |  |  |  |
| I | 81.2 | NGA128 F | GGTCTGTTGATGTCGTAAGTCG | 60.1 | 180 | 190 | no amplific. |
|  |  | NGA128 R | ATCTTGAAACCTTTAGGGAGGG | 58.2 |  |  |  |
| I | 81.2 | NGA280 F | CTGATCTCACGGACAATAGTGC | 60.1 | 105 | 85 | 85 |
|  |  | NGA280 R | GGCTCCATAAAAAGTGCACC | 57.8 |  |  |  |
| I | 111.4 | NGA111 F | CTCCAGTTGGAAGCTAAAGGG | 60 | 128 | 162 | 170 |
|  |  | NGA111 R | TGTTTTTTAGGACAAATGGCG | 70 |  |  |  |
| II | ca. 7.5 | NGA168 F | CCTTCACATCCAAAACCCAC | 57.8 | 213 | 217 | 208 |
|  |  | NGA168 R | GCACATACCCACAACCAGAA | 57.8 |  |  |  |
| II | ca. 48 | NGA1126L | CGCTACGCTTTTCGGTAAAG | 57.8 | 191 | 199 | 196 |
|  |  | NGA1126R | GCACAGTCCAAGTCACAACC | 59.9 |  |  |  |
| II | 62.2 | NGA361L | AAAGAGATGAGAATTTGGAC | 51.7 | 114 | 120 | 114 |
|  |  | NGA361R | ACATATCAATATATTAAAGTAGC | 49.5 |  |  |  |
| II | 73 | NGA168 F | TCGTCTACTGCACTGCCG | 59.6 | 151 | 135 | 135 |
|  |  | NGA168 R | GAGGACATGTATAGGAGCCTCG | 61.9 |  |  |  |
| II | ca. 77 | AthBIO2 L | TGACCTCCTCTTCCATGGAG | 59.9 | 141 | 209 | 139 |
|  |  | AthBIO2 R | TTAACAGAAACCCAAAGCTTTC | 54.5 |  |  |  |
| II | ca. 83 | AthUBIQUE L | AGGCAAATGTCCATTTCATTG | 54.1 | 146 | 148 | 148 |
|  |  | AthUBIQUE R | ACGACATGGCAGATTTCTCC | 57.8 |  |  |  |
| III | 3.4 | NGA172 F | AGCTGCTTCCTTATAGCGTCC | 60 | 162 | 136 | 140 |
|  |  | NGA172 R | CATCCGAATGCCATTGTTC | 55.4 |  |  |  |
| III | 12.8 | NGA126 F | GAAAAAACGCTACTTTCGTGG | 56.1 | 119 | 147 | no amplific. |
|  |  | NGA126 R | CAAGAGCAATATCAAGAGCAGC | 58.2 |  |  |  |
| III | 17.5 | NGA162 F | CATGCAATTTGCATCTGAGG | 55.8 | 107 | 89 | no amplific. |
|  |  | NGA162 R | CTCTGTCACTCTTTTCCTCTGG | 60.1 |  |  |  |
| III | 81.8 | NGA6 F | TGGATTTCTTCCTCTCTTCAC | 56.1 | 143 | 123 | 143 |
|  |  | NGA6 R | ATGGAGAAGCTTACACTGATC | 56.1 |  |  |  |
| IV | 19.8 | NGA12 F | AATGTTGTCCTCCCCTCCTC | 59.9 | 247 | 234 | 220 |
|  |  | NGA12 R | TGATGCTCTCTGAAACAAGAGC | 58.2 |  |  |  |
| IV | 24.1 | NGA8 F | GAGGGCAAATCTTTATTTCGG | 56.1 | 154 | 198 | 190 |
|  |  | NGA8 R | TGGCTTTCGTTTATAAACATCC | 54.5 |  |  |  |
| IV | 102 | NGA1107 L | GCGAAAAAACAAAAAAATCCA | 50.2 | 150 | 140 | 140 |
|  |  | NGA1107 R | CGACGAATCGACAGAATTAGG | 58 |  |  |  |
| V | 11.8 | NGA225 F | GAAATCCAAATCCCAGAGAGG | 58 | 119 | 189 | 119 |
|  |  | NGA225 R | TCTCCCCACTAGTTTTGTGTCC | 60.1 |  |  |  |
| V | 16.7 | NGA249 F | TACCGTCAATTTCATCGCC | 55.4 | 125 | 115 | 115 |
|  |  | NGA249 R | GGATCCCTAACTGTAAAATCCC | 58.2 |  |  |  |
| V | 19.9 | CA72 F | AATCCCAGTAACCAAACACACA | 56.3 | 124 | 110 | 110 |
|  |  | CA72 R | CCCAGTCTAACCACGACCAC | 61.9 |  |  |  |
| V | 20 | NGA151 F | GTTTTGGGAAGTTTTGCTGG | 55.8 | 150 | 120 | 130 |
|  |  | NGA151 R | CAGTCTAAAAGCGAGAGTATGATG | 58.6 |  |  |  |

TABLE 1-continued

SSLP Markers in *Arabidopsis thaliana* Subspecies

| Chromosome | RI Map Position | PCR Primer Pair | Primer Sequence | Tm [° C.] | length/COL | length/LER | length/C24 |
|---|---|---|---|---|---|---|---|
| V | 24 | NGA106 F | GTTATGGAGTTTCTAGGGCACG | 60.1 | 157 | 123 | 130 |
|   |    | NGA106 R | TGCCCCATTTTGTTCTTCTC | 55.8 |   |   |   |
| V | 37.8 | NGA139 F | AGAGCTACCAGATCCGATGG | 59.9 | 174 | 132 | 132 |
|   |    | NGA139 R | GGTTTCGTTTCACTATCCAGG | 55.8 |   |   |   |
| V | 50 | NGA76 F | GGAGAAAATGTCACTCTCCACC | 60.1 | 231 | >250 | 300 |
|   |    | NGA76 R | AGGCATGGGAGACATTTACG | 57.8 |   |   |   |
| V | 61.1 | ATHSO191 L | CTCCACCAATCATGCAAATG | 55.8 | 148 | 156 | 146 |
|   |    | ATHSO191 R | TGATGTTGATGGAGATGGTCA | 53.7 |   |   |   |
| V | 81.7 | NGA129 F | TCAGGAGGAACTAAAGTGAGGG | 60.1 | 177 | 179 | 172 |
|   |    | NGA129 R | CACACTGAAGATGGTCTTGAGG | 60.1 |   |   |   |

What is claimed is:

1. An isolated and purified nucleic acid comprising a nucleolide sequence encoding a polypeptide having the amino acid sequence of AtMSH3 (SEQ ID NO: 19).

2. The nucleic acid of claim 1 further comprising a regulation element operably linked to said AtMSH3-encoding sequence.

3. A plasmid or vector comprising the nucleic acid of claim 2.

4. A plant cell stably transformed, transfected or electroporated with the plasmid or vector according to claim 3.

5. A plant comprising the cell according to claim 4.

6. A process for at least partially inactivating the DNA mismatch repair system of a plant cell, comprising:

transforming or transfecting said plant cell with a nucleic acid comprising a regulation element operably linked to a nucleotide sequence encoding a polypeptide having the amino acid sequence of AtMSH3 (SEQ ID NO:19);

growing said cell under conditions that permit expression of said AtMSH3-encoding sequence; and inactivating said DNA mismatch repair system of said plant cell.

7. The process of claim 6, wherein said plant is selected from the group consisting of Brassicaceae, Poaceae, Solanaceae, Asteraceae, Malvaceae, Fabaccae, Linaceae, Canabinaccac, Dauaccae and Cucurbitaceae.

* * * * *

SEQUENCE LISTING

```
<160> NUMBER OF SEQ ID NOS: 100

<210> SEQ ID NO 1
<211> LENGTH: 23
<212> TYPE: DNA
<213> ORGANISM: Artificial Sequence
<220> FEATURE:
<221> NAME/KEY: modified_base
<222> LOCATION: (11)...(11)
<223> OTHER INFORMATION: I
<220> FEATURE:
<221> NAME/KEY: modified_base
<222> LOCATION: (14)...(14)
<223> OTHER INFORMATION: I
<221> NAME/KEY: modified_base
<222> LOCATION: (17)...(17)
<223> OTHER INFORMATION: I
<220> FEATURE:
<223> OTHER INFORMATION: Degenerate oligonucleotides UPMU used to
      isolate AtMSH3 and AtMSH6.
<300> PUBLICATION INFORMATION:
<301> AUTHORS: Reenan and Kolodner
<302> TITLE: Genetics
<303> JOURNAL: 132
<306> PAGES: 963-973
<307> DATE: 1992

<400> SEQUENCE: 1
ctggatccac nggnccnaay atg                                          23

<210> SEQ ID NO 2
<211> LENGTH: 23
<212> TYPE: DNA
<213> ORGANISM: Artificial Sequence
<220> FEATURE:
<223> OTHER INFORMATION: Degenerate oligonucleotides DOMU used to
      isolate AtMSH3 and AtMSH6.
<220> FEATURE:
<221> NAME/KEY: modified_base
<222> LOCATION: (15)...(15)
<223> OTHER INFORMATION: I
<220> FEATURE:
<221> NAME/KEY: modified_base
<222> LOCATION: (18)...(18)
<223> OTHER INFORMATION: I
<300> PUBLICATION INFORMATION:
<301> AUTHORS: Reenan and Kolodner
<302> TITLE: Genetics
<303> JOURNAL: 132
<306> PAGES: 963-973
<307> DATE: 1992

<400> SEQUENCE: 2
```
ctggatccrt artgngtnrc raa                                    23

<210> SEQ ID NO 3
<211> LENGTH: 24
<212> TYPE: DNA
<213> ORGANISM: Artificial Sequence
<220> FEATURE:
<223> OTHER INFORMATION: MSH3 specific primer 636 for PCR using cDNA of
      Arabidopsis thaliana ecotype Columbia.

<400> SEQUENCE: 3
tgctagtgcc tcttgcaagc tcat                                   24

<210> SEQ ID NO 4
<211> LENGTH: 27
<212> TYPE: DNA
<213> ORGANISM: Artificial Sequence
<220> FEATURE:
<223> OTHER INFORMATION: Primer AP1 for PCR using cDNA of Arabidopsis
      thaliana ecotype Columbia containing adapter
      sequences ligated to both its ends.

<400> SEQUENCE: 4
ccatcctaat acgactcact atagggc                                27

<210> SEQ ID NO 5
<211> LENGTH: 23
<212> TYPE: DNA
<213> ORGANISM: Artificial Sequence
<220> FEATURE:
<223> OTHER INFORMATION: Primer AP2 for PCR using cDNA of Arabidopsis
      thaliana ecotype Columbia containing adapter
      sequences ligated to both its ends.

<400> SEQUENCE: 5
actcactata gggctcgagc ggc                                    23

<210> SEQ ID NO 6
<211> LENGTH: 30
<212> TYPE: DNA
<213> ORGANISM: Artificial Sequence
<220> FEATURE:
<223> OTHER INFORMATION: MSH3 specific primer S525 for PCR using cDNA of
      Arabidopsis thaliana ecotype Columbia.

<400> SEQUENCE: 6
aggttctgat tatgtgtgac gctttactta                             30

<210> SEQ ID NO 7
<211> LENGTH: 29
<212> TYPE: DNA
<213> ORGANISM: Artificial Sequence
<220> FEATURE:
<223> OTHER INFORMATION: MSH3 specific primer S51 for PCR using cDNA of
      Arabidopsis thaliana ecotype Columbia.

<400> SEQUENCE: 7
ggatcgggta ctgggttttg agtgtgagg                              29

<210> SEQ ID NO 8
<211> LENGTH: 24
<212> TYPE: DNA
<213> ORGANISM: Artificial Sequence
<220> FEATURE:
<223> OTHER INFORMATION: MSH3 specific primer 635 for PCR using cDNA of
      Arabidopsis thaliana ecotype Columbia.

-continued

<400> SEQUENCE: 8
gcacgtgctt gatggtgttt tcac                                        24

<210> SEQ ID NO 9
<211> LENGTH: 28
<212> TYPE: DNA
<213> ORGANISM: Artificial Sequence
<220> FEATURE:
<223> OTHER INFORMATION: MSH3 specific primer S523 for PCR using cDNA of
      Arabidopsis thaliana ecotype Columbia.

<400> SEQUENCE: 9
tcagacagta tccagcatgg cagaagta                                    28

<210> SEQ ID NO 10
<211> LENGTH: 33
<212> TYPE: DNA
<213> ORGANISM: Artificial Sequence
<220> FEATURE:
<223> OTHER INFORMATION: MSH3 specific primer 1S5 for PCR using cDNA of
      Arabidopsis thaliana ecotype Columbia.

<400> SEQUENCE: 10
atcccgggat gggcaagcaa aagcagcaga cga                              33

<210> SEQ ID NO 11
<211> LENGTH: 27
<212> TYPE: DNA
<213> ORGANISM: Artificial Sequence
<220> FEATURE:
<223> OTHER INFORMATION: MSH3 specific primer S53 for PCR using cDNA of
      Arabidopsis thaliana ecotype Columbia.

<400> SEQUENCE: 11
gacaaagagc gaaatgaggc cccttgg                                     27

<210> SEQ ID NO 12
<211> LENGTH: 1250
<212> TYPE: DNA
<213> ORGANISM: Arabidopsis thaliana ecotype Columbia
<220> FEATURE:
<221> NAME/KEY: misc_feature
<222> LOCATION: (0)...(0)
<223> OTHER INFORMATION: Clone 52

<400> SEQUENCE: 12
cccgggatgg gcaagcaaaa gcagcagacg atttctcgtt tcttcgctcc caacccaaa     60 tccccgactc acgaaccgaa tccggtagcc gaatcatcaa caccgccacc gaagatatcc   120
gccactgtat ccttctctcc ttccaagcgt aagcttctct ccgaccacct cgccgccgcg   180
tcacccaaaa agcctaaaact ttctcctcac actcaaaacc cagtacccga tcccaattta   240
caccaaagat ttctccagag atttctggaa ccctcgccgg aggaatatgt tcccgaaacg   300
tcatcatcga ggaaatacac accattggaa cagcaagtgg tggagctaaa gagcaagtac   360
ccagatgtgt ttttgatggt ggaagttggt tacaggtaca gattcttcgg agaagacgcg   420
gagatcgcag cacgcgtgtt gggtatttac gctcatatgg atcacaattt catgacggcg   480
agtgtgccaa catttcgatt gaatttccat gtgagaagac tggtgaatgc aggatacaag   540
attggtgtag tgaagcagac tgaaactgca gccattaagt cccatggtgc aaaccggacc   600 ggccccttttt tccgggggact gtcggcgttg tataccaaag ccacgcttga agcggctgag   660
gatataagtg gtggttgtgg tggtgaagaa ggttttggtt cacagagtaa tttcttggtt    720

```
tgtgttgtgg atgagagagt taagtcggag acattaggct gtggtattga aatgagtttt    780
gatgttagag tcggtgttgt tggcgttgaa atttcgacag gtgaagttgt ttatgaagag    840
ttcaatgata atttcatgag aagtggatta gaggctgtga ttttgagctt gtcaccagct    900
gagctgttgc ttggccagcc tctttcacaa caaactgaga agttttttggt ggcacatgct    960 ggacctacct caaacgttcg agtggaacgt gcctcactgg attgtttcag caatggtaat   1020
gcagtagatg aggttatttc attatgtgaa aaaatcagcg caggtaactt agaagatgat   1080
aaagaaatga agctggaggc tgctgaaaaa ggaatgtctt gcttgacagt tcatacaatt   1140
atgaacatgc cacatctgac tgttcaagcc ctcgccctaa cgttttgcca tctcaaacag   1200
tttggatttg aaaggatcct ttaccaaggg gcctcatttc gctctttgtc               1250
```

<210> SEQ ID NO 13
<211> LENGTH: 34
<212> TYPE: DNA
<213> ORGANISM: Artificial Sequence
<220> FEATURE:
<223> OTHER INFORMATION: MSH3 specific primer 2S5 for PCR using cDNA of
      Arabidopsis thaliana ecotype Columbia.

<400> SEQUENCE: 13

```
atcccgggtc aaaatgaaca agttggtttt agtc                                 34
```

<210> SEQ ID NO 14
<211> LENGTH: 27
<212> TYPE: DNA
<213> ORGANISM: Artificial Sequence
<220> FEATURE:
<223> OTHER INFORMATION: MSH3 specific primer S52 for PCR using cDNA of
      Arabidopsis thaliana ecotype Columbia.

<400> SEQUENCE: 14

```
gccacatctg actgttcaag ccctcgc                                         27
```

<210> SEQ ID NO 15
<211> LENGTH: 2110
<212> TYPE: DNA
<213> ORGANISM: Arabidopsis thaliana ecotype Columbia
<220> FEATURE:
<221> NAME/KEY: misc_feature
<222> LOCATION: (0)...(0)
<223> OTHER INFORMATION: Clone 13

<400> SEQUENCE: 15

```
gccacatctg actgttcaag ccctcgccct aacgttttgc catctcaaac agtttggatt     60
tgaaaggatc ctttaccaag gggcctcatt tcgctctttg tcaagtaaca cagagatgac    120
tctctcagcc aatactctgc aacagttgga ggttgtgaaa ataattcag atggatcgga     180 atctggctcc ttattccata atatgaatca cacacttaca gtatatggtt ccaggcttct    240
tagacactgg gtgactcatc ctctatgcga tagaaatttg atatctgctc ggcttgatgc    300
tgtttctgag atttctgctt gcatgggatc tcatagttct tcccagctca gcagtgagtt    360
ggttgaagaa ggttctgaga gagcaattgt atcacctgag ttttatctcg tgctctcctc    420
agtcttgaca gctatgtcta gatcatctga tattcaacgt ggaataacaa gaatcttttca    480 tcggactgct aaagccacag agttcattgc agttatgaa gctatttttac ttgcggggaa    540 gcaaattcag cggcttggca taaagcaaga ctctgaaatg aggagtatgc aatctgcaac    600
tgtgcgatct actcttttga gaaaattgat ttctgttatt tcatcccctg ttgtggttga    660
caatgccgga aaacttctct ctgccctaaa taaggaagcg gctgttcgag gtgacttgct    720
```

```
cgacatacta atcacttcca gcgaccaatt tcctgagctt gctgaagctc gccaagcagt    780
tttagtcatc agggaaaagc tggattcctc gatagcttca tttcgcaaga agctcgctat    840
tcgaaatttg gaatttcttc aagtgtcggg gatcacacat ttgatagagc tgcccgttga    900
ttccaaggtc cctatgaatt gggtgaaagt aaatagcacc aagaagacta ttcgatatca    960
tcccccagaa atagtagctg gcttggatga gctagctcta gcaactgaac atcttgccat   1020
tgtgaaccga gcttcgtggg atagtttcct caagagtttc agtagatact acacagattt   1080
taaggctgcc gttcaagctc ttgctgcact ggactgtttg cactcccttt caactctatc   1140
tagaaacaag aactatgtcc gtcccgagtt tgtggatgac tgtgaaccag ttgagataaa   1200
catacagtct ggtcgtcatc ctgtactgga gactatatta caagataact tcgtcccaaa   1260
tgacacaatt ttgcatgcag aagggaata ttgccaaatt atcaccggac taacatggg    1320 aggaaagagc tgctatatcc gtcaagttgc tttaatttcc ataatggctc aggttggttc   1380
ctttgtacca gcgtcattcg ccaagctgca cgtgcttgat ggtgttttca ctcggatggg   1440
tgcttcagac agtatccagc atggcagaag tacctttcta gaagaattaa gtgaagcgtc   1500
acacataatc agaacctgtt cttctcgttc gcttgttata ttagatgagc ttggaagagg   1560
cactagcaca cacgacggtg tagccattgc ctatgcaaca ttcagcatc tcctagcaga    1620 aaagagatgt ttggttcttt ttgtcacgca ttaccctgaa atagctgaga tcagtaacgg   1680
attcccaggt tctgttggga cataccatgt ctcgtatctg acattgcaga aggataaagg   1740
cagttatgat catgatgatg tgacctacct atataagctt gtgcgtggtc tttgcagcag   1800
gagctttggt tttaaggttg ctcagcttgc ccagatacct ccatcatgta tacgtcgagc   1860
catttcaatg gctgcaaaat tggaagctga ggtacgtgca agagagagaa atacacgcat   1920
gggagaacca gaaggacatg aagaaccgag aggcgcagaa gaatctattt cggctctagg   1980
tgacttgttt gcagacctga aatttgctct ctctgaagag gacccttgga aagcattcga   2040
gtttttaaag catgcttgga agattgctgg caaaatcaga ctaaaaccaa cttgttcatt   2100
ttgacccggg                                                          2110
```

<210> SEQ ID NO 16
<211> LENGTH: 29
<212> TYPE: DNA
<213> ORGANISM: Artificial Sequence
<220> FEATURE:
<223> OTHER INFORMATION: MSH3 specific primer S51 for PCR using cDNA of
      Arabidopsis thaliana ecotype Columbia.

<400> SEQUENCE: 16
ggatcgggta ctgggttttg agtgtgagg                                       29

<210> SEQ ID NO 17
<211> LENGTH: 30
<212> TYPE: DNA
<213> ORGANISM: Artificial Sequence
<220> FEATURE:
<223> OTHER INFORMATION: MSH3 specific primer S525 for PCR using cDNA of
      Arabidopsis thaliana ecotype Columbia.

<400> SEQUENCE: 17
aggttctgat tatgtgtgac gctttactta                                      30

<210> SEQ ID NO 18
<211> LENGTH: 3522
<212> TYPE: DNA

<213> ORGANISM: Arabidopsis thaliana ecotype Columbia
<220> FEATURE:
<221> NAME/KEY: CDS
<222> LOCATION: (100)...(3342)
<223> OTHER INFORMATION: AtMSH3 full-length cDNA and deduced sequence of the encoded polypeptide.

<400> SEQUENCE: 18

```
cctaagaaag cgcgcgaaaa ttggcaaccc aagttcgcca tagccacgac cacgaccttc      60
catttctctt aaacggagga gattacgaat aaagcaatt atg ggc aag caa aag        114
                                           Met Gly Lys Gln Lys
                                             1               5 cag cag acg att tct cgt ttc ttc gct ccc aaa ccc aaa tcc ccg act       162
Gln Gln Thr Ile Ser Arg Phe Phe Ala Pro Lys Pro Lys Ser Pro Thr
             10                  15                  20 cac gaa ccg aat ccg gta gcc gaa tca tca aca ccg cca ccg aag ata       210
His Glu Pro Asn Pro Val Ala Glu Ser Ser Thr Pro Pro Pro Lys Ile
         25                  30                  35 tcc gcc act gta tcc ttc tct cct tcc aag cgt aag ctt ctc tcc gac       258
Ser Ala Thr Val Ser Phe Ser Pro Ser Lys Arg Lys Leu Leu Ser Asp
     40                  45                  50 cac ctc gcc gcc gcg tca ccc aaa aag cct aaa ctt tct cct cac act       306
His Leu Ala Ala Ala Ser Pro Lys Lys Pro Lys Leu Ser Pro His Thr
 55                  60                  65 caa aac cca gta ccc gat ccc aat tta cac caa aga ttt ctc cag aga       354
Gln Asn Pro Val Pro Asp Pro Asn Leu His Gln Arg Phe Leu Gln Arg
 70                  75                  80                  85 ttt ctg gaa ccc tcg ccg gag gaa tat gtt ccc gaa acg tca tca tcg       402
Phe Leu Glu Pro Ser Pro Glu Glu Tyr Val Pro Glu Thr Ser Ser Ser
                 90                  95                 100 agg aaa tac aca cca ttg gaa cag caa gtg gtg gag cta aag agc aag       450
Arg Lys Tyr Thr Pro Leu Glu Gln Gln Val Val Glu Leu Lys Ser Lys
            105                 110                 115 tac cca gat gtg gtt ttg atg gtg gaa gtt ggt tac agg tac aga ttc       498
Tyr Pro Asp Val Val Leu Met Val Glu Val Gly Tyr Arg Tyr Arg Phe
        120                 125                 130 ttc gga gaa gac gcg gag atc gca gca cgc gtg ttg ggt att tac gct       546
Phe Gly Glu Asp Ala Glu Ile Ala Ala Arg Val Leu Gly Ile Tyr Ala
    135                 140                 145 cat atg gat cac aat ttc atg acg gcg agt gtg cca aca ttt cga ttg       594
His Met Asp His Asn Phe Met Thr Ala Ser Val Pro Thr Phe Arg Leu
150                 155                 160                 165 aat ttc cat gtg aga aga ctg gtg aat gca gga tac aag att ggt gta       642
Asn Phe His Val Arg Arg Leu Val Asn Ala Gly Tyr Lys Ile Gly Val
                170                 175                 180 gtg aag cag act gaa act gca gcc att aag tcc cat ggt gca aac cgg       690
Val Lys Gln Thr Glu Thr Ala Ala Ile Lys Ser His Gly Ala Asn Arg
            185                 190                 195 acc ggc cct ttt ttc cgg gga ctg tcg gcg ttg tat acc aaa gcc acg       738
Thr Gly Pro Phe Phe Arg Gly Leu Ser Ala Leu Tyr Thr Lys Ala Thr
        200                 205                 210 ctt gaa gcg gct gag gat ata agt ggt ggt tgt ggt ggt gaa gaa ggt       786
Leu Glu Ala Ala Glu Asp Ile Ser Gly Gly Cys Gly Gly Glu Glu Gly
    215                 220                 225 ttt ggt tca cag agt aat ttc ttg gtt tgt gtt gtg gat gag aga gtt       834
Phe Gly Ser Gln Ser Asn Phe Leu Val Cys Val Val Asp Glu Arg Val
230                 235                 240                 245 aag tcg gag aca tta ggc tgt ggt att gaa atg agt ttt gat gtt aga       882
Lys Ser Glu Thr Leu Gly Cys Gly Ile Glu Met Ser Phe Asp Val Arg
                250                 255                 260
```

-continued

| | |
|---|---|
| gtc ggt gtt gtt ggc gtt gaa att tcg aca ggt gaa gtt gtt tat gaa<br>Val Gly Val Val Gly Val Glu Ile Ser Thr Gly Glu Val Val Tyr Glu<br>265 270 275 | 930 |
| gag ttc aat gat aat ttc atg aga agt gga tta gag gct gtg att ttg<br>Glu Phe Asn Asp Asn Phe Met Arg Ser Gly Leu Glu Ala Val Ile Leu<br>280 285 290 | 978 |
| agc ttg tca cca gct gag ctg ttg ctt ggc cag cct ctt tca caa caa<br>Ser Leu Ser Pro Ala Glu Leu Leu Leu Gly Gln Pro Leu Ser Gln Gln<br>295 300 305 | 1026 |
| act gag aag ttt ttg gtg gca cat gct gga cct acc tca aac gtt cga<br>Thr Glu Lys Phe Leu Val Ala His Ala Gly Pro Thr Ser Asn Val Arg<br>310 315 320 325 | 1074 |
| gtg gaa cgt gcc tca ctg gat tgt ttc agc aat ggt aat gca gta gat<br>Val Glu Arg Ala Ser Leu Asp Cys Phe Ser Asn Gly Asn Ala Val Asp<br>330 335 340 | 1122 |
| gag gtt att tca tta tgt gaa aaa atc agc gca ggt aac tta gaa gat<br>Glu Val Ile Ser Leu Cys Glu Lys Ile Ser Ala Gly Asn Leu Glu Asp<br>345 350 355 | 1170 |
| gat aaa gaa atg aag ctg gag gct gct gaa aaa gga atg tct tgc ttg<br>Asp Lys Glu Met Lys Leu Glu Ala Ala Glu Lys Gly Met Ser Cys Leu<br>360 365 370 | 1218 |
| aca gtt cat aca att atg aac atg cca cat ctg act gtt caa gcc ctc<br>Thr Val His Thr Ile Met Asn Met Pro His Leu Thr Val Gln Ala Leu<br>375 380 385 | 1266 |
| gcc cta acg ttt tgc cat ctc aaa cag ttt gga ttt gaa agg atc ctt<br>Ala Leu Thr Phe Cys His Leu Lys Gln Phe Gly Phe Glu Arg Ile Leu<br>390 395 400 405 | 1314 |
| tac caa ggg gcc tca ttt cgc tct ttg tca agt aac aca gag atg act<br>Tyr Gln Gly Ala Ser Phe Arg Ser Leu Ser Ser Asn Thr Glu Met Thr<br>410 415 420 | 1362 |
| ctc tca gcc aat act ctg caa cag ttg gag gtt gtg aaa aat aat tca<br>Leu Ser Ala Asn Thr Leu Gln Gln Leu Glu Val Val Lys Asn Asn Ser<br>425 430 435 | 1410 |
| gat gga tcg gaa tct ggc tcc tta ttc cat aat atg aat cac aca ctt<br>Asp Gly Ser Glu Ser Gly Ser Leu Phe His Asn Met Asn His Thr Leu<br>440 445 450 | 1458 |
| aca gta tat gct tcc agg ctt ctt aga cac tgg gtg act cat cct cta<br>Thr Val Tyr Ala Ser Arg Leu Leu Arg His Trp Val Thr His Pro Leu<br>455 460 465 | 1506 |
| tgc gat aga aat ttg ata tct gct cgg ctt gat gct gtt tct gag att<br>Cys Asp Arg Asn Leu Ile Ser Ala Arg Leu Asp Ala Val Ser Glu Ile<br>470 475 480 485 | 1554 |
| tct gct tgc atg gga tct cat agt tct tcc cag ctc agc agt gag ttg<br>Ser Ala Cys Met Gly Ser His Ser Ser Ser Gln Leu Ser Ser Glu Leu<br>490 495 500 | 1602 |
| gtt gaa gaa ggt tct gag aga gca att gta tca cct gag ttt tat ctc<br>Val Glu Glu Gly Ser Glu Arg Ala Ile Val Ser Pro Glu Phe Tyr Leu<br>505 510 515 | 1650 |
| gtg ctc tcc tca gtc ttg aca gct atg tct aga tca tct gat att caa<br>Val Leu Ser Ser Val Leu Thr Ala Met Ser Arg Ser Ser Asp Ile Gln<br>520 525 530 | 1698 |
| cgt gga ata aca aga atc ttt cat cgg act gct aaa gcc aca gag ttc<br>Arg Gly Ile Thr Arg Ile Phe His Arg Thr Ala Lys Ala Thr Glu Phe<br>535 540 545 | 1746 |
| att gca gtt atg gaa gct att tta ctt gcg ggg aag caa att cag cgg<br>Ile Ala Val Met Glu Ala Ile Leu Leu Ala Gly Lys Gln Ile Gln Arg<br>550 555 560 565 | 1794 |
| ctt ggc ata aag caa gac tct gaa atg agg agt atg caa tct gca act<br>Leu Gly Ile Lys Gln Asp Ser Glu Met Arg Ser Met Gln Ser Ala Thr<br>570 575 580 | 1842 |

```
gtg cga tct act ctt ttg aga aaa ttg att tct gtt att tca tcc cct    1890
Val Arg Ser Thr Leu Leu Arg Lys Leu Ile Ser Val Ile Ser Ser Pro
            585                 590                 595 gtt gtg gtt gac aat gcc gga aaa ctt ctc tct gcc cta aat aag gaa    1938
Val Val Val Asp Asn Ala Gly Lys Leu Leu Ser Ala Leu Asn Lys Glu
        600                 605                 610 gcg gct gtt cga ggt gac ttg ctc gac ata cta atc act tcc agc gac    1986
Ala Ala Val Arg Gly Asp Leu Leu Asp Ile Leu Ile Thr Ser Ser Asp
    615                 620                 625 caa ttt cct gag ctt gct gaa gct cgc caa gca gtt tta gtc atc agg    2034
Gln Phe Pro Glu Leu Ala Glu Ala Arg Gln Ala Val Leu Val Ile Arg
630                 635                 640                 645 gaa aag ctg gat tcc tcg ata gct tca ttt cgc aag aag ctc gct att    2082
Glu Lys Leu Asp Ser Ser Ile Ala Ser Phe Arg Lys Lys Leu Ala Ile
                650                 655                 660 cga aat ttg gaa ttt ctt caa gtg tcg ggg atc aca cat ttg ata gag    2130
Arg Asn Leu Glu Phe Leu Gln Val Ser Gly Ile Thr His Leu Ile Glu
            665                 670                 675 ctg ccc gtt gat tcc aag gtc cct atg aat tgg gtg aaa gta aat agc    2178
Leu Pro Val Asp Ser Lys Val Pro Met Asn Trp Val Lys Val Asn Ser
        680                 685                 690 acc aag aag act att cga tat cat ccc cca gaa ata gta gct ggc ttg    2226
Thr Lys Lys Thr Ile Arg Tyr His Pro Pro Glu Ile Val Ala Gly Leu
    695                 700                 705 gat gag cta gct cta gca act gaa cat ctt gcc att gtg aac cga gct    2274
Asp Glu Leu Ala Leu Ala Thr Glu His Leu Ala Ile Val Asn Arg Ala
710                 715                 720                 725 tcg tgg gat agt ttc ctc aag agt ttc agt aga tac tac aca gat ttt    2322
Ser Trp Asp Ser Phe Leu Lys Ser Phe Ser Arg Tyr Tyr Thr Asp Phe
                730                 735                 740 aag gct gcc gtt caa gct ctt gct gca ctg gac tgt ttg cac tcc ctt    2370
Lys Ala Ala Val Gln Ala Leu Ala Ala Leu Asp Cys Leu His Ser Leu
            745                 750                 755 tca act cta tct aga aac aag aac tat gtc cgt ccc gag ttt gtg gat    2418
Ser Thr Leu Ser Arg Asn Lys Asn Tyr Val Arg Pro Glu Phe Val Asp
        760                 765                 770 gac tgt gaa cca gtt gag ata aac ata cag tct ggt cgt cat cct gta    2466
Asp Cys Glu Pro Val Glu Ile Asn Ile Gln Ser Gly Arg His Pro Val
    775                 780                 785 ctg gag act ata tta caa gat aac ttc gtc cca aat gac aca att ttg    2514
Leu Glu Thr Ile Leu Gln Asp Asn Phe Val Pro Asn Asp Thr Ile Leu
790                 795                 800                 805 cat gca gaa ggg gaa tat tgc caa att atc acc gga cct aac atg gga    2562
His Ala Glu Gly Glu Tyr Cys Gln Ile Ile Thr Gly Pro Asn Met Gly
                810                 815                 820 gga aag agc tgc tat atc cgt caa gtt gct tta att tcc ata atg gct    2610
Gly Lys Ser Cys Tyr Ile Arg Gln Val Ala Leu Ile Ser Ile Met Ala
            825                 830                 835 cag gtt ggt tcc ttt gta cca gcg tca ttc gcc aag ctg cac gtg ctt    2658
Gln Val Gly Ser Phe Val Pro Ala Ser Phe Ala Lys Leu His Val Leu
        840                 845                 850 gat ggt gtt ttc act cgg atg ggt gct tca gac agt atc cag cat ggc    2706
Asp Gly Val Phe Thr Arg Met Gly Ala Ser Asp Ser Ile Gln His Gly
    855                 860                 865 aga agt acc ttt cta gaa gaa tta agt gaa gcg tca cac ata atc aga    2754
Arg Ser Thr Phe Leu Glu Glu Leu Ser Glu Ala Ser His Ile Ile Arg
870                 875                 880                 885 acc tgt tct tct cgt tcg ctt gtt ata tta gat gag ctt gga aga ggc    2802
Thr Cys Ser Ser Arg Ser Leu Val Ile Leu Asp Glu Leu Gly Arg Gly
```

|  |  |  |  |  |  |  |  |  |  |  |  |  |  |  |  |
|---|---|---|---|---|---|---|---|---|---|---|---|---|---|---|---|
|  |  |  |  | 890 |  |  |  | 895 |  |  |  | 900 |  |  |  |
| act | agc | aca | cac | gac | ggt | gta | gcc | att | gcc | tat | gca | aca | tta | cag | cat | 2850 |
| Thr | Ser | Thr | His | Asp | Gly | Val | Ala | Ile | Ala | Tyr | Ala | Thr | Leu | Gln | His |  |
|  |  |  |  | 905 |  |  |  | 910 |  |  |  | 915 |  |  |  |
| ctc | cta | gca | gaa | aag | aga | tgt | ttg | gtt | ctt | ttt | gtc | acg | cat | tac | cct | 2898 |
| Leu | Leu | Ala | Glu | Lys | Arg | Cys | Leu | Val | Leu | Phe | Val | Thr | His | Tyr | Pro |  |
|  |  |  |  | 920 |  |  |  | 925 |  |  |  | 930 |  |  |  |
| gaa | ata | gct | gag | atc | agt | aac | gga | ttc | cca | ggt | tct | gtt | ggg | aca | tac | 2946 |
| Glu | Ile | Ala | Glu | Ile | Ser | Asn | Gly | Phe | Pro | Gly | Ser | Val | Gly | Thr | Tyr |  |
|  |  |  |  | 935 |  |  |  | 940 |  |  |  | 945 |  |  |  |
| cat | gtc | tcg | tat | ctg | aca | ttg | cag | aag | gat | aaa | ggc | agt | tat | gat | cat | 2994 |
| His | Val | Ser | Tyr | Leu | Thr | Leu | Gln | Lys | Asp | Lys | Gly | Ser | Tyr | Asp | His |  |
| 950 |  |  |  |  |  | 955 |  |  |  | 960 |  |  |  | 965 |  |  |
| gat | gat | gtg | acc | tac | cta | tat | aag | ctt | gtg | cgt | ggt | ctt | tgc | agc | agg | 3042 |
| Asp | Asp | Val | Thr | Tyr | Leu | Tyr | Lys | Leu | Val | Arg | Gly | Leu | Cys | Ser | Arg |  |
|  |  |  |  | 970 |  |  |  | 975 |  |  |  | 980 |  |  |  |
| agc | ttt | ggt | ttt | aag | gtt | gct | cag | ctt | gcc | cag | ata | cct | cca | tca | tgt | 3090 |
| Ser | Phe | Gly | Phe | Lys | Val | Ala | Gln | Leu | Ala | Gln | Ile | Pro | Pro | Ser | Cys |  |
|  |  |  |  | 985 |  |  |  | 990 |  |  |  | 995 |  |  |  |
| ata | cgt | cga | gcc | att | tca | atg | gct | gca | aaa | ttg | gaa | gct | gag | gta | cgt | 3138 |
| Ile | Arg | Arg | Ala | Ile | Ser | Met | Ala | Ala | Lys | Leu | Glu | Ala | Glu | Val | Arg |  |
|  |  |  |  | 1000 |  |  |  | 1005 |  |  |  | 1010 |  |  |  |
| gca | aga | gag | aga | aat | aca | cgc | atg | gga | gaa | cca | gaa | gga | cat | gaa | gaa | 3186 |
| Ala | Arg | Glu | Arg | Asn | Thr | Arg | Met | Gly | Glu | Pro | Glu | Gly | His | Glu | Glu |  |
|  |  |  |  | 1015 |  |  |  | 1020 |  |  |  | 1025 |  |  |  |
| ccg | aga | ggc | gca | gaa | gaa | tct | att | tcg | gct | cta | ggt | gac | ttg | ttt | gca | 3234 |
| Pro | Arg | Gly | Ala | Glu | Glu | Ser | Ile | Ser | Ala | Leu | Gly | Asp | Leu | Phe | Ala |  |
| 1030 |  |  |  |  |  | 1035 |  |  |  | 1040 |  |  |  | 1045 |  |  |
| gac | ctg | aaa | ttt | gct | ctc | tct | gaa | gag | gac | cct | tgg | aaa | gca | ttc | gag | 3282 |
| Asp | Leu | Lys | Phe | Ala | Leu | Ser | Glu | Glu | Asp | Pro | Trp | Lys | Ala | Phe | Glu |  |
|  |  |  |  | 1050 |  |  |  | 1055 |  |  |  | 1060 |  |  |  |
| ttt | tta | aag | cat | gct | tgg | aag | att | gct | ggc | aaa | atc | aga | cta | aaa | cca | 3330 |
| Phe | Leu | Lys | His | Ala | Trp | Lys | Ile | Ala | Gly | Lys | Ile | Arg | Leu | Lys | Pro |  |
|  |  |  |  | 1065 |  |  |  | 1070 |  |  |  | 1075 |  |  |  |
| act | tgt | tca | ttt | tgatttaatc | ttaacattat | agcaactgca | aggtcttgat |  |  |  |  |  |  |  |  | 3382 |
| Thr | Cys | Ser | Phe |  |  |  |  |  |  |  |  |  |  |  |  |  |
|  |  |  | 1080 |  |  |  |  |  |  |  |  |  |  |  |  |  | catctgttag ttgcgtacta acttatgtgt attagtataa caagaaaaga gaattagaga 3442 gatggattct aatccggtgt tgcagtacat cttttctcca cccgcataaa aaaaaaaaa 3502 aaaaaaaaaa aaaaaaaaaa 3522

<210> SEQ ID NO 19
<211> LENGTH: 1081
<212> TYPE: PRT
<213> ORGANISM: Arabidopsis thaliana ecotype Columbia
<220> FEATURE:
<223> OTHER INFORMATION: Polypeptide MSH3

<400> SEQUENCE: 19

Met Gly Lys Gln Lys Gln Gln Thr Ile Ser Arg Phe Phe Ala Pro Lys
1               5                   10                  15

Pro Lys Ser Pro Thr His Glu Pro Asn Pro Val Ala Glu Ser Ser Thr
            20                  25                  30

Pro Pro Pro Lys Ile Ser Ala Thr Val Ser Phe Ser Pro Ser Lys Arg
        35                  40                  45

Lys Leu Leu Ser Asp His Leu Ala Ala Ala Ser Pro Lys Lys Pro Lys
    50                  55                  60

Leu Ser Pro His Thr Gln Asn Pro Val Pro Asp Pro Asn Leu His Gln

```
                65                      70                      75                      80
Arg Phe Leu Gln Arg Phe Leu Glu Pro Ser Pro Glu Tyr Val Pro
                    85                      90                      95
Glu Thr Ser Ser Ser Arg Lys Tyr Thr Pro Leu Glu Gln Val Val
                100                     105                     110
Glu Leu Lys Ser Lys Tyr Pro Asp Val Val Leu Met Val Glu Val Gly
            115                     120                     125
Tyr Arg Tyr Arg Phe Phe Gly Glu Asp Ala Glu Ile Ala Ala Arg Val
        130                     135                     140
Leu Gly Ile Tyr Ala His Met Asp His Asn Phe Met Thr Ala Ser Val
145                     150                     155                     160
Pro Thr Phe Arg Leu Asn Phe His Val Arg Arg Leu Val Asn Ala Gly
                165                     170                     175
Tyr Lys Ile Gly Val Val Lys Gln Thr Glu Thr Ala Ala Ile Lys Ser
                180                     185                     190
His Gly Ala Asn Arg Thr Gly Pro Phe Phe Arg Gly Leu Ser Ala Leu
                195                     200                     205
Tyr Thr Lys Ala Thr Leu Glu Ala Ala Glu Asp Ile Ser Gly Gly Cys
        210                     215                     220
Gly Gly Glu Gly Phe Gly Ser Gln Ser Asn Phe Leu Val Cys Val
225                     230                     235                     240
Val Asp Glu Arg Val Lys Ser Glu Thr Leu Gly Cys Gly Ile Glu Met
                245                     250                     255
Ser Phe Asp Val Arg Val Gly Val Val Gly Val Glu Ile Ser Thr Gly
                260                     265                     270
Glu Val Val Tyr Glu Glu Phe Asn Asp Asn Phe Met Arg Ser Gly Leu
            275                     280                     285
Glu Ala Val Ile Leu Ser Leu Ser Pro Ala Glu Leu Leu Leu Gly Gln
        290                     295                     300
Pro Leu Ser Gln Gln Thr Glu Lys Phe Leu Val Ala Met Ala Gly Pro
305                     310                     315                     320
Thr Ser Asn Val Arg Val Glu Arg Ala Ser Leu Asp Cys Phe Ser Asn
                325                     330                     335
Gly Asn Ala Val Asp Glu Val Ile Ser Leu Cys Glu Lys Ile Ser Ala
            340                     345                     350
Gly Asn Leu Glu Asp Asp Lys Glu Met Lys Leu Glu Ala Ala Glu Lys
            355                     360                     365
Gly Met Ser Cys Leu Thr Val His Thr Ile Met Asn Met Pro His Leu
    370                     375                     380
Thr Val Gln Ala Leu Ala Leu Thr Phe Cys His Leu Lys Gln Phe Gly
385                     390                     395                     400
Phe Glu Arg Ile Leu Tyr Gln Gly Ala Ser Phe Arg Ser Leu Ser Ser
                405                     410                     415
Asn Thr Glu Met Thr Leu Ser Ala Asn Thr Leu Gln Gln Leu Glu Val
                420                     425                     430
Val Lys Asn Asn Ser Asp Gly Ser Glu Ser Gly Ser Leu Phe His Asn
        435                     440                     445
Met Asn His Thr Leu Thr Val Tyr Gly Ser Arg Leu Leu Arg His Trp
        450                     455                     460
Val Thr His Pro Leu Cys Asp Arg Asn Leu Ile Ser Ala Arg Leu Asp
465                     470                     475                     480
Ala Val Ser Glu Ile Ser Ala Cys Met Gly Ser His Ser Ser Ser Gln
                485                     490                     495
```

-continued

```
Leu Ser Ser Glu Leu Val Glu Gly Ser Glu Arg Ala Ile Val Ser
            500                 505                 510

Pro Glu Phe Tyr Leu Val Leu Ser Ser Val Leu Thr Ala Met Ser Arg
        515                 520                 525

Ser Ser Asp Ile Gln Arg Gly Ile Thr Arg Ile Phe His Arg Thr Ala
    530                 535                 540

Lys Ala Thr Glu Phe Ile Ala Val Met Glu Ala Ile Leu Leu Ala Gly
545                 550                 555                 560

Lys Gln Ile Gln Arg Leu Gly Ile Lys Gln Asp Ser Glu Met Arg Ser
                565                 570                 575

Met Gln Ser Ala Thr Val Arg Ser Thr Leu Leu Arg Lys Leu Ile Ser
            580                 585                 590

Val Ile Ser Ser Pro Val Val Asp Asn Ala Gly Lys Leu Leu Ser
        595                 600                 605

Ala Leu Asn Lys Glu Ala Ala Val Arg Gly Asp Leu Leu Asp Ile Leu
    610                 615                 620

Ile Thr Ser Ser Asp Gln Phe Pro Glu Leu Ala Glu Ala Arg Gln Ala
625                 630                 635                 640

Val Leu Val Ile Arg Glu Lys Leu Asp Ser Ser Ile Ala Ser Phe Arg
                645                 650                 655

Lys Lys Leu Ala Ile Arg Asn Leu Glu Phe Leu Gln Val Ser Gly Ile
            660                 665                 670

Thr His Leu Ile Glu Leu Pro Val Asp Ser Lys Val Pro His Asn Trp
        675                 680                 685

Val Lys Val Asn Ser Thr Lys Lys Thr Ile Arg Tyr His Pro Pro Glu
    690                 695                 700

Ile Val Ala Gly Leu Asp Glu Leu Ala Leu Ala Thr Glu His Leu Ala
705                 710                 715                 720

Ile Val Asn Arg Ala Ser Trp Asp Ser Phe Leu Lys Ser Phe Ser Arg
                725                 730                 735

Tyr Tyr Thr Asp Phe Lys Ala Ala Val Gln Ala Leu Ala Ala Leu Asp
            740                 745                 750

Cys Leu His Ser Leu Ser Thr Leu Ser Arg Asn Lys Asn Tyr Val Arg
        755                 760                 765

Pro Glu Phe Val Asp Asp Cys Glu Pro Val Glu Ile Asn Ile Gln Ser
    770                 775                 780

Gly Arg His Pro Val Leu Glu Thr Ile Leu Gln Asp Asn Phe Val Pro
785                 790                 795                 800

Asn Asp Thr Ile Leu His Ala Glu Gly Glu Tyr Cys Gln Ile Ile Thr
                805                 810                 815

Gly Pro Asn Met Gly Gly Lys Ser Cys Tyr Ile Arg Gln Val Ala Leu
            820                 825                 830

Ile Ser Ile Met Ala Gln Val Gly Ser Phe Val Pro Ala Ser Phe Ala
        835                 840                 845

Lys Leu His Val Leu Asp Gly Val Phe Thr Arg Met Gly Ala Ser Asp
    850                 855                 860

Ser Ile Gln His Gly Arg Ser Thr Phe Leu Glu Glu Leu Ser Glu Ala
865                 870                 875                 880

Ser His Ile Ile Arg Thr Cys Ser Ser Arg Ser Leu Val Ile Leu Asp
                885                 890                 895

Glu Leu Gly Arg Gly Thr Ser Thr His Asp Gly Val Ala Ile Ala Tyr
            900                 905                 910
```

-continued

```
Ala Thr Leu Gln His Leu Ala Glu Lys Arg Cys Leu Val Leu Phe
        915                 920                 925
Val Thr His Tyr Pro Glu Ile Ala Glu Ile Ser Asn Gly Phe Pro Gly
    930                 935                 940
Ser Val Gly Thr Tyr His Val Ser Tyr Leu Thr Leu Gln Lys Asp Lys
945                 950                 955                 960
Gly Ser Tyr Asp His Asp Asp Val Thr Tyr Leu Tyr Lys Leu Val Arg
                965                 970                 975
Gly Leu Cys Ser Arg Ser Phe Gly Phe Lys Val Ala Gln Leu Ala Gln
            980                 985                 990
Ile Pro Pro Ser Cys Ile Arg Arg Ala Ile Ser Met Ala Ala Lys Leu
        995                 1000                1005
Glu Ala Glu Val Arg Ala Arg Glu Arg Asn Thr Arg Met Gly Glu Pro
    1010                1015                1020
Glu Gly His Glu Glu Pro Arg Gly Ala Glu Glu Ser Ile Ser Ala Leu
1025                1030                1035                1040
Gly Asp Leu Phe Ala Asp Leu Lys Phe Ala Leu Ser Glu Glu Asp Pro
                1045                1050                1055
Trp Lys Ala Phe Glu Phe Leu Lys His Ala Trp Lys Ile Ala Gly Lys
            1060                1065                1070
Ile Arg Leu Lys Pro Thr Cys Ser Phe
        1075                1080
```

<210> SEQ ID NO 20
<211> LENGTH: 24
<212> TYPE: DNA
<213> ORGANISM: Artificial Sequence
<220> FEATURE:
<223> OTHER INFORMATION: MSH6 specific primer 638 for PCR using cDNA of
      Arabidopsis thaliana ecotype Columbia.

<400> SEQUENCE: 20
tctctaccag gtgacgaaaa accg                                          24

<210> SEQ ID NO 21
<211> LENGTH: 28
<212> TYPE: DNA
<213> ORGANISM: Artificial Sequence
<220> FEATURE:
<223> OTHER INFORMATION: Primer S81 for PCR using cDNA of Arabidopsis
      thaliana ecotype Columbia.

<400> SEQUENCE: 21
cgtcgccttt agcatcccct tccttcac                                      28

<210> SEQ ID NO 22
<211> LENGTH: 30
<212> TYPE: DNA
<213> ORGANISM: Artificial Sequence
<220> FEATURE:
<223> OTHER INFORMATION: MSH6 specific primer S823 for PCR using cDNA of
      Arabidopsis thaliana ecotype Columbia.

<400> SEQUENCE: 22
gcttggcgca tctaatagaa tcatgacagg                                    30

<210> SEQ ID NO 23
<211> LENGTH: 24
<212> TYPE: DNA
<213> ORGANISM: Artificial Sequence
<220> FEATURE:
<223> OTHER INFORMATION: MSH6 specific primer 637 for PCR using cDNA of Arabidopsis thaliana ecotype Columbia.

<400> SEQUENCE: 23
gacagcgtca gttcttcaga atgc                                          24

<210> SEQ ID NO 24
<211> LENGTH: 33
<212> TYPE: DNA
<213> ORGANISM: Artificial Sequence
<220> FEATURE:
<223> OTHER INFORMATION: MSH6 specific primer 1S8 for PCR using cDNA of
      Arabidopsis thaliana ecotype Columbia.

<400> SEQUENCE: 24
atcccgggat gcagcgccag agatcgattt tgt                                33

<210> SEQ ID NO 25
<211> LENGTH: 27
<212> TYPE: DNA
<213> ORGANISM: Artificial Sequence
<220> FEATURE:
<223> OTHER INFORMATION: MSH6 specific primer S83 for PCR using cDNA of
      Arabidopsis thaliana ecotype Columbia.

<400> SEQUENCE: 25
cgctatctat ggctgcttcg aattgag                                       27

<210> SEQ ID NO 26
<211> LENGTH: 2188
<212> TYPE: DNA
<213> ORGANISM: Arabidopsis thaliana ecotype Columbia
<220> FEATURE:
<221> NAME/KEY: misc_feature
<222> LOCATION: (0)...(0)
<223> OTHER INFORMATION: Clone 43

<400> SEQUENCE: 26
cccgggatgc agcgccagag atcgattttg tctttcttcc aaaaacccac ggcggcgact     60
acgaagggtt tggtttccgg cgatgctgct agcggcgggg gcggcagcgg aggaccacga    120
tttaatgtga aggaagggga tgctaaaggc gacgcttctg tacgttttgc tgtttcgaaa    180
tctgtcgatg aggttagagg aacggatact ccaccggaga aggttccgcg tcgtgtcctg    240
ccgtctggat ttaagccggc tgaatccgcc ggtgatgctt cgtccctgtt ctccaatatt    300
atgcataagt ttgtaaaagt cgatgatcga gattgttctg gagagaggag ccgagaagat    360
gttgttccgc tgaatgattc atctctatgt atgaaggcta atgatgttat tcctcaattt    420
cgttccaata atggtaaaac tcaagaaaga aaccatgctt ttagtttcag tgggagagct    480
gaacttagat cagtagaaga tataggagta gatggcgatg ttcctggtcc agaaacacca    540
gggatgcgtc cacgtgcttc tcgcttgaag cgagttctgg aggatgaaat gacttttaag    600
gaggataagg ttcctgtatt ggactctaac aaaaggctga aaatgctcca ggatccggtt    660
tgtggagaga agaagaagt aaacgaagga accaaatttg aatggcttga gtcttctcga    720
atcagggatg ccaatagaag acgtcctgat gatccccttt acgatagaaa gaccttacac    780
ataccacctg atgttttcaa gaaaatgtct gcatcacaaa agcaatattg gagtgttaag    840
agtgaatata tggacattgt gcttttcttt aaagtgggga aattttatga gctgtatgag    900
ctagatgcgg aattaggtca caggagcttg actggaaga tgaccatgag tggtgtggga    960
aaatgcagac aggttggtat ctctgaaagt gggatagatg aggcagtgca aaagctatta   1020
gctcgtggat ataaagttgg acgaatcgag cagctagaaa catctgacca agcaaaagcc   1080

-continued

```
agaggtgcta atactataat tccaaggaag ctagttcagg tattaactcc atcaacagca    1140
agcgagggaa acatcgggcc tgatgccgtc catcttcttg ctataaaaga gatcaaaatg    1200
gagctacaaa agtgttcaac tgtgtatgga tttgcttttg ttgactgtgc tgccttgagg    1260
ttttgggttg ggtccatcag cgatgatgca tcatgtgctg ctcttggagc gttattgatg    1320
caggtttctc caaggaagt gttatatgac agtaaagggc tatcaagaga agcacaaaag    1380
gctctaagga aatatacgtt gacagggtct acggcggtac agttggctcc agtaccacaa    1440
gtaatggggg atacagatgc tgctggagtt agaaatataa tagaatctaa cggatacttt    1500
aaaggttctt ctgaatcatg gaactgtgct gttgatggtc taaatgaatg tgatgttgcc    1560
cttagtgctc ttggagagct aattaatcat ctgtctaggc taaagctaga agatgtactt    1620
aagcatgggg atattttcc ataccaagtt tacaggggtt gtctcagaat tgatggccag    1680
acgatggtaa atcttgagat atttaacaat agctgtgatg tggtccttc agggaccttg    1740 tacaaatatc ttgataactg tgttagtcca actggtaagc gactcttaag gaattggatc    1800
tgccatccac tcaagatgt agaaagcatc aataaacggc ttgatgtagt tgaagaattc    1860
acggcaaact cagaaagtat gcaaatcact ggccagtatc tccacaaact tccagactta    1920
gaaagactgc tcggacgcat caagtctagc gttcgatcat cagcctctgt gttgcctgct    1980
cttctgggga aaaagtgct gaaacaacga gttaaagcat ttgggcaaat tgtgaagggg    2040
ttcagaagtg gaattgatct gttgttggct ctacagaagg aatcaaatat gatgagtttg    2100
ctttataaac tctgtaaact tcctatatta gtaggaaaaa gcgggctaga gttatttctt    2160
tctcaattcg aagcagccat agatagcg                                      2188
```

<210> SEQ ID NO 27
<211> LENGTH: 1385
<212> TYPE: DNA
<213> ORGANISM: Arabidopsis thaliana ecotype Columbia
<220> FEATURE:
<221> NAME/KEY: misc_feature
<222> LOCATION: (0)...(0)
<223> OTHER INFORMATION: Clone 62

<400> SEQUENCE: 27

```
catcagcctc tgtgttgcct gctcttctgg ggaaaaaagt gctgaaacaa cgagttaaag     60
catttgggca aattgtgaaa gggttcagaa gtggaattga tctgttgttg gctctacaga    120
aggaatcaaa tatgatgagt ttgctttata aactctgtaa acttcctata ttagtaggaa    180
aaagcgggct agagttattt ctttctcaat tcgaagcagc catagatagc gacttttccaa    240 attatcagaa ccaagatgtg acagatgaaa acgctgaaac tctcacaata cttatcgaac    300
tttttatcga aagagcaact caatggtctg aggtcattca caccataagc tgcctagatg    360
tcctgagatc ttttgcaatc gcagcaagtc tctctgctgg aagcatggcc aggcctgtta    420 ttttcccga atcagaagct acagatcaga atcagaaaac aaaagggcca atacttaaaa    480
tccaaggact atggcatcca tttgcagttg cagccgatgg tcaattgcct gttccgaatg    540
atatactcct tggcgaggct agaagaagca gtggcagcat tcatcctcgg tcattgttac    600
tgacgggacc aaacatgggc ggaaaatcaa ctcttcttcg tgcaacatgt ctggccgtta    660
tctttgccca acttggctgc tacgtgccgt gtgagtcttg cgaaatctcc ctcgtggata    720
ctatcttcac aaggcttggc gcatctgata gaatcatgac aggagagagt acctttttgg    780
tagaatgcac tgagacagcg tcagttcttc agaatgcaac tcaggattca ctagtaatcc    840
```

```
ttgacgaact gggcagagga actagtactt tcgatggata cgccattgca tactcggttt      900
ttcgtcacct ggtagagaaa gttcaatgtc ggatgctctt tgcaacacat taccaccctc     960
tcaccaagga attcgcgtct cacccacgtg tcacctcgaa acacatggct tgcgcattca     1020
aatcaagatc tgattatcaa ccacgtggtt gtgatcaaga cctagtgttc ttgtaccgtt     1080
taaccgaggg agcttgtcct gagagctacg gacttcaagt ggcactcatg gctggaatac     1140
caaaccaagt ggttgaaaca gcatcaggtg ctgctcaagc catgaagaga tcaattgggg     1200
aaaacttcaa gtcaagtgag ctaagatctg agttctcaag tctgcatgaa gactggctca     1260
agtcattggt gggtatttct cgagtcgccc acaacaatgc ccccattggc gaagatgact     1320
acgacacttt gttttgctta tggcatgaga tcaaatcctc ttactgtgtt cccaaataac     1380
ccggg                                                                 1385

<210> SEQ ID NO 28
<211> LENGTH: 34
<212> TYPE: DNA
<213> ORGANISM: Artificial Sequence
<220> FEATURE:
<223> OTHER INFORMATION: MSH6 specific primer 2S8 for PCR using cDNA of
      Arabidopsis thaliana ecotype Columbia.

<400> SEQUENCE: 28
atcccgggtt atttgggaac acagtaagag gatt                                   34

<210> SEQ ID NO 29
<211> LENGTH: 27
<212> TYPE: DNA
<213> ORGANISM: Artificial Sequence
<220> FEATURE:
<223> OTHER INFORMATION: MSH6 specific primer S82 for PCR using cDNA of
      Arabidopsis thaliana ecotype Columbia.

<400> SEQUENCE: 29
gcgttcgatc atcagcctct gtgttgc                                           27

<210> SEQ ID NO 30
<211> LENGTH: 3606
<212> TYPE: DNA
<213> ORGANISM: Arabidopsis thaliana ecotype Columbia
<220> FEATURE:
<221> NAME/KEY: CDS
<222> LOCATION: (142)...(3468)
<223> OTHER INFORMATION: AtMSH6 full-length cDNA and deduced sequence of
      the encoded polypeptide.

<400> SEQUENCE: 30
aaaagttgag ccctgaggag tatcgttttcc gccatttcta cgacgcaagg cgaaaatttt     60
tggcgccaat ctttcccccc tttcgaattc tctcagctca aaacatcgtt tctctctcac    120
tctctctcac aattccaaaa a atg cag cgc cag aga tcg att ttg tct ttc      171
                        Met Gln Arg Gln Arg Ser Ile Leu Ser Phe
                         1               5                  10 ttc caa aaa ccc acc gcg gcg act acg aag ggt ttg gtt tcc ggc gat      219
Phe Gln Lys Pro Thr Ala Ala Thr Thr Lys Gly Leu Val Ser Gly Asp
             15                  20                  25 gct gct agc ggc ggg ggc ggc agc gga gga cca cga ttt aat gtg aag      267
Ala Ala Ser Gly Gly Gly Gly Ser Gly Gly Pro Arg Phe Asn Val Lys
         30                  35                  40 gaa ggg gat gct aaa ggc gac gct tct gta cgt ttt gct gtt tcg aaa      315
Glu Gly Asp Ala Lys Gly Asp Ala Ser Val Arg Phe Ala Val Ser Lys
     45                  50                  55
```

-continued

| | |
|---|---|
| tct gtc gat gag gtt aga gga acg gat act cca ccg gag aag gtt ccg<br>Ser Val Asp Glu Val Arg Gly Thr Asp Thr Pro Pro Glu Lys Val Pro<br>60                       65                     70 | 363 |
| cgt cgt gtc ctg ccg tct gga ttt aag ccg gct gaa tcc gcc gst gat<br>Arg Arg Val Leu Pro Ser Gly Phe Lys Pro Ala Glu Ser Ala Gly Asp<br>75                       80                     85                     90 | 411 |
| gct tcg tcc ctg ttc tcc aat att atg cat aag ttt gta aaa gtc gat<br>Ala Ser Ser Leu Phe Ser Asn Ile Met His Lys Phe Val Lys Val Asp<br>                 95                    100                   105 | 459 |
| gat cga gat tgt tct gga gag agg agc cga gaa gat gtt gtt ccg ctg<br>Asp Arg Asp Cys Ser Gly Glu Arg Ser Arg Glu Asp Val Val Pro Leu<br>         110                    115                   120 | 507 |
| aat gat tca tct cta tgt atg aag gct aat gat gtt att cct caa ttt<br>Asn Asp Ser Ser Leu Cys Met Lys Ala Asn Asp Val Ile Pro Gln Phe<br>               125                   130                   135 | 555 |
| cgt tcc aat aat ggt aaa act caa gaa aga aac cat gct ttt agt ttc<br>Arg Ser Asn Asn Gly Lys Thr Gln Glu Arg Asn His Ala Phe Ser Phe<br>140                      145                     150 | 603 |
| agt ggg aga gct gaa ctt aga tca gta gaa gat ata gga gta gat ggc<br>Ser Gly Arg Ala Glu Leu Arg Ser Val Glu Asp Ile Gly Val Asp Gly<br>155                      160                    165                 170 | 651 |
| gat gtt cct ggt cca gaa aca cca ggg atg cgt cca cgt gct tct cgc<br>Asp Val Pro Gly Pro Glu Thr Pro Gly Met Arg Pro Arg Ala Ser Arg<br>               175                   180                   185 | 699 |
| ttg aag cga gtt ctg gag gat gaa atg act ttt aag gag gat aag gtt<br>Leu Lys Arg Val Leu Glu Asp Glu Met Thr Phe Lys Glu Asp Lys Val<br>         190                    195                   200 | 747 |
| cct gta ttg gac tct aac aaa agg ctg aaa atg ctc cag gat ccg gtt<br>Pro Val Leu Asp Ser Asn Lys Arg Leu Lys Met Leu Gln Asp Pro Val<br>205                      210                    215 | 795 |
| tgt gga gag aag aaa gaa gta aac gaa gga acc aaa ttt gaa tgg ctt<br>Cys Gly Glu Lys Lys Glu Val Asn Glu Gly Thr Lys Phe Glu Trp Leu<br>220                      225                    230 | 843 |
| gag tct tct cga atc agg gat gcc aat aga aga cgt cct gat gat ccc<br>Glu Ser Ser Arg Ile Arg Asp Ala Asn Arg Arg Arg Pro Asp Asp Pro<br>235                      240                    245                   250 | 891 |
| ctt tac gat aga aag acc tta cac ata cca cct gat gtt ttc aag aaa<br>Leu Tyr Asp Arg Lys Thr Leu His Ile Pro Pro Asp Val Phe Lys Lys<br>               255                   260                   265 | 939 |
| atg tct gca tca caa aag caa tat tgg agt gtt aag agt gaa tat atg<br>Met Ser Ala Ser Gln Lys Gln Tyr Trp Ser Val Lys Ser Glu Tyr Met<br>         270                    275                   280 | 987 |
| gac att gtg ctt ttc ttt aaa gtg ggg aaa ttt tat gag ctg tat gag<br>Asp Ile Val Leu Phe Phe Lys Val Gly Lys Phe Tyr Glu Leu Tyr Glu<br>285                      290                    295 | 1035 |
| cta gat gcg gaa tta ggt cac aag gag ctt gac tgg aag atg acc atg<br>Leu Asp Ala Glu Leu Gly His Lys Glu Leu Asp Trp Lys Met Thr Met<br>300                      305                    310 | 1083 |
| agt ggt gtg gga aaa tgc aga cag gtt ggt atc tct gaa agt ggg ata<br>Ser Gly Val Gly Lys Cys Arg Gln Val Gly Ile Ser Glu Ser Gly Ile<br>315                      320                    325                 330 | 1131 |
| gat gag gca gtg caa aag cta tta gct cgt gga tat aaa gtt gga cga<br>Asp Glu Ala Val Gln Lys Leu Leu Ala Arg Gly Tyr Lys Val Gly Arg<br>               335                   340                   345 | 1179 |
| atc gag cag cta gaa aca tct gac caa gca aaa gcc aga ggt gct aat<br>Ile Glu Gln Leu Glu Thr Ser Asp Gln Ala Lys Ala Arg Gly Ala Asn<br>         350                    355                   360 | 1227 |
| act ata att cca agg aag cta gtt cag gta tta act cca tca aca gca<br>Thr Ile Ile Pro Arg Lys Leu Val Gln Val Leu Thr Pro Ser Thr Ala<br>365                      370                    375 | 1275 |

-continued

| | | |
|---|---|---|
| agc gag gga aac atc ggg cct gat gcc gtc cat ctt ctt gct ata aaa<br>Ser Glu Gly Asn Ile Gly Pro Asp Ala Val His Leu Leu Ala Ile Lys<br>380                           385                        390 | 1323 |
| gag atc aaa atg gag cta caa aag tgt tca act gtg tat gga ttt gct<br>Glu Ile Lys Met Glu Leu Gln Lys Cys Ser Thr Val Tyr Gly Phe Ala<br>395                           400                        405                    410 | 1371 |
| ttt gtt gac tgt gct gcc ttg agg ttt tgg gtt ggg tcc atc agc gat<br>Phe Val Asp Cys Ala Ala Leu Arg Phe Trp Val Gly Ser Ile Ser Asp<br>                      415                        420                    425 | 1419 |
| gat gca tca tgt gct gct ctt gga gcg tta ttg atg cag gtt tct cca<br>Asp Ala Ser Cys Ala Ala Leu Gly Ala Leu Leu Met Gln Val Ser Pro<br>                  430                        435                    440 | 1467 |
| aag gaa gtg tta tat gac agt aaa ggg cta tca aga gaa gca caa aag<br>Lys Glu Val Leu Tyr Asp Ser Lys Gly Leu Ser Arg Glu Ala Gln Lys<br>                      445                        450                    455 | 1515 |
| gct cta agg aaa tat acg ttg aca ggg tct acg gcg gta cag ttg gct<br>Ala Leu Arg Lys Tyr Thr Leu Thr Gly Ser Thr Ala Val Gln Leu Ala<br>460                           465                        470 | 1563 |
| cca gta cca caa gta atg ggg gat aca gat gct gct gga gtt aga aat<br>Pro Val Pro Gln Val Met Gly Asp Thr Asp Ala Ala Gly Val Arg Asn<br>475                           480                        485                    490 | 1611 |
| ata ata gaa tct aac gga tac ttt aaa ggt tct tct gaa tca tgg aac<br>Ile Ile Glu Ser Asn Gly Tyr Phe Lys Gly Ser Ser Glu Ser Trp Asn<br>                      495                        500                    505 | 1659 |
| tgt gct gtt gat ggt cta aat gaa tgt gat gtt gcc ctt agt gct ctt<br>Cys Ala Val Asp Gly Leu Asn Glu Cys Asp Val Ala Leu Ser Ala Leu<br>                    510                        515                    520 | 1707 |
| gga gag cta att aat cat ctg tct agg cta aag cta gaa gat gta ctt<br>Gly Glu Leu Ile Asn His Leu Ser Arg Leu Lys Leu Glu Asp Val Leu<br>                525                        530                    535 | 1755 |
| aag cat ggg gat att ttt cca tac caa gtt tac agg ggt tgt ctc aga<br>Lys His Gly Asp Ile Phe Pro Tyr Gln Val Tyr Arg Gly Cys Leu Arg<br>540                           545                        550 | 1803 |
| att gat ggc cag acg atg gta aat ctt gag ata ttt aac aat agc tgt<br>Ile Asp Gly Gln Thr Met Val Asn Leu Glu Ile Phe Asn Asn Ser Cys<br>555                           560                        565                    570 | 1851 |
| gat ggt ggt cct tca ggg acc ttg tac aaa tat ctt gat aac tgt gtt<br>Asp Gly Gly Pro Ser Gly Thr Leu Tyr Lys Tyr Leu Asp Asn Cys Val<br>                    575                        580                    585 | 1899 |
| agt cca act ggt aag cga ctc tta agg aat tgg atc tgc cat cca ctc<br>Ser Pro Thr Gly Lys Arg Leu Leu Arg Asn Trp Ile Cys His Pro Leu<br>                590                        595                    600 | 1947 |
| aaa gat gta gaa agc atc aat aaa cgg ctt gat gta gtt gaa gaa ttc<br>Lys Asp Val Glu Ser Ile Asn Lys Arg Leu Asp Val Val Glu Glu Phe<br>605                           610                        615 | 1995 |
| acg gca aac tca gaa agt atg caa atc act ggc cag tat ctc cac aaa<br>Thr Ala Asn Ser Glu Ser Met Gln Ile Thr Gly Gln Tyr Leu His Lys<br>                    620                        625                    630 | 2043 |
| ctt cca gac tta gaa aga ctg ctc gga cgc atc aag tct agc gtt cga<br>Leu Pro Asp Leu Glu Arg Leu Leu Gly Arg Ile Lys Ser Ser Val Arg<br>635                           640                        645                    650 | 2091 |
| tca tca gcc tct gtg ttg cct gct ctt ctg ggg aaa aaa gtg ctg aaa<br>Ser Ser Ala Ser Val Leu Pro Ala Leu Leu Gly Lys Lys Val Leu Lys<br>                    655                        660                    665 | 2139 |
| caa cga gtt aaa gca ttt ggg caa att gtg aaa ggg ttc aga agt gga<br>Gln Arg Val Lys Ala Phe Gly Gln Ile Val Lys Gly Phe Arg Ser Gly<br>                    670                        675                    680 | 2187 |
| att gat ctg ttg ttg gct cta cag aag gaa tca aat atg atg agt ttg<br>Ile Asp Leu Leu Leu Ala Leu Gln Lys Glu Ser Asn Met Met Ser Leu | 2235 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 685 |     |     |     |     | 690 |     |     |     |     |     | 695 |     |     |      |
| ctt | tat | aaa | ctc | tgt | aaa | ctt | cct | ata | tta | gta | gga | aaa | agc | ggg | cta | 2283 |
| Leu | Tyr | Lys | Leu | Cys | Lys | Leu | Pro | Ile | Leu | Val | Gly | Lys | Ser | Gly | Leu |      |
|     | 700 |     |     |     | 705 |     |     |     |     | 710 |     |     |     |     |     |      |
| gag | tta | ttt | ctt | tct | caa | ttc | gaa | gca | gcc | ata | gat | agc | gac | ttt | cca | 2331 |
| Glu | Leu | Phe | Leu | Ser | Gln | Phe | Glu | Ala | Ala | Ile | Asp | Ser | Asp | Phe | Pro |      |
| 715 |     |     |     |     | 720 |     |     |     |     | 725 |     |     |     |     | 730 |      |
| aat | tat | cag | aac | caa | gat | gtg | aca | gat | gaa | aac | gct | gaa | act | ctc | aca | 2379 |
| Asn | Tyr | Gln | Asn | Gln | Asp | Val | Thr | Asp | Glu | Asn | Ala | Glu | Thr | Leu | Thr |      |
|     |     |     |     | 735 |     |     |     |     | 740 |     |     |     |     | 745 |     |      |
| ata | ctt | atc | gaa | ctt | ttt | atc | gaa | aga | gca | act | caa | tgg | tct | gag | gtc | 2427 |
| Ile | Leu | Ile | Glu | Leu | Phe | Ile | Glu | Arg | Ala | Thr | Gln | Trp | Ser | Glu | Val |      |
|     |     |     | 750 |     |     |     |     | 755 |     |     |     |     | 760 |     |     |      |
| att | cac | acc | ata | agc | tgc | cta | gat | gtc | ctg | aga | tct | ttt | gca | atc | gca | 2475 |
| Ile | His | Thr | Ile | Ser | Cys | Leu | Asp | Val | Leu | Arg | Ser | Phe | Ala | Ile | Ala |      |
|     |     | 765 |     |     |     |     | 770 |     |     |     |     | 775 |     |     |     |      |
| gca | agt | ctc | tct | gct | gga | agc | atg | gcc | agg | cct | gtt | att | ttt | ccc | gaa | 2523 |
| Ala | Ser | Leu | Ser | Ala | Gly | Ser | Met | Ala | Arg | Pro | Val | Ile | Phe | Pro | Glu |      |
| 780 |     |     |     |     | 785 |     |     |     |     | 790 |     |     |     |     |     |      |
| tca | gaa | gct | aca | gat | cag | aat | cag | aaa | aca | aaa | ggg | cca | ata | ctt | aaa | 2571 |
| Ser | Glu | Ala | Thr | Asp | Gln | Asn | Gln | Lys | Thr | Lys | Gly | Pro | Ile | Leu | Lys |      |
| 795 |     |     |     | 800 |     |     |     |     | 805 |     |     |     |     | 810 |     |      |
| atc | caa | gga | cta | tgg | cat | cca | ttt | gca | gtt | gca | gcc | gat | ggt | caa | ttg | 2619 |
| Ile | Gln | Gly | Leu | Trp | His | Pro | Phe | Ala | Val | Ala | Ala | Asp | Gly | Gln | Leu |      |
|     |     |     |     | 815 |     |     |     |     | 820 |     |     |     |     | 825 |     |      |
| cct | gtt | ccg | aat | gat | ata | ctc | ctt | ggc | gag | gct | aga | aga | agc | agt | ggc | 2667 |
| Pro | Val | Pro | Asn | Asp | Ile | Leu | Leu | Gly | Glu | Ala | Arg | Arg | Ser | Ser | Gly |      |
|     |     |     | 830 |     |     |     |     | 835 |     |     |     |     | 840 |     |     |      |
| agc | att | cat | cct | cgg | tca | ttg | tta | ctg | acg | gga | cca | aac | atg | ggc | gga | 2715 |
| Ser | Ile | His | Pro | Arg | Ser | Leu | Leu | Leu | Thr | Gly | Pro | Asn | Met | Gly | Gly |      |
|     |     | 845 |     |     |     |     | 850 |     |     |     |     | 855 |     |     |     |      |
| aaa | tca | act | ctt | ctt | cgt | gca | aca | tgt | ctg | gcc | gtt | atc | ttt | gcc | caa | 2763 |
| Lys | Ser | Thr | Leu | Leu | Arg | Ala | Thr | Cys | Leu | Ala | Val | Ile | Phe | Ala | Gln |      |
| 860 |     |     |     |     | 865 |     |     |     |     | 870 |     |     |     |     |     |      |
| ctt | ggc | tgc | tac | gtg | ccg | tgt | gag | tct | tgc | gaa | atc | tcc | ctc | gtg | gat | 2811 |
| Leu | Gly | Cys | Tyr | Val | Pro | Cys | Glu | Ser | Cys | Glu | Ile | Ser | Leu | Val | Asp |      |
| 875 |     |     |     | 880 |     |     |     |     | 885 |     |     |     |     | 890 |     |      |
| act | atc | ttc | aca | agg | ctt | ggc | gca | tct | gat | aga | atc | atg | aca | gga | gag | 2859 |
| Thr | Ile | Phe | Thr | Arg | Leu | Gly | Ala | Ser | Asp | Arg | Ile | Met | Thr | Gly | Glu |      |
|     |     |     |     | 895 |     |     |     |     | 900 |     |     |     |     | 905 |     |      |
| agt | acc | ttt | ttg | gta | gaa | tgc | act | gag | aca | gcg | tca | gtt | ctt | cag | aat | 2907 |
| Ser | Thr | Phe | Leu | Val | Glu | Cys | Thr | Glu | Thr | Ala | Ser | Val | Leu | Gln | Asn |      |
|     |     | 910 |     |     |     |     | 915 |     |     |     |     | 920 |     |     |     |      |
| gca | act | cag | gat | tca | cta | gta | atc | ctt | gac | gaa | ctg | ggc | aga | gga | act | 2955 |
| Ala | Thr | Gln | Asp | Ser | Leu | Val | Ile | Leu | Asp | Glu | Leu | Gly | Arg | Gly | Thr |      |
|     | 925 |     |     |     |     | 930 |     |     |     |     | 935 |     |     |     |     |      |
| agt | act | ttc | gat | gga | tac | gcc | att | gca | tac | tcg | gtt | ttt | cgt | cac | ctg | 3003 |
| Ser | Thr | Phe | Asp | Gly | Tyr | Ala | Ile | Ala | Tyr | Ser | Val | Phe | Arg | His | Leu |      |
|     | 940 |     |     |     |     | 945 |     |     |     |     | 950 |     |     |     |     |      |
| gta | gag | aaa | gtt | caa | tgt | cgg | atg | ctc | ttt | gca | aca | cat | tac | cac | cct | 3051 |
| Val | Glu | Lys | Val | Gln | Cys | Arg | Met | Leu | Phe | Ala | Thr | His | Tyr | His | Pro |      |
| 955 |     |     |     | 960 |     |     |     |     | 965 |     |     |     |     | 970 |     |      |
| ctc | acc | aag | gaa | ttc | gcg | tct | cac | cca | cgt | gtc | acc | tcg | aaa | cac | atg | 3099 |
| Leu | Thr | Lys | Glu | Phe | Ala | Ser | His | Pro | Arg | Val | Thr | Ser | Lys | His | Met |      |
|     |     |     |     | 975 |     |     |     |     | 980 |     |     |     |     | 985 |     |      |
| gct | tgc | gca | ttc | aaa | tca | aga | tct | gat | tat | caa | cca | cgt | ggt | tgt | gat | 3147 |
| Ala | Cys | Ala | Phe | Lys | Ser | Arg | Ser | Asp | Tyr | Gln | Pro | Arg | Gly | Cys | Asp |      |
|     |     |     | 990 |     |     |     |     | 995 |     |     |     |     | 1000 |     |     |      |
| caa | gac | cta | gtg | ttc | ttg | tac | cgt | tta | acc | gag | gga | gct | tgt | cct | gag | 3195 |

```
Gln Asp Leu Val Phe Leu Tyr Arg Leu Thr Glu Gly Ala Cys Pro Glu
        1005                1010                1015 agc tac gga ctt caa gtg gca ctc atg gct gga ata cca aac caa gtg      3243
Ser Tyr Gly Leu Gln Val Ala Leu Met Ala Gly Ile Pro Asn Gln Val
    1020                1025                1030 gtt gaa aca gca tca ggt gct gct caa gcc atg aag aga tca att ggg      3291
Val Glu Thr Ala Ser Gly Ala Ala Gln Ala Met Lys Arg Ser Ile Gly
1035                1040                1045                1050 gga aac ttc aag tca agt gag cta aga tct gag ttc tca agt ctg cat      3339
Glu Asn Phe Lys Ser Ser Glu Leu Arg Ser Glu Phe Ser Ser Leu His
                1055                1060                1065 gaa gac tgg ctc aag tca ttg gtg ggt att tct cga gtc gcc cac aac      3387
Glu Asp Trp Leu Lys Ser Leu Val Gly Ile Ser Arg Val Ala His Asn
            1070                1075                1080 aat gcc ccc att ggc gaa gat gac tac gac act ttg ttt tgc tta tgg      3435
Asn Ala Pro Ile Gly Glu Asp Asp Tyr Asp Thr Leu Phe Cys Leu Trp
        1085                1090                1095 cat gag atc aaa tcc tct tac tgt gtt ccc aaa taaatggcta tgacataaca    3488
His Glu Ile Lys Ser Ser Tyr Cys Val Pro Lys
        1100                1105 ctatctgaag ctcgttaagt cttttgcctc tctgatgttt attcctctta aaaaatgctt   3548
atatatcaaa aaattgtttc ctcgattaaa aaaaaaaaaa aaaaaaaaaa aaaaaaa      3606

<210> SEQ ID NO 31
<211> LENGTH: 1109
<212> TYPE: PRT
<213> ORGANISM: Arabidopsis thaliana ecotype Columbia
<220> FEATURE:
<223> OTHER INFORMATION: Polypeptide MSH6

<400> SEQUENCE: 31

Met Gln Arg Gln Arg Ser Ile Leu Ser Phe Phe Gln Lys Pro Thr Ala
1               5                   10                  15

Ala Thr Thr Lys Gly Leu Val Ser Gly Asp Ala Ala Ser Gly Gly Gly
            20                  25                  30

Gly Ser Gly Gly Pro Arg Phe Asn Val Arg Glu Gly Asp Ala Lys Gly
        35                  40                  45

Asp Ala Ser Val Arg Phe Ala Val Ser Lys Ser Val Asp Glu Val Arg
    50                  55                  60

Gly Thr Asp Thr Pro Pro Glu Lys Val Pro Arg Arg Val Leu Pro Ser
65                  70                  75                  80

Gly Phe Lys Pro Ala Glu Ser Ala Gly Asp Ala Ser Ser Leu Phe Ser
                85                  90                  95

Asn Ile Met His Lys Phe Val Lys Val Asp Asp Arg Asp Cys Ser Gly
            100                 105                 110

Glu Arg Ser Arg Glu Asp Val Val Pro Leu Asn Asp Ser Ser Leu Cys
        115                 120                 125

Met Lys Ala Asn Asp Val Ile Pro Gln Phe Arg Ser Asn Asn Gly Lys
    130                 135                 140

Thr Gln Glu Arg Asn His Ala Phe Ser Phe Ser Gly Arg Ala Glu Leu
145                 150                 155                 160

Arg Ser Val Glu Asp Ile Gly Val Asp Gly Asp Val Pro Gly Pro Glu
                165                 170                 175

Thr Pro Gly Met Arg Pro Arg Ala Ser Arg Leu Lys Arg Val Leu Glu
            180                 185                 190

Asp Glu Met Thr Phe Lys Glu Asp Lys Val Pro Val Leu Asp Ser Asn
        195                 200                 205
```

-continued

```
Lys Arg Leu Lys Met Leu Gln Asp Pro Val Cys Gly Glu Lys Lys Glu
        210                 215                 220

Val Asn Glu Gly Thr Lys Phe Glu Trp Leu Glu Ser Ser Arg Ile Arg
225                 230                 235                 240

Asp Ala Asn Arg Arg Pro Asp Asp Pro Leu Tyr Asp Arg Lys Thr
            245                 250                 255

Leu His Ile Pro Pro Asp Val Phe Lys Lys Met Ser Ala Ser Gln Lys
                260                 265                 270

Gln Tyr Trp Ser Val Lys Ser Glu Tyr Met Asp Ile Val Leu Phe Phe
            275                 280                 285

Lys Val Gly Lys Phe Tyr Glu Leu Tyr Glu Leu Asp Ala Glu Leu Gly
290                 295                 300

His Lys Glu Leu Asp Trp Lys Met Thr Met Ser Gly Val Gly Lys Cys
305                 310                 315                 320

Arg Gln Val Gly Ile Ser Glu Ser Gly Ile Asp Glu Ala Val Gln Lys
                325                 330                 335

Leu Leu Ala Arg Gly Tyr Lys Val Gly Arg Ile Glu Gln Leu Glu Thr
                340                 345                 350

Ser Asp Gln Ala Lys Ala Arg Gly Ala Asn Thr Ile Ile Pro Arg Lys
            355                 360                 365

Leu Val Gln Val Leu Thr Pro Ser Thr Ala Ser Glu Gly Asn Ile Gly
370                 375                 380

Pro Asp Ala Val His Leu Leu Ala Ile Lys Glu Ile Lys Met Glu Leu
385                 390                 395                 400

Gln Lys Cys Ser Thr Val Tyr Gly Phe Ala Phe Val Asp Cys Ala Ala
                405                 410                 415

Leu Arg Phe Trp Val Gly Ser Ile Ser Asp Asp Ala Ser Cys Ala Ala
                420                 425                 430

Leu Gly Ala Leu Leu Met Gln Val Ser Pro Lys Glu Val Leu Tyr Asp
            435                 440                 445

Ser Lys Gly Leu Ser Arg Glu Ala Gln Lys Ala Leu Arg Lys Tyr Thr
        450                 455                 460

Leu Thr Gly Ser Thr Ala Val Gln Leu Ala Pro Val Pro Gln Val Met
465                 470                 475                 480

Gly Asp Thr Asp Ala Ala Gly Val Arg Asn Ile Ile Glu Ser Asn Gly
                485                 490                 495

Tyr Phe Lys Gly Ser Ser Glu Ser Trp Asn Cys Ala Val Asp Gly Leu
            500                 505                 510

Asn Glu Cys Asp Val Ala Leu Ser Ala Leu Gly Glu Leu Ile Asn His
        515                 520                 525

Leu Ser Arg Leu Lys Leu Glu Asp Val Leu Lys His Gly Asp Ile Phe
        530                 535                 540

Pro Tyr Gln Val Tyr Arg Gly Cys Leu Arg Ile Asp Gly Gln Thr Met
545                 550                 555                 560

Val Asn Leu Glu Ile Phe Asn Asn Ser Cys Asp Gly Gly Pro Ser Gly
                565                 570                 575

Thr Leu Tyr Lys Tyr Leu Asp Asn Cys Val Ser Pro Thr Gly Lys Arg
            580                 585                 590

Leu Leu Arg Asn Trp Ile Cys His Pro Leu Lys Asp Val Glu Ser Ile
        595                 600                 605

Asn Lys Arg Leu Asp Val Val Glu Glu Phe Thr Ala Asn Ser Glu Ser
610                 615                 620
```

-continued

```
Met Gln Ile Thr Gly Gln Tyr Leu His Lys Leu Pro Asp Leu Glu Arg
625                 630                 635                 640

Leu Leu Gly Arg Ile Lys Ser Ser Val Arg Ser Ser Ala Ser Val Leu
            645                 650                 655

Pro Ala Leu Leu Gly Lys Lys Val Leu Lys Gln Arg Val Lys Ala Phe
                660                 665                 670

Gly Gln Ile Val Lys Gly Phe Arg Ser Gly Ile Asp Leu Leu Leu Ala
            675                 680                 685

Leu Gln Lys Glu Ser Asn Met Met Ser Leu Leu Tyr Lys Leu Cys Lys
        690                 695                 700

Leu Pro Ile Leu Val Gly Lys Ser Gly Leu Glu Leu Phe Leu Ser Gln
705                 710                 715                 720

Phe Glu Ala Ala Ile Asp Ser Asp Phe Pro Asn Tyr Gln Asn Gln Asp
                725                 730                 735

Val Thr Asp Glu Asn Ala Glu Thr Leu Thr Ile Leu Ile Glu Leu Phe
            740                 745                 750

Ile Glu Arg Ala Thr Gln Trp Ser Glu Val Ile His Thr Ile Ser Cys
        755                 760                 765

Leu Asp Val Leu Arg Ser Phe Ala Ile Ala Ala Ser Leu Ser Ala Gly
770                 775                 780

Ser Met Ala Arg Pro Val Ile Phe Pro Glu Ser Glu Ala Thr Asp Gln
785                 790                 795                 800

Asn Gln Lys Thr Lys Gly Pro Ile Leu Lys Ile Gln Gly Leu Trp His
            805                 810                 815

Pro Phe Ala Val Ala Ala Asp Gly Gln Leu Pro Val Pro Asn Asp Ile
                820                 825                 830

Leu Leu Gly Glu Ala Arg Arg Ser Gly Ser Ile His Pro Arg Ser
        835                 840                 845

Leu Leu Leu Thr Gly Pro Asn Met Gly Gly Lys Ser Thr Leu Leu Arg
            850                 855                 860

Ala Thr Cys Leu Ala Val Ile Phe Ala Gln Leu Gly Cys Tyr Val Pro
865                 870                 875                 880

Cys Glu Ser Cys Glu Ile Ser Leu Val Asp Thr Ile Phe Thr Arg Leu
                885                 890                 895

Gly Ala Ser Asp Arg Ile Met Thr Gly Glu Ser Thr Phe Leu Val Glu
            900                 905                 910

Cys Thr Glu Thr Ala Ser Val Leu Gln Asn Ala Thr Gln Asp Ser Leu
        915                 920                 925

Val Ile Leu Asp Glu Leu Gly Arg Gly Thr Ser Thr Phe Asp Gly Tyr
930                 935                 940

Ala Ile Ala Tyr Ser Val Phe Arg His Leu Val Glu Lys Val Gln Cys
945                 950                 955                 960

Arg Met Leu Phe Ala Thr His Tyr His Pro Leu Thr Lys Glu Phe Ala
            965                 970                 975

Ser His Pro Arg Val Thr Ser Lys His Met Ala Cys Ala Phe Lys Ser
                980                 985                 990

Arg Ser Asp Tyr Gln Pro Arg Gly Cys Asp Gln Asp Leu Val Phe Leu
        995                 1000                1005

Tyr Arg Leu Thr Glu Gly Ala Cys Pro Glu Ser Tyr Gly Leu Gln Val
        1010                1015                1020

Ala Leu Met Ala Gly Ile Pro Asn Gln Val Val Glu Thr Ala Ser Gly
1025                1030                1035                1040

Ala Ala Gln Ala Met Lys Arg Ser Ile Gly Glu Asn Phe Lys Ser Ser
```

-continued

```
                    1045                1050                1055
Glu Leu Arg Ser Glu Phe Ser Ser Leu His Glu Asp Trp Leu Lys Ser
            1060                1065                1070
Leu Val Gly Ile Ser Arg Val Ala His Asn Asn Ala Pro Ile Gly Glu
        1075                1080                1085
Asp Asp Tyr Asp Thr Leu Phe Cys Leu Trp His Glu Ile Lys Ser Ser
    1090                1095                1100
Tyr Cys Val Pro Lys
1105

<210> SEQ ID NO 32
<211> LENGTH: 24
<212> TYPE: DNA
<213> ORGANISM: Artificial Sequence
<220> FEATURE:
<223> OTHER INFORMATION: Forward primer for PCR amplification of
      ATHGENEA microsatellite.

<400> SEQUENCE: 32
accatgcata gcttaaactt cttg                                           24

<210> SEQ ID NO 33
<211> LENGTH: 22
<212> TYPE: DNA
<213> ORGANISM: Artificial Sequence
<220> FEATURE:
<223> OTHER INFORMATION: Reverse primer for PCR amplification of
      ATHGENEA microsatellite.

<400> SEQUENCE: 33
acataaccac aaatagnggt gc                                             22

<210> SEQ ID NO 34
<211> LENGTH: 18
<212> TYPE: DNA
<213> ORGANISM: Artificial Sequence
<220> FEATURE:
<223> OTHER INFORMATION: Forward primer DMCIN-A for PCR on genomic DNA
      of Arabidopsis thaliana ssp. Landsberg erecta "Ler".

<400> SEQUENCE: 34
gaagcgatat tgttcgtg                                                  18

<210> SEQ ID NO 35
<211> LENGTH: 18
<212> TYPE: DNA
<213> ORGANISM: Artificial Sequence
<220> FEATURE:
<223> OTHER INFORMATION: Reverse primer DMCIN-B for PCR on genomic DNA
      of Arabidopsis thaliana ssp. Landsberg erecta "Ler".

<400> SEQUENCE: 35
agattgcgag aacattcc                                                  18

<210> SEQ ID NO 36
<211> LENGTH: 31
<212> TYPE: DNA
<213> ORGANISM: Artificial Sequence
<220> FEATURE:
<223> OTHER INFORMATION: Forward primer DMCIN-1 for PCR on genomic DNA
      of Arabidopsis thaliana ssp. Landsberg erecta "Ler".

<400> SEQUENCE: 36
acgcgtcgac tcagctatga gattactcgt g                                   31
```

<210> SEQ ID NO 37
<211> LENGTH: 29
<212> TYPE: DNA
<213> ORGANISM: Artificial Sequence
<220> FEATURE:
<223> OTHER INFORMATION: Reverse primer DMCIN-2 for PCR on genomic DNA
      of Arabidopsis thaliana ssp. Landsberg erecta "Ler".

<400> SEQUENCE: 37
gctctagatt tctcgctcta agactctct                                    29

<210> SEQ ID NO 38
<211> LENGTH: 32
<212> TYPE: DNA
<213> ORGANISM: Artificial Sequence
<220> FEATURE:
<223> OTHER INFORMATION: Forward primer DMCIN-3 for PCR on genomic DNA
      of Arabidopsis thaliana ssp. Landsberg erecta "Ler".

<400> SEQUENCE: 38
gctctagagc ttctcttaag taagtgattg at                                32

<210> SEQ ID NO 39
<211> LENGTH: 48
<212> TYPE: DNA
<213> ORGANISM: Artificial Sequence
<220> FEATURE:
<223> OTHER INFORMATION: Reverse primer DMCIN-4 for PCR on genomic DNA
      of Arabidopsis thaliana ssp. Landsberg erecta "Ler".

<400> SEQUENCE: 39
tcccccgggc tcgagagatc tccatggttt cttcagctct atgaatcc               48

<210> SEQ ID NO 40
<211> LENGTH: 26
<212> TYPE: DNA
<213> ORGANISM: Artificial Sequence
<220> FEATURE:
<223> OTHER INFORMATION: Forward primer DMC1a for PCR on genomic DNA of
      Arabidopsis thaliana ssp. Landsberg erecta "Ler".

<400> SEQUENCE: 40
acgcgtcgac gaattcgcaa gtgggg                                       26

<210> SEQ ID NO 41
<211> LENGTH: 38
<212> TYPE: DNA
<213> ORGANISM: Artificial Sequence
<220> FEATURE:
<223> OTHER INFORMATION: Reverse primer DMC1b for PCR on genomic DNA of
      Arabidopsis thaliana ssp. Landsberg erecta "Ler".

<400> SEQUENCE: 41
tccatggaga tctcccgggt accgatttgc ttcgaggg                          38

<210> SEQ ID NO 42
<211> LENGTH: 20
<212> TYPE: DNA
<213> ORGANISM: Artificial Sequence
<220> FEATURE:
<223> OTHER INFORMATION: Forward primer for PCR amplification of ATEAT1
      SSLP marker in Arabidopsis thaliana subspecies.

<400> SEQUENCE: 42
gccactgcgt gaatgatatg                                              20

```
<210> SEQ ID NO 43
<211> LENGTH: 22
<212> TYPE: DNA
<213> ORGANISM: Artificial Sequence
<220> FEATURE:
<223> OTHER INFORMATION: Reverse primer for PCR amplification of ATEAT1
      SSLP marker in Arabidopsis thaliana subspecies.

<400> SEQUENCE: 43
cgaacagcca acattaattc cc                                                   22

<210> SEQ ID NO 44
<211> LENGTH: 18
<212> TYPE: DNA
<213> ORGANISM: Artificial Sequence
<220> FEATURE:
<223> OTHER INFORMATION: Forward primer for PCR amplification of NGA63
      SSLP marker in Arabidopsis thaliana subspecies.

<400> SEQUENCE: 44
aaccaaggca cagaagcg                                                        18

<210> SEQ ID NO 45
<211> LENGTH: 18
<212> TYPE: DNA
<213> ORGANISM: Artificial Sequence
<220> FEATURE:
<223> OTHER INFORMATION: Reverse primer for PCR amplification of NGA63
      SSLP marker in Arabidopsis thaliana subspecies.

<400> SEQUENCE: 45
acccaagtga tcgccacc                                                        18

<210> SEQ ID NO 46
<211> LENGTH: 21
<212> TYPE: DNA
<213> ORGANISM: Artificial Sequence
<220> FEATURE:
<223> OTHER INFORMATION: Forward primer for PCR amplification of NGA248
      SSLP marker in Arabidopsis thaliana subspecies.

<400> SEQUENCE: 46
taccgaacca aaacacaaag g                                                    21

<210> SEQ ID NO 47
<211> LENGTH: 22
<212> TYPE: DNA
<213> ORGANISM: Artificial Sequence
<220> FEATURE:
<223> OTHER INFORMATION: Reverse primer for PCR amplification of NGA248
      SSLP marker in Arabidopsis thaliana subspecies.

<400> SEQUENCE: 47
tctgtatctc ggtgaattct cc                                                   22

<210> SEQ ID NO 48
<211> LENGTH: 22
<212> TYPE: DNA
<213> ORGANISM: Artificial Sequence
<220> FEATURE:
<223> OTHER INFORMATION: Forward primer for PCR amplification of NGA128
      SSLP marker in Arabidopsis thaliana subspecies.

<400> SEQUENCE: 48
ggtctgttga tgtcgtaagt cg                                                   22

<210> SEQ ID NO 49
```

```
<211> LENGTH: 22
<212> TYPE: DNA
<213> ORGANISM: Artificial Sequence
<220> FEATURE:
<223> OTHER INFORMATION: Reverse primer for PCR amplification of NGA128
      SSLP marker in Arabidopsis thaliana subspecies.

<400> SEQUENCE: 49
atcttgaaac ctttagggag gg                                              22

<210> SEQ ID NO 50
<211> LENGTH: 22
<212> TYPE: DNA
<213> ORGANISM: Artificial Sequence
<220> FEATURE:
<223> OTHER INFORMATION: Forward primer for PCR amplification of NGA280
      SSLP marker in Arabidopsis thaliana subspecies.

<400> SEQUENCE: 50
ctgatctcac ggacaatagt gc                                              22

<210> SEQ ID NO 51
<211> LENGTH: 20
<212> TYPE: DNA
<213> ORGANISM: Artificial Sequence
<220> FEATURE:
<223> OTHER INFORMATION: Reverse primer for PCR amplification of NGA280
      SSLP marker in Arabidopsis thaliana subspecies.

<400> SEQUENCE: 51
ggctccataa aaagtgcacc                                                 20

<210> SEQ ID NO 52
<211> LENGTH: 21
<212> TYPE: DNA
<213> ORGANISM: Artificial Sequence
<220> FEATURE:
<223> OTHER INFORMATION: Forward primer for PCR amplification of NGA111
      SSLP marker in Arabidopsis thaliana subspecies.

<400> SEQUENCE: 52
ctccagttgg aagctaaagg g                                               21

<210> SEQ ID NO 53
<211> LENGTH: 21
<212> TYPE: DNA
<213> ORGANISM: Artificial Sequence
<220> FEATURE:
<223> OTHER INFORMATION: Reverse primer for PCR amplification of NGA111
      SSLP marker in Arabidopsis thaliana subspecies.

<400> SEQUENCE: 53 tgtttttag gacaaatggc g                                                21

<210> SEQ ID NO 54
<211> LENGTH: 20
<212> TYPE: DNA
<213> ORGANISM: Artificial Sequence
<220> FEATURE:
<223> OTHER INFORMATION: Forward primer for PCR amplification of NGA168
      SSLP marker in Arabidopsis thaliana subspecies.

<400> SEQUENCE: 54
ccttcacatc caaaacccac                                                 20

<210> SEQ ID NO 55
<211> LENGTH: 20
```

```
<212> TYPE: DNA
<213> ORGANISM: Artificial Sequence
<220> FEATURE:
<223> OTHER INFORMATION: Reverse primer for PCR amplification of NGA168
      SSLP marker in Arabidopsis thaliana subspecies.

<400> SEQUENCE: 55
gcacataccc acaaccagaa                                            20

<210> SEQ ID NO 56
<211> LENGTH: 20
<212> TYPE: DNA
<213> ORGANISM: Artificial Sequence
<220> FEATURE:
<223> OTHER INFORMATION: Forward primer for PCR amplification of NGA1126
      SSLP marker in Arabidopsis thaliana subspecies.

<400> SEQUENCE: 56
cgctacgctt ttcggtaaag                                            20

<210> SEQ ID NO 57
<211> LENGTH: 20
<212> TYPE: DNA
<213> ORGANISM: Artificial Sequence
<220> FEATURE:
<223> OTHER INFORMATION: Reverse primer for PCR amplification of NGA1126
      SSLP marker in Arabidopsis thaliana subspecies.

<400> SEQUENCE: 57
gcacagtcca agtcacaacc                                            20

<210> SEQ ID NO 58
<211> LENGTH: 20
<212> TYPE: DNA
<213> ORGANISM: Artificial Sequence
<220> FEATURE:
<223> OTHER INFORMATION: Forward primer for PCR amplification of NGA361
      SSLP marker in Arabidopsis thaliana subspecies.

<400> SEQUENCE: 58
aaagagatga gaatttggac                                            20

<210> SEQ ID NO 59
<211> LENGTH: 23
<212> TYPE: DNA
<213> ORGANISM: Artificial Sequence
<220> FEATURE:
<223> OTHER INFORMATION: Reverse primer for PCR amplification of NGA361
      SSLP marker in Arabidopsis thaliana subspecies.

<400> SEQUENCE: 59
acatatcaat atattaaagt agc                                        23

<210> SEQ ID NO 60
<211> LENGTH: 18
<212> TYPE: DNA
<213> ORGANISM: Artificial Sequence
<220> FEATURE:
<223> OTHER INFORMATION: Forward primer for PCR amplification of NGA168
      SSLP marker in Arabidopsis thaliana subspecies.

<400> SEQUENCE: 60
tcgtctactg cactgccg                                              18

<210> SEQ ID NO 61
<211> LENGTH: 22
<212> TYPE: DNA
```

```
<213> ORGANISM: Artificial Sequence
<220> FEATURE:
<223> OTHER INFORMATION: Reverse primer for PCR amplification of NGA168
      SSLP marker in Arabidopsis thaliana subspecies.

<400> SEQUENCE: 61
gaggacatgt ataggagcct cg                                              22

<210> SEQ ID NO 62
<211> LENGTH: 20
<212> TYPE: DNA
<213> ORGANISM: Artificial Sequence
<220> FEATURE:
<223> OTHER INFORMATION: Forward primer for PCR amplification of AthBIO2
      SSLP marker in Arabidopsis thaliana subspecies.

<400> SEQUENCE: 62
tgacctcctc ttccatggag                                                 20

<210> SEQ ID NO 63
<211> LENGTH: 22
<212> TYPE: DNA
<213> ORGANISM: Artificial Sequence
<220> FEATURE:
<223> OTHER INFORMATION: Reverse primer for PCR amplification of AthBIO2
      SSLP marker in Arabidopsis thaliana subspecies.

<400> SEQUENCE: 63
ttaacagaaa cccaaagctt tc                                              22

<210> SEQ ID NO 64
<211> LENGTH: 21
<212> TYPE: DNA
<213> ORGANISM: Artificial Sequence
<220> FEATURE:
<223> OTHER INFORMATION: Forward primer for PCR amplification of
      AthUBIQUE SSLP marker in Arabidopsis thaliana subspecies.

<400> SEQUENCE: 64
aggcaaatgt ccatttcatt g                                               21

<210> SEQ ID NO 65
<211> LENGTH: 20
<212> TYPE: DNA
<213> ORGANISM: Artificial Sequence
<220> FEATURE:
<223> OTHER INFORMATION: Reverse primer for PCR amplification of
      AthUBIQUE SSLP marker in Arabidopsis thaliana subspecies.

<400> SEQUENCE: 65
acgacatggc agatttctcc                                                 20

<210> SEQ ID NO 66
<211> LENGTH: 21
<212> TYPE: DNA
<213> ORGANISM: Artificial Sequence
<220> FEATURE:
<223> OTHER INFORMATION: Forward primer for PCR amplification of NGA172
      SSLP marker in Arabidopsis thaliana subspecies.

<400> SEQUENCE: 66
agctgcttcc ttatagcgtc c                                               21

<210> SEQ ID NO 67
<211> LENGTH: 19
<212> TYPE: DNA
<213> ORGANISM: Artificial Sequence
```

```
<220> FEATURE:
<223> OTHER INFORMATION: Reverse primer for PCR amplification of NGA172
      SSLP marker in Arabidopsis thaliana subspecies.

<400> SEQUENCE: 67
catccgaatg ccattgttc                                                    19

<210> SEQ ID NO 68
<211> LENGTH: 21
<212> TYPE: DNA
<213> ORGANISM: Artificial Sequence
<220> FEATURE:
<223> OTHER INFORMATION: Forward primer for PCR amplification of NGA126
      SSLP marker in Arabidopsis thaliana subspecies.

<400> SEQUENCE: 68
gaaaaaacgc tactttcgtg g                                                 21

<210> SEQ ID NO 69
<211> LENGTH: 22
<212> TYPE: DNA
<213> ORGANISM: Artificial Sequence
<220> FEATURE:
<223> OTHER INFORMATION: Reverse primer for PCR amplification of NGA126
      SSLP marker in Arabidopsis thaliana subspecies.

<400> SEQUENCE: 69
caagagcaat atcaagagca gc                                                22

<210> SEQ ID NO 70
<211> LENGTH: 20
<212> TYPE: DNA
<213> ORGANISM: Artificial Sequence
<220> FEATURE:
<223> OTHER INFORMATION: Forward primer for PCR amplification of NGA162
      SSLP marker in Arabidopsis thaliana subspecies.

<400> SEQUENCE: 70
catgcaattt gcatctgagg                                                   20

<210> SEQ ID NO 71
<211> LENGTH: 22
<212> TYPE: DNA
<213> ORGANISM: Artificial Sequence
<220> FEATURE:
<223> OTHER INFORMATION: Reverse primer for PCR amplification of NGA162
      SSLP marker in Arabidopsis thaliana subspecies.

<400> SEQUENCE: 71
ctctgtcact cttttcctct gg                                                22

<210> SEQ ID NO 72
<211> LENGTH: 21
<212> TYPE: DNA
<213> ORGANISM: Artificial Sequence
<220> FEATURE:
<223> OTHER INFORMATION: Forward primer for PCR amplification of NGA6
      SSLP marker in Arabidopsis thaliana subspecies.

<400> SEQUENCE: 72
tggatttctt cctctcttca c                                                 21

<210> SEQ ID NO 73
<211> LENGTH: 21
<212> TYPE: DNA
<213> ORGANISM: Artificial Sequence
<220> FEATURE:
```

```
<223> OTHER INFORMATION: Reverse primer for PCR amplification of NGA6
      SSLP marker in Arabidopsis thaliana subspecies.

<400> SEQUENCE: 73
atggagaagc ttacactgat c                                              21

<210> SEQ ID NO 74
<211> LENGTH: 20
<212> TYPE: DNA
<213> ORGANISM: Artificial Sequence
<220> FEATURE:
<223> OTHER INFORMATION: Forward primer for PCR amplification of NGA12
      SSLP marker in Arabidopsis thaliana subspecies.

<400> SEQUENCE: 74
aatgttgtcc tcccctcctc                                                20

<210> SEQ ID NO 75
<211> LENGTH: 22
<212> TYPE: DNA
<213> ORGANISM: Artificial Sequence
<220> FEATURE:
<223> OTHER INFORMATION: Reverse primer for PCR amplification of NGA12
      SSLP marker in Arabidopsis thaliana subspecies.

<400> SEQUENCE: 75
tgatgctctc tgaaacaaga gc                                             22

<210> SEQ ID NO 76
<211> LENGTH: 21
<212> TYPE: DNA
<213> ORGANISM: Artificial Sequence
<220> FEATURE:
<223> OTHER INFORMATION: Forward primer for PCR amplification of NGA8
      SSLP marker in Arabidopsis thaliana subspecies.

<400> SEQUENCE: 76
gagggcaaat ctttatttcg g                                              21

<210> SEQ ID NO 77
<211> LENGTH: 22
<212> TYPE: DNA
<213> ORGANISM: Artificial Sequence
<220> FEATURE:
<223> OTHER INFORMATION: Reverse primer for PCR amplification of NGA8
      SSLP marker in Arabidopsis thaliana subspecies.

<400> SEQUENCE: 77
tggctttcgt ttataaacat cc                                             22

<210> SEQ ID NO 78
<211> LENGTH: 21
<212> TYPE: DNA
<213> ORGANISM: Artificial Sequence
<220> FEATURE:
<223> OTHER INFORMATION: Forward primer for PCR amplification of NGA1107
      SSLP marker in Arabidopsis thaliana subspecies.

<400> SEQUENCE: 78
gcgaaaaaac aaaaaaatcc a                                              21

<210> SEQ ID NO 79
<211> LENGTH: 21
<212> TYPE: DNA
<213> ORGANISM: Artificial Sequence
<220> FEATURE:
<223> OTHER INFORMATION: Reverse primer for PCR amplification of NGA1107
```

SSLP marker in Arabidopsis thaliana subspecies.

<400> SEQUENCE: 79
cgacgaatcg acagaattag g                                           21

<210> SEQ ID NO 80
<211> LENGTH: 21
<212> TYPE: DNA
<213> ORGANISM: Artificial Sequence
<220> FEATURE:
<223> OTHER INFORMATION: Forward primer for PCR amplification of NGA225
      SSLP marker in Arabidopsis thaliana subspecies.

<400> SEQUENCE: 80
gaaatccaaa tcccagagag g                                           21

<210> SEQ ID NO 81
<211> LENGTH: 22
<212> TYPE: DNA
<213> ORGANISM: Artificial Sequence
<220> FEATURE:
<223> OTHER INFORMATION: Reverse primer for PCR amplification of NGA225
      SSLP marker in Arabidopsis thaliana subspecies.

<400> SEQUENCE: 81
tctccccact agttttgtgt cc                                          22

<210> SEQ ID NO 82
<211> LENGTH: 19
<212> TYPE: DNA
<213> ORGANISM: Artificial Sequence
<220> FEATURE:
<223> OTHER INFORMATION: Forward primer for PCR amplification of NGA249
      SSLP marker in Arabidopsis thaliana subspecies.

<400> SEQUENCE: 82
taccgtcaat ttcatcgcc                                              19

<210> SEQ ID NO 83
<211> LENGTH: 22
<212> TYPE: DNA
<213> ORGANISM: Artificial Sequence
<220> FEATURE:
<223> OTHER INFORMATION: Reverse primer for PCR amplification of NGA249
      SSLP marker in Arabidopsis thaliana subspecies.

<400> SEQUENCE: 83
ggatccctaa ctgtaaaatc cc                                          22

<210> SEQ ID NO 84
<211> LENGTH: 22
<212> TYPE: DNA
<213> ORGANISM: Artificial Sequence
<220> FEATURE:
<223> OTHER INFORMATION: Forward primer for PCR amplification of CA72
      SSLP marker in Arabidopsis thaliana subspecies.

<400> SEQUENCE: 84
aatcccagta accaaacaca ca                                          22

<210> SEQ ID NO 85
<211> LENGTH: 20
<212> TYPE: DNA
<213> ORGANISM: Artificial Sequence
<220> FEATURE:
<223> OTHER INFORMATION: Reverse primer for PCR amplification of CA72
      SSLP marker in Arabidopsis thaliana subspecies.

<400> SEQUENCE: 85
cccagtctaa ccacgaccac                                               20

<210> SEQ ID NO 86
<211> LENGTH: 20
<212> TYPE: DNA
<213> ORGANISM: Artificial Sequence
<220> FEATURE:
<223> OTHER INFORMATION: Forward primer for PCR amplification of NGA151
      SSLP marker in Arabidopsis thaliana subspecies.

<400> SEQUENCE: 86
gttttgggaa gttttgctgg                                               20

<210> SEQ ID NO 87
<211> LENGTH: 24
<212> TYPE: DNA
<213> ORGANISM: Artificial Sequence
<220> FEATURE:
<223> OTHER INFORMATION: Reverse primer for PCR amplification of NGA151
      SSLP marker in Arabidopsis thaliana subspecies.

<400> SEQUENCE: 87
cagtctaaaa gcgagagtat gatg                                          24

<210> SEQ ID NO 88
<211> LENGTH: 22
<212> TYPE: DNA
<213> ORGANISM: Artificial Sequence
<220> FEATURE:
<223> OTHER INFORMATION: Forward primer for PCR amplification of NGA106
      SSLP marker in Arabidopsis thaliana subspecies.

<400> SEQUENCE: 88
gttatggagt ttctagggca cg                                            22

<210> SEQ ID NO 89
<211> LENGTH: 20
<212> TYPE: DNA
<213> ORGANISM: Artificial Sequence
<220> FEATURE:
<223> OTHER INFORMATION: Reverse primer for PCR amplification of NGA106
      SSLP marker in Arabidopsis thaliana subspecies.

<400> SEQUENCE: 89
tgccccattt tgttcttctc                                               20

<210> SEQ ID NO 90
<211> LENGTH: 20
<212> TYPE: DNA
<213> ORGANISM: Artificial Sequence
<220> FEATURE:
<223> OTHER INFORMATION: Forward primer for PCR amplification of NGA139
      SSLP marker in Arabidopsis thaliana subspecies.

<400> SEQUENCE: 90
agagctacca gatccgatgg                                               20

<210> SEQ ID NO 91
<211> LENGTH: 21
<212> TYPE: DNA
<213> ORGANISM: Artificial Sequence
<220> FEATURE:
<223> OTHER INFORMATION: Reverse primer for PCR amplification of NGA139
      SSLP marker in Arabidopsis thaliana subspecies.

```
<400> SEQUENCE: 91
ggtttcgttt cactatccag g                                              21

<210> SEQ ID NO 92
<211> LENGTH: 22
<212> TYPE: DNA
<213> ORGANISM: Artificial Sequence
<220> FEATURE:
<223> OTHER INFORMATION: Forward primer for PCR amplification of NGA76
      SSLP marker in Arabidopsis thaliana subspecies.

<400> SEQUENCE: 92
ggagaaaatg tcactctcca cc                                             22

<210> SEQ ID NO 93
<211> LENGTH: 20
<212> TYPE: DNA
<213> ORGANISM: Artificial Sequence
<220> FEATURE:
<223> OTHER INFORMATION: Reverse primer for PCR amplification of NGA76
      SSLP marker in Arabidopsis thaliana subspecies.

<400> SEQUENCE: 93
aggcatggga gacatttacg                                                20

<210> SEQ ID NO 94
<211> LENGTH: 20
<212> TYPE: DNA
<213> ORGANISM: Artificial Sequence
<220> FEATURE:
<223> OTHER INFORMATION: Forward primer for PCR amplification of
      ATHSO191 SSLP marker in Arabidopsis thaliana subspecies.

<400> SEQUENCE: 94
ctccaccaat catgcaaatg                                                20

<210> SEQ ID NO 95
<211> LENGTH: 21
<212> TYPE: DNA
<213> ORGANISM: Artificial Sequence
<220> FEATURE:
<223> OTHER INFORMATION: Reverse primer for PCR amplification of
      ATHSO191 SSLP marker in Arabidopsis thaliana subspecies.

<400> SEQUENCE: 95
tgatgttgat ggagatggtc a                                              21

<210> SEQ ID NO 96
<211> LENGTH: 22
<212> TYPE: DNA
<213> ORGANISM: Artificial Sequence
<220> FEATURE:
<223> OTHER INFORMATION: Forward primer for PCR amplification of NGA129
      SSLP marker in Arabidopsis thaliana subspecies.

<400> SEQUENCE: 96
tcaggaggaa ctaaagtgag gg                                             22

<210> SEQ ID NO 97
<211> LENGTH: 22
<212> TYPE: DNA
<213> ORGANISM: Artificial Sequence
<220> FEATURE:
<223> OTHER INFORMATION: Reverse primer for PCR amplification of NGA129
      SSLP marker in Arabidopsis thaliana subspecies.

<400> SEQUENCE: 97
```

```
cacactgaag atggtcttga gg                                               22
```

<210> SEQ ID NO 98
<211> LENGTH: 8062
<212> TYPE: DNA
<213> ORGANISM: Arabidopsis thaliana ecotype Columbia
<220> FEATURE:
<223> OTHER INFORMATION: Genomic DNA sequence of AtMSH6

<400> SEQUENCE: 98

```
tttttttggtt gctaacaata aaggtatacg gttttatgtc atcaatataa ctatatataa       60
aagaaatgaa agatatatat tgttttttca tttatcaaac aaaacaacaa gacttttttt      120
ttactttttta cattggtcaa caaaatacaa gataaacgac atcgtttaat catttcccaa      180
ttttaccccct aagtttaaca cctagaacct tctccatctt cgcaagcaca gcctgattag      240
gaacagcttt accattctca tattcctgaa ctacctgagt cctctcattg atctgtttcg      300
ccaaatccgc ttgtgacatc ttcttctcca atctcgcttt ctgtatcatc aacctcacct      360
ctgcttttcac acgatccatc gccgcaggct ctgtttcttc ttccagcttc ttcgtgttaa      420
tcaccggaac cgccgtagat ttcccctttt tgttcgaacc ggcatcgaat ttcttaaccg      480
tttgaaccgc gacaccgttt ctcagagctg cgttaaccgc tttcggatcg cgtaggtctt      540
ggctcttttg ttttgatttg tggagaacta ctggttccca gtcttgtgtt actgctcctg      600
ggtatctgct cggcatcgtc gatgaattga gagaaaggaa caacgcgaaa attttattaa      660
tctgagtttt gaaattgaga acgatgaag atgaagaatg ttgttgagag gattgtgata      720
tttatatata cgaagattgg tttctggaga attcgatcat cttttttctcc attttcgtct      780
ctggaacgtt cttagagatg attgacgacg tgtcattatc tgatttgcag ttaaccaatg      840
cttttttgggt tggattcgtg gtacaccata ttatccgatt tggctcaatg gttttatata      900
aatttggttt tcggttcggt tatgagttat cattaaaatt aagctaacca aaaattttcg      960
taaaatttat ttcggtttca attcggatcc cttacttcca gaaccgaatt attcgaaacc     1020
ggggttagcc gaaccgaata ccaatgcctg attgactcgt tggctagaaa gatccaacgg     1080
tatacaataa tagaacataa atcggacggt catcaaagcc tcaaagagtg aacagtcaac     1140
aaaaaaagtt gagccctgag gagtatcgtt tccgccattt ctacgacgca aggcgaaaat     1200
ttttggcgcc aatctttccc ccctttcgaa ttctctcagc tcaaaacatc gtttctctct     1260
cactctctct cacaattcca aaaatgcag cgccagagat cgattttgtc tttcttccaa      1320
aaacccacgg cggcgactac gaagggtttg gtttccggcg atgctgctag cggcgggggc     1380
ggcagcggag accacgattt aatgtgaagg aaggggatgc taaaggcgac gcttctgtac     1440
gttttgctgt ttcgaaatct gtcgatgagg ttagaggaac ggatactcca ccggagaagg     1500
ttccgcgtcg tgtcctgccg tctggattta agccggctga atccgccggt gatgcttcgt     1560
ccctgttctc caatattatg cataagtttg taaaagtcga tgatcgagat tgttctggag     1620
agaggtacta atcttcgatt ctcttaattt tgttatcttt agctggaaga agaagattcg     1680
tgtaatttgt tgtattcgtt ggagagattc tgattactgc attggatcgt tgtttacaaa     1740
ttttcaggag ccgagaagat gttgttccgc tgaatgattc atctctatgt atgaaggcta     1800
atgatgttat tcctcaattt cgttccaata atggtaaaac tcaagaaaga aaccatgctt     1860
ttagtttcag tgggagagct gaacttagat cagtagaaga tataggagta gatggcgatg     1920
ttcctggtcc agaaacacca gggatgcgtc cacgtgcttc tcgcttgaag cgagttctgg     1980
```

```
aggatgaaat gacttttaag gaggataagg ttcctgtatt ggactctaac aaaaggctga    2040
aaatgctcca ggatccggtt tgtggagaga agaaagaagt aaacgaagga accaaatttg    2100
aatggcttga gtcttctcga atcagggatg ccaatagaag acgtcctgat gatcccsttt    2160
acgatagaaa gaccttacac ataccacctg atgttttcaa gaaaatgtct gcatcacaaa    2220
agcaatattg gagtgttaag agtgaatata tggacattgt gcttttcttt aaagtggtta    2280
gtaactatta atctagtgtt caatccattt cctcaatgtg atttgttcac ttacatctgt    2340
ttacgttatg ctcttctcag gggaaatttt atgagctgta tgagctagat gcggaattag    2400
gtcacaagga gcttgactgg aagatgacca tgagtggtgt gggaaaatgc agacaggtaa    2460
attagttgaa acaactggcc tgcttgaatt attgtgtcta taaattttga caccacctt    2520 tgtttcaggt tggtatctct gaaagtggga tagatgaggc agtgcaaaag ctattagctc    2580
gtgggtaagg gaaccatcat actttatgga attcgtttac tgctacttcg gctaggattt    2640
aagaaatgga aatcacttca agcatcatta gttaggatcc tgagaactca ggatgttttc    2700
ttattcgtta tataataagt cttttcatca aggagtaaca aacaaaactt gcacaatatt    2760
tgtgtgctca ctggcaaggc atatataccc agctaaccct tgctagttca ctgtagtaac    2820
agttacggat aatatatgtt tacttgtatg tggtaccctc attttgtctc tcatggaggc    2880
tttcaagcct tgtgttgaaa ctggatagtt acatatgctt ccaacagaaa ctagcatgca    2940
gattcatatg ctttcctatt ctactaatta tgtattgaca cactcgttgt ttcttttgaa    3000
agatataaag ttggacgaat cgagcagcta gaaacatctg accaagcaaa gccagaggt    3060 gctaatactg taagttttct tggataggtc aaggagagtg ttgcagactg ttttttgatca    3120 tttcttttcc tgtacattac tttcatgctg taattaactc aatggctatt ctggtctgat    3180
tatcagataa ttccaaggaa gctagttcag gtattaactc catcaacagc aagcgaggga    3240
aacatcgggc ctgatgccgt ccatcttctt gctataaaag aggtttgtta tttacttatt    3300
tatcttatca tgttcagttc atccaagtcc tgaaaaatta cactcttctt taccaatctt    3360
ccatcaagct gtgtaaagga tttggaatta gaaaatcatt atttgatgct ttgtttttata    3420 tgcaagaggt tcccttgaaa agatctgttt aagattcttt gcacttgaaa aattcaatct    3480
ttttaagtga atcccctact ttcttacaat gatcatagtc tgcaattgca tgtcaagtaa    3540
tatcattcct tgttactgca tcccctctt tcttaatgac cattgtctat gttgtgtttg    3600
tctcgtgtgc tggagaaaat gatagctgat ccaagctgta cattatcatg attaagtagc    3660
tgctcaggaa ttgcctttgg ttacattgcc taatggtttg atgtcaattt ttcttctgaa    3720
tctttatttt agatcaaaat ggagctacaa aagtgttcaa ctgtgtatgg atttgctttt    3780
gttgactgtg ctgccttgag gttttgggtt gggtccatca gcgatgatgc atcatgtgct    3840
gctcttggag cgttattgat gcaggtaagc aagtgtattc tgtatcttat gtgtaccatg    3900
tgacttcctg tgcatatatt tgggttgcag gaactaattc tgaatcacca tttggtatgt    3960
tttttccagg tttctccaaa ggaagtgtta tatgacagta aagtaaaact gcttgtatcg    4020
ccagttgttt tgttaaacag aatttaaggt aaatgacact ggttaattta aagtgcatac    4080
atgttgaaat attgcaggge tatcaagaga agcacaaaag gctctaagga aatatacgtt    4140
gacaggtacc atttcagtag gcaagctaac tgacaattta accgctcacc gaatgatagg    4200
tctcttaaac attgctaatg tagatgatgt ttatgtttca atctaatagg gtctacggcg    4260
gtacagttgg ctccagtacc acaagtaatg ggggatacag atgctgctgg agttagaaat    4320
ataatagaat ctaacggata ctttaaaggt tcttctgaat catggaactg tgctgttgat    4380
```

-continued

```
ggtctaaatg aatgtgatgt tgcccttagt gctcttggag agctaattaa tcatctgtct    4440
aggctaaagg tgtgttggct tgtttagttt ttgcttttca caaattaagc aaaggaactt    4500
ttcataactt acagtttcta tctacttgca gctagaagat gtacttaagc atggggatat    4560
ttttccatac caagtttaca ggggttgtct cagaattgat ggccagacga tggtaaatct    4620
tgagatattt aacaatagct gtgatggtgg tccttcaggc aagtgcatat ttctttttg     4680 ataacttcaa ctagagggca gacatagaag gaaaaattct aatacttcgt acggatctcc    4740
agtaagtaat agccgatttt tgtttaccta tgtagggacc ttgtacaaat atcttgataa    4800
ctgtgttagt ccaactggta agcgactctt aaggaattgg atctgccatc cactcaaaga    4860
tgtagaaagc atcaataaac ggcttgatgt agttgaagaa ttcacggcaa actcagaaag    4920
tatgcaaatc actggccagt atctccacaa acttccagac ttagaaagac tgctcggacg    4980
catcaagtct agcgttcgat catcagcctc tgtgttgcct gctcttctgg ggaaaaaagt    5040
gctgaaacaa cgagtaagta tcaatcacaa gttttctgag taatgccttc catgagtagt    5100
ataggactaa aacattacgg gtctagctaa agactgttct ccttcttttg caatgtctgg    5160
ttattcatta catttctctt aacttattgc attgcaggtt aaagcatttg ggcaaattgt    5220
gaaagggttc agaagtggaa ttgatctgtt gttggctcta cagaaggaat caaatatgat    5280
gagtttgctt tataaactct gtaaacttcc tatattagta ggaaaaagcg ggctagagtt    5340
atttctttct caattcgaag cagccataga tagcgacttt ccaaattatc aggtgcccat    5400
ctatctttca tactttacaa caaaatgtct gtcactactc aaagcaatgc atatggctta    5460
gatctcaact cacaccccga ggatcctaaa gggatttgct ttttattcct aatgtttttg    5520
gatggtttga tttatttcta acttgaactt attaatcttg taccagaacc aagatgtgac    5580
agatgaaaac gctgaaactc tcacaatact tatcgaactt tttatcgaaa gagcaactca    5640
atggtctgag gtcattcaca ccataagctg cctagatgtc ctgagatctt ttgcaatcgc    5700
agcaagtctc tctgctggaa gcatggccag gcctgttatt tttcccgaat cagaagctac    5760
agatcagaat cagaaaacaa aagggccaat acttaaaatc caaggactat ggcatccatt    5820
tgcagttgca gccgatggtc aattgcctgt tccgaatgat atactccttg gcgaggctag    5880
aagaagcagt ggcagcattc atcctcggtc attgttactg acgggaccaa acatgggcgg    5940
aaaatcaact cttcttcgtg caacatgtct ggccgttatc tttgcccaag tttgtatact    6000
cgttagataa ttactctatt ctttgcaatc agttcttcaa catgaataat aaattctgtt    6060
ttctgtctgc agcttggctg ctacgtgccg tgtgagtctt gcgaaatctc cctcgtggat    6120
actatcttca caaggcttgg cgcatctgat agaatcatga caggagagag taagttttgt    6180
tctcaaaata ccaattcctc gaactattta ctcagatttt gtctgattgg acaaggtggt    6240
tttgcttttt tttaggtacc tttttggtag aatgcactga cacagcgtca gttcttcaga    6300
atgcaactca ggattcacta gtaatccttg acgaactggg cagaggaact agtactttcg    6360
atggatacgc cattgcatac tcggtaacct gctcttctcc ttcaacttat acttgttgat    6420
caacaaaaac atgcaattca ttttgctgaa acttattgat ttatatcagg ttttttcgtca   6480 cctggtagag aaagttcaat gtcggatgct ctttgcaaca cattaccacc ctctcaccaa    6540
ggaattcgcg tctcacccac gtgtcacctc gaaacacatg gcttgcgcat tcaaatcaag    6600
atctgattat caaccacgtg gttgtgatca agacctagtt ttcttgtacc gtttaaccga    6660
gggagcttgt cctgagagct acggacttca agtggcactc atggctggaa taccaaacca    6720
```

-continued

```
agtggttgaa acagcatcag gtgctgctca agccatgaag agatcaattg gggaaaactt    6780
caagtcaagt gagctaagat ctgagttctc aagtctgcat gaagactggc tcaagtcatt    6840
ggtgggtatt tctcgagtcg cccacaacaa tgcccccatt ggcgaagatg actacgacac    6900
tttgttttgc ttatggcatg agatcaaatc ctcttactgt gttcccaaat aaatggctat    6960
gacataacac tatctgaagc tcgttaagtc ttttgcttct ctgatgttta ttcctcttaa    7020
aaaatgctta tatatcaaaa aattgtttcc tcgattataa caagattata tatgtatctg    7080
tcggtttagc tatggtatat aatatatgta tgttcatgag attggtcaag agaaatactc    7140
acaaacagta tattaagaag gaaatatgtt tatgcattaa tttaagtttc aagataaact    7200
gcaaataacc tcgactaaag ttgcaaagac caaacacaaa ttacaaaact tataagactt    7260
aagttctgaa ttccctaaaa ccaaaaaaaa aaacagaaca tattttgttg catctacaaa    7320
caacacaaac ctacatagtt tataacttac tcatcactga gattaacatc agaatcattc    7380
tccatttctt catcttcact ctcatcatca tcaccaccac catgatgatt ctcctcctct    7440
tcacgtaacc tagcaatctc actctgagct ctatcaacaa tctgcttctt ctgcaactcc    7500
aaatctctct gaaaatcagc tctcatcttc tccaactcct tcatttgctc tttcttactc    7560
ttctccatct tctcataaac cttcccaaac ctctcaacag aatccgccaa catcttatac    7620
gaagcagcgt cattaacctt cttcctctcg tactcaacct catcatcctc atcctcctcc    7680
tcttcagaat caccaggact atccatcatc tcatcaaacc cattagactt atctaaataa    7740
accttagtgt tcataaacac aaactcacct gaatcaacac cacaagctaa acctaaatcc    7800
gacttgggcg aaaacaaaag caacatatcc aacttattga aaaacgacca tttacttgaa    7860
cctaaacctg atttctcaac cttaatcttc tcttttctat acttcctctt caagtcatca    7920
atcattctcc tacattgcgt ctcagatttc tccatcctta gctcctcact cactttctca    7980
gctacttcat tccaatcctc gttcctcaaa ctccttctac ccaattgcaa aaacctatct    8040
ccccaaactt caagcaacac aa                                              8062
```

<210> SEQ ID NO 99
<211> LENGTH: 1047
<212> TYPE: PRT
<213> ORGANISM: Saccharomyces cerevisiae

<400> SEQUENCE: 99

Met Val Ile Gly Asn Glu Pro Lys Leu Val Leu Arg Ala Lys Ser
1               5                   10                  15

Ser Ala Asn Arg Phe Ile Leu Leu Asn Leu Leu Thr Ile Met Ala Gly
            20                  25                  30

Gln Pro Thr Ile Ser Arg Phe Lys Lys Ala Val Lys Ser Glu Leu
        35                  40                  45

Thr His Lys Gln Glu Gln Glu Val Ala Val Gly Asn Gly Ala Gly Ser
    50                  55                  60

Glu Ser Ile Cys Leu Asp Thr Asp Glu Glu Asp Asn Leu Ser Ser Val
65                  70                  75                  80

Ala Ser Thr Thr Val Thr Asn Asp Ser Phe Pro Leu Lys Gly Ser Val
                85                  90                  95

Ser Ser Lys Asn Ser Lys Asn Ser Glu Lys Thr Ser Gly Thr Ser Thr
            100                 105                 110

Thr Phe Asn Asp Ile Asp Phe Ala Lys Lys Leu Asp Arg Ile Met Lys
        115                 120                 125

Arg Arg Ser Asp Glu Asn Val Glu Ala Glu Asp Asp Glu Glu Glu Gly

-continued

```
          130                 135                 140
Glu Glu Asp Phe Val Lys Lys Lys Ala Arg Lys Ser Pro Thr Ala Lys
145                 150                 155                 160

Leu Thr Pro Leu Asp Lys Gln Val Lys Asp Leu Lys Met His His Arg
                165                 170                 175

Asp Lys Val Leu Val Ile Arg Val Gly Tyr Lys Tyr Lys Cys Phe Ala
            180                 185                 190

Glu Asp Ala Val Thr Val Ser Arg Ile Leu His Ile Lys Leu Val Pro
        195                 200                 205

Gly Lys Leu Thr Ile Asp Glu Ser Asn Pro Gln Asp Cys Asn His Arg
    210                 215                 220

Gln Phe Ala Tyr Cys Ser Phe Pro Asp Val Arg Leu Asn Val His Leu
225                 230                 235                 240

Glu Arg Leu Val His His Asn Leu Lys Val Ala Val Val Glu Gln Ala
                245                 250                 255

Glu Thr Ser Ala Ile Lys Lys His Asp Pro Gly Ala Ser Lys Ser Ser
            260                 265                 270

Val Phe Glu Arg Lys Ile Ser Asn Val Phe Thr Lys Ala Thr Phe Gly
        275                 280                 285

Val Asn Ser Thr Phe Val Leu Arg Gly Lys Arg Ile Leu Gly Asp Thr
    290                 295                 300

Asn Ser Ile Trp Ala Leu Ser Arg Asp Val His Gln Gly Lys Val Ala
305                 310                 315                 320

Lys Tyr Ser Leu Ile Ser Val Asn Leu Asn Asn Gly Glu Val Val Tyr
                325                 330                 335

Asp Glu Phe Glu Glu Pro Asn Leu Ala Asp Glu Lys Leu Gln Ile Arg
            340                 345                 350

Ile Lys Tyr Leu Gln Pro Ile Glu Val Leu Val Asn Thr Asp Asp Leu
        355                 360                 365

Pro Leu His Val Ala Lys Phe Phe Lys Asp Ile Ser Cys Pro Leu Ile
    370                 375                 380

His Lys Gln Glu Tyr Asp Leu Glu Asp His Val Val Gln Ala Ile Lys
385                 390                 395                 400

Val Met Asn Glu Lys Ile Gln Leu Ser Pro Ser Leu Ile Arg Leu Val
                405                 410                 415

Ser Lys Leu Tyr Ser His Met Val Glu Tyr Asn Asn Glu Gln Val Met
            420                 425                 430

Leu Ile Pro Ser Ile Tyr Ser Pro Phe Ala Ser Lys Ile His Met Leu
        435                 440                 445

Leu Asp Pro Asn Ser Leu Gln Ser Leu Asp Ile Phe Thr His Asp Gly
    450                 455                 460

Gly Lys Gly Ser Leu Phe Trp Leu Leu Asp His Thr Arg Thr Ser Phe
465                 470                 475                 480

Gly Leu Arg Met Leu Arg Glu Trp Ile Leu Lys Pro Leu Val Asp Val
                485                 490                 495

His Gln Ile Glu Glu Arg Leu Asp Ala Ile Glu Cys Ile Thr Ser Glu
            500                 505                 510

Ile Asn Asn Ser Ile Phe Phe Glu Ser Leu Asn Gln Met Leu Asn His
        515                 520                 525

Thr Pro Asp Leu Leu Arg Thr Leu Asn Arg Ile Met Tyr Gly Thr Thr
    530                 535                 540

Ser Arg Lys Glu Val Tyr Phe Tyr Leu Lys Gln Ile Thr Ser Phe Val
545                 550                 555                 560
```

-continued

```
Asp His Phe Lys Met His Gln Ser Tyr Leu Ser Glu His Phe Lys Ser
            565                 570                 575

Ser Asp Gly Arg Ile Gly Lys Gln Ser Pro Leu Leu Phe Arg Leu Phe
            580                 585                 590

Ser Glu Leu Asn Glu Leu Leu Ser Thr Thr Gln Leu Pro His Phe Leu
            595                 600                 605

Thr Met Ile Asn Val Ser Ala Val Met Glu Lys Asn Ser Asp Lys Gln
            610                 615                 620

Val Met Asp Phe Phe Asn Leu Asn Asn Tyr Asp Cys Ser Glu Gly Ile
625                 630                 635                 640

Ile Lys Ile Gln Arg Glu Ser Glu Ser Val Arg Ser Gln Leu Lys Glu
            645                 650                 655

Glu Leu Ala Glu Ile Arg Lys Tyr Leu Lys Arg Pro Tyr Leu Asn Phe
            660                 665                 670

Arg Asp Glu Val Asp Tyr Leu Ile Glu Val Lys Asn Ser Gln Ile Lys
            675                 680                 685

Asp Leu Pro Asp Asp Trp Ile Lys Val Asn Asn Thr Lys Met Val Ser
            690                 695                 700

Arg Phe Thr Thr Pro Arg Thr Gln Lys Leu Thr Gln Lys Leu Glu Tyr
705                 710                 715                 720

Tyr Lys Asp Leu Leu Ile Arg Glu Ser Glu Leu Gln Tyr Lys Glu Phe
            725                 730                 735

Leu Asn Lys Ile Thr Ala Glu Tyr Thr Glu Leu Arg Lys Ile Thr Leu
            740                 745                 750

Asn Leu Ala Gln Tyr Asp Cys Ile Leu Ser Leu Ala Ala Thr Ser Cys
            755                 760                 765

Asn Val Asn Tyr Val Arg Pro Thr Phe Val Asn Gly Gln Gln Ala Ile
            770                 775                 780

Ile Ala Lys Asn Ala Arg Asn Pro Ile Ile Glu Ser Leu Asp Val His
785                 790                 795                 800

Tyr Val Pro Asn Asp Ile Met Met Ser Pro Glu Asn Gly Lys Ile Asn
            805                 810                 815

Ile Ile Thr Gly Pro Asn Met Gly Gly Lys Ser Ser Tyr Ile Arg Gln
            820                 825                 830

Val Ala Leu Leu Thr Ile Met Ala Gln Ile Gly Ser Phe Val Pro Ala
            835                 840                 845

Glu Glu Ile Arg Leu Ser Ile Phe Glu Asn Val Leu Thr Arg Ile Gly
            850                 855                 860

Ala His Asp Asp Ile Ile Asn Gly Asp Ser Thr Phe Lys Val Glu Met
865                 870                 875                 880

Leu Asp Ile Leu His Ile Leu Lys Asn Cys Asn Lys Arg Ser Leu Leu
            885                 890                 895

Leu Leu Asp Glu Val Gly Arg Gly Thr Gly Thr His Asp Gly Ile Ala
            900                 905                 910

Ile Ser Tyr Ala Leu Ile Lys Tyr Phe Ser Glu Leu Ser Asp Cys Pro
            915                 920                 925

Leu Ile Leu Phe Thr Thr His Phe Pro Met Leu Gly Glu Ile Lys Ser
            930                 935                 940

Pro Leu Ile Arg Asn Tyr His Met Asp Tyr Val Glu Glu Gln Lys Thr
945                 950                 955                 960

Gly Glu Asp Trp Met Ser Val Ile Phe Leu Tyr Lys Leu Lys Lys Gly
            965                 970                 975
```

```
Leu Thr Tyr Asn Ser Tyr Gly Met Asn Val Ala Lys Leu Ala Arg Leu
            980                 985                 990

Asp Lys Asp Ile Ile Asn Arg Ala Phe Ser Ile Ser Glu Glu Leu Arg
            995                1000                1005

Lys Glu Ser Ile Asn Glu Asp Ala Leu Lys Leu Phe Ser Ser Leu Lys
           1010                1015                1020

Arg Ile Leu Lys Ser Asp Asn Ile Thr Ala Thr Asp Lys Leu Ala Lys
1025                1030                1035                1040

Leu Leu Ser Leu Asp Ile His
                1045

<210> SEQ ID NO 100
<211> LENGTH: 1242
<212> TYPE: PRT
<213> ORGANISM: Saccharomyces cerevisiae

<400> SEQUENCE: 100

Met Ala Pro Ala Thr Pro Lys Thr Ser Lys Thr Ala His Phe Glu Asn
1               5                  10                  15

Gly Ser Thr Ser Ser Gln Lys Lys Met Lys Gln Ser Ser Leu Leu Ser
                20                  25                  30

Phe Phe Ser Lys Gln Val Pro Ser Gly Thr Pro Ser Lys Lys Val Gln
            35                  40                  45

Lys Pro Thr Pro Ala Thr Leu Glu Asn Thr Ala Thr Asp Lys Ile Thr
    50                  55                  60

Lys Asn Pro Gln Gly Gly Lys Thr Gly Lys Leu Phe Val Asp Val Asp
65                  70                  75                  80

Glu Asp Asn Asp Leu Thr Ile Ala Glu Glu Thr Val Ser Thr Val Arg
                85                  90                  95

Ser Asp Ile Met His Ser Gln Glu Pro Gln Ser Asp Thr Met Leu Asn
                100                 105                 110

Ser Asn Thr Thr Glu Pro Lys Ser Thr Thr Thr Asp Glu Asp Leu Ser
            115                 120                 125

Ser Ser Gln Ser Arg Arg Asn His Lys Arg Arg Val Asn Tyr Ala Glu
    130                 135                 140

Ser Asp Asp Asp Ser Asp Thr Thr Phe Thr Ala Lys Arg Lys Lys Lys
145                 150                 155                 160

Gly Lys Val Val Asp Ser Glu Ser Asp Glu Asp Glu Tyr Leu Pro Asp
                165                 170                 175

Lys Asn Asp Gly Asp Glu Asp Asp Ile Ala Asp Asp Lys Glu Asp
                180                 185                 190

Ile Lys Gly Glu Leu Ala Glu Asp Ser Gly Asp Asp Asp Leu Ile
            195                 200                 205

Ser Leu Ala Glu Thr Thr Ser Lys Lys Lys Phe Ser Tyr Asn Thr Ser
    210                 215                 220

His Ser Ser Ser Pro Phe Thr Arg Asn Ile Ser Arg Asp Asn Ser Lys
225                 230                 235                 240

Lys Lys Ser Arg Pro Asn Gln Ala Pro Ser Arg Ser Tyr Asn Pro Ser
                245                 250                 255

His Ser Gln Pro Ser Ala Thr Ser Lys Ser Ser Lys Phe Asn Lys Gln
            260                 265                 270

Asn Glu Glu Arg Tyr Gln Trp Leu Val Asp Glu Arg Asp Ala Gln Arg
        275                 280                 285

Arg Pro Lys Ser Asp Pro Glu Tyr Asp Pro Arg Thr Leu Tyr Ile Pro
    290                 295                 300
```

-continued

Ser Ser Ala Trp Asn Lys Phe Thr Pro Phe Glu Lys Gln Tyr Trp Glu
305                 310                 315                 320

Ile Lys Ser Lys Met Trp Asp Cys Ile Val Phe Phe Lys Lys Gly Lys
                325                 330                 335

Phe Phe Glu Leu Tyr Glu Lys Asp Ala Leu Leu Ala Asn Ala Leu Phe
            340                 345                 350

Asp Leu Lys Ile Ala Gly Gly Arg Ala Asn Met Gln Leu Ala Gly
            355                 360                 365

Ile Pro Glu Met Ser Phe Glu Tyr Trp Ala Ala Gln Phe Ile Gln Met
        370                 375                 380

Gly Tyr Lys Val Ala Lys Val Asp Gln Arg Glu Ser Met Leu Ala Lys
385                 390                 395                 400

Glu Met Arg Glu Gly Ser Lys Gly Ile Val Lys Arg Glu Leu Gln Cys
                405                 410                 415

Ile Leu Thr Ser Gly Thr Leu Thr Asp Gly Asp Met Leu His Ser Asp
            420                 425                 430

Leu Ala Thr Phe Cys Leu Ala Ile Arg Glu Glu Pro Gly Asn Phe Tyr
            435                 440                 445

Asn Glu Thr Gln Leu Asp Ser Ser Thr Ile Val Gln Lys Leu Asn Thr
450                 455                 460

Lys Ile Phe Gly Ala Ala Phe Ile Asp Thr Ala Thr Gly Glu Leu Gln
465                 470                 475                 480

Met Leu Glu Phe Glu Asp Asp Ser Glu Cys Thr Lys Leu Asp Thr Leu
                485                 490                 495

Met Ser Gln Val Arg Pro Met Glu Val Val Met Glu Arg Asn Asn Leu
                500                 505                 510

Ser Thr Leu Ala Asn Lys Ile Val Lys Phe Asn Ser Ala Pro Asn Ala
            515                 520                 525

Ile Phe Asn Glu Val Lys Ala Gly Glu Glu Phe Tyr Asp Cys Asp Lys
            530                 535                 540

Thr Tyr Ala Glu Ile Ile Ser Ser Glu Tyr Phe Ser Thr Glu Asp
545                 550                 555                 560

Trp Pro Glu Val Leu Lys Ser Tyr Tyr Asp Thr Gly Lys Lys Val Gly
                565                 570                 575

Phe Ser Ala Phe Gly Gly Leu Leu Tyr Tyr Leu Lys Trp Leu Lys Leu
            580                 585                 590

Asp Lys Asn Leu Ile Ser Met Lys Asn Ile Lys Glu Tyr Asp Phe Val
        595                 600                 605

Lys Ser Gln His Ser Met Val Leu Asp Gly Ile Thr Leu Gln Asn Leu
610                 615                 620

Glu Ile Phe Ser Asn Ser Phe Asp Gly Ser Asp Lys Gly Thr Leu Phe
625                 630                 635                 640

Lys Leu Phe Asn Arg Ala Ile Thr Pro Met Gly Lys Arg Met Met Lys
                645                 650                 655

Lys Trp Leu Met His Pro Leu Leu Arg Lys Asn Asp Ile Glu Ser Arg
                660                 665                 670

Leu Asp Ser Val Asp Ser Leu Leu Gln Asp Ile Thr Leu Arg Glu Gln
            675                 680                 685

Leu Glu Ile Thr Phe Ser Lys Leu Pro Asp Leu Glu Arg Met Leu Ala
            690                 695                 700

Arg Ile His Ser Arg Thr Ile Lys Val Lys Asp Phe Glu Lys Val Ile
705                 710                 715                 720

```
Thr Ala Phe Glu Thr Ile Ile Glu Leu Gln Asp Ser Leu Lys Asn Asn
                725                 730                 735

Asp Leu Lys Gly Asp Val Ser Lys Tyr Ile Ser Ser Phe Pro Glu Gly
                740                 745                 750

Leu Val Glu Ala Val Lys Ser Trp Thr Asn Ala Phe Glu Arg Gln Lys
                755                 760                 765

Ala Ile Asn Glu Asn Ile Ile Val Pro Gln Arg Gly Phe Asp Ile Glu
    770                 775                 780

Phe Asp Lys Ser Met Asp Arg Ile Gln Glu Leu Glu Asp Glu Leu Met
785                 790                 795                 800

Glu Ile Leu Met Thr Tyr Arg Lys Gln Phe Lys Cys Ser Asn Ile Gln
                805                 810                 815

Tyr Lys Asp Ser Gly Lys Glu Ile Tyr Thr Ile Glu Ile Pro Ile Ser
                820                 825                 830

Ala Thr Lys Asn Val Pro Ser Asn Trp Val Gln Met Ala Ala Asn Lys
                835                 840                 845

Thr Tyr Lys Arg Tyr Ser Asp Glu Val Arg Ala Leu Ala Arg Ser
                850                 855                 860

Met Ala Glu Ala Lys Glu Ile His Lys Thr Leu Glu Glu Asp Leu Lys
865                 870                 875                 880

Asn Arg Leu Cys Gln Lys Phe Asp Ala His Tyr Asn Thr Ile Trp Met
                885                 890                 895

Pro Thr Ile Gln Ala Ile Ser Asn Ile Asp Cys Leu Leu Ala Ile Thr
                900                 905                 910

Arg Thr Ser Glu Tyr Leu Gly Ala Pro Ser Cys Arg Pro Thr Ile Val
                915                 920                 925

Asp Glu Val Asp Ser Lys Thr Asn Thr Gln Leu Asn Gly Phe Leu Lys
                930                 935                 940

Phe Lys Ser Leu Arg His Pro Cys Phe Asn Leu Gly Ala Thr Thr Ala
945                 950                 955                 960

Lys Asp Phe Ile Pro Asn Asp Ile Glu Leu Gly Lys Glu Gln Pro Arg
                965                 970                 975

Leu Gly Leu Leu Thr Gly Ala Asn Ala Ala Gly Lys Ser Thr Ile Leu
                980                 985                 990

Arg Met Ala Cys Ile Ala Val Ile Met Ala Gln Met Gly Cys Tyr Val
                995                 1000                1005

Pro Cys Glu Ser Ala Val Leu Thr Pro Ile Asp Arg Ile Met Thr Arg
    1010                1015                1020

Leu Gly Ala Asn Asp Asn Ile Met Gln Gly Lys Ser Thr Phe Phe Val
1025                1030                1035                1040

Glu Leu Ala Glu Thr Lys Lys Ile Leu Asp Met Ala Thr Asn Arg Ser
                1045                1050                1055

Leu Leu Val Val Asp Glu Leu Gly Arg Gly Gly Ser Ser Ser Asp Gly
                1060                1065                1070

Phe Ala Ile Ala Glu Ser Val Leu His His Val Ala Thr His Ile Gln
                1075                1080                1085

Ser Leu Gly Phe Phe Ala Thr His Tyr Gly Thr Leu Ala Ser Ser Phe
    1090                1095                1100

Lys His His Pro Gln Val Arg Pro Leu Lys Met Ser Ile Leu Val Asp
1105                1110                1115                1120

Glu Ala Thr Arg Asn Val Thr Phe Leu Tyr Lys Met Leu Glu Gly Gln
                1125                1130                1135

Ser Glu Gly Ser Phe Gly Met His Val Ala Ser Met Cys Gly Ile Ser
```

-continued

```
             1140                1145                1150
Lys Glu Ile Ile Asp Asn Ala Gln Ile Ala Ala Asp Asn Leu Glu His
            1155                1160            1165

Thr Ser Arg Leu Val Lys Glu Arg Asp Leu Ala Ala Asn Asn Leu Asn
    1170            1175                1180

Gly Glu Val Val Ser Val Pro Gly Gly Leu Gln Ser Asp Phe Val Arg
1185                1190            1195                1200

Ile Ala Tyr Gly Asp Gly Leu Lys Asn Thr Lys Leu Gly Ser Gly Glu
                1205            1210            1215

Gly Val Leu Asn Tyr Asp Trp Asn Ile Lys Arg Asn Val Leu Lys Ser
                1220            1225            1230

Leu Phe Ser Ile Ile Asp Asp Leu Gln Ser
        1235            1240
```